(12) United States Patent
Nagae et al.

(10) Patent No.: US 12,004,722 B2
(45) Date of Patent: Jun. 11, 2024

(54) MICROSCOPE SYSTEM AND MEDICAL LIGHT SOURCE APPARATUS

(71) Applicant: Sony Corporation, Tokyo (JP)

(72) Inventors: Satoshi Nagae, Tokyo (JP); Tomoyuki Oki, Kanagawa (JP); Yuichi Takahashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 840 days.

(21) Appl. No.: 17/044,336

(22) PCT Filed: Apr. 1, 2019

(86) PCT No.: PCT/JP2019/014444
§ 371 (c)(1),
(2) Date: Oct. 1, 2020

(87) PCT Pub. No.: WO2019/198553
PCT Pub. Date: Oct. 17, 2019

(65) Prior Publication Data
US 2021/0076921 A1    Mar. 18, 2021

(30) Foreign Application Priority Data

Apr. 11, 2018 (JP) .................................. 2018-076072
Sep. 28, 2018 (JP) .................................. 2018-185381

(51) Int. Cl.
*A61B 1/06* (2006.01)
*G02B 23/24* (2006.01)
(Continued)

(52) U.S. Cl.
CPC ........ *A61B 1/0638* (2013.01); *G02B 23/2461* (2013.01); *G02B 27/1006* (2013.01); *G02B 27/141* (2013.01)

(58) Field of Classification Search
CPC .............. A61B 1/0638; G02B 23/2461; G02B 27/1006; G02B 27/141; G02B 27/145; G02B 27/149
See application file for complete search history.

(56) References Cited

U.S. PATENT DOCUMENTS 6,876,679 B1 * 4/2005 Bowler .............. G02B 6/29365
372/101
10,610,082 B2 * 4/2020 Tanaka ................. A61B 1/0684
(Continued)

FOREIGN PATENT DOCUMENTS

| CN | 104293648 B | 8/2016 |
| EP | 1526373 A1 | 4/2005 |

(Continued)

OTHER PUBLICATIONS

International Search Report and Written Opinion dated Jul. 16, 2019 for PCT/JP2019/014444 filed on Apr. 1, 2019, 8 pages.

*Primary Examiner* — Anh Tuan T Nguyen
*Assistant Examiner* — Shankar Raj Ghimire
(74) *Attorney, Agent, or Firm* — XSENSUS LLP

(57) ABSTRACT

A medical observation system for observing a biological object includes a medical light source apparatus for illuminating the biological object. The medical light source apparatus includes a first, second and third laser light sources that emit respective first, second, and third laser light beams. First and second laser light beams have different wavelength bands. The medical light source apparatus also includes an optical assembly including a reflecting surface disposed to reflect the first laser light beam, cause the second laser light beam to be transmitted therethrough, and guide the first laser light beam and the second laser light beam in a same direction. The medical light source apparatus also includes a reflection mirror having a reflecting surface that is not parallel with the reflecting surface of the optical assembly.

(Continued)

The system includes a medical observation device including a detector for detecting a light received from the biological object.

21 Claims, 21 Drawing Sheets

(51) Int. Cl.
*G02B 27/10* (2006.01)
*G02B 27/14* (2006.01)

(56) References Cited

U.S. PATENT DOCUMENTS

| | | | | |
|---|---|---|---|---|
| 10,842,367 | B2* | 11/2020 | Matsunobu | A61B 1/0669 |
| 11,559,194 | B2* | 1/2023 | Onobori | A61B 1/07 |
| 2002/0014595 | A1* | 2/2002 | Sendai | A61B 1/0005 |
| | | | | 250/458.1 |
| 2005/0213090 | A1* | 9/2005 | Namba | G02B 21/0076 |
| | | | | 356/318 |
| 2006/0072118 | A1* | 4/2006 | Chan | A61B 5/14546 |
| | | | | 356/495 |
| 2007/0098028 | A1* | 5/2007 | Alcock | H01S 5/40 |
| | | | | 372/50.122 |
| 2007/0299309 | A1* | 12/2007 | Seibel | A61B 1/0638 |
| | | | | 600/117 |
| 2008/0100848 | A1* | 5/2008 | Kobayashi | G01B 9/02009 |
| | | | | 356/497 |
| 2011/0013200 | A1* | 1/2011 | Kato | G01B 11/002 |
| | | | | 356/625 |
| 2011/0134497 | A1* | 6/2011 | Horimai | G03H 1/30 |
| | | | | 359/30 |
| 2011/0234923 | A1* | 9/2011 | Yamagishi | H04N 9/3111 |
| | | | | 348/757 |
| 2012/0307512 | A1* | 12/2012 | Cogger | G02B 21/06 |
| | | | | 362/231 |
| 2013/0335797 | A1* | 12/2013 | Cooper | G02B 21/16 |
| | | | | 359/388 |
| 2015/0092118 | A1* | 4/2015 | Hada | B60K 35/00 |
| | | | | 349/11 |
| 2015/0146174 | A1* | 5/2015 | Ferri | G03B 21/204 |
| | | | | 353/31 |
| 2015/0219985 | A1* | 8/2015 | Shouji | G03B 21/208 |
| | | | | 353/31 |
| 2015/0335232 | A1* | 11/2015 | Ito | A61B 1/07 |
| | | | | 362/11 |
| 2015/0381909 | A1* | 12/2015 | Butte | G06T 7/0012 |
| | | | | 250/578.1 |
| 2016/0062103 | A1* | 3/2016 | Yang | A61B 1/07 |
| | | | | 250/552 |
| 2016/0143520 | A1* | 5/2016 | Masaki | A61B 1/00009 |
| | | | | 600/109 |
| 2017/0020377 | A1* | 1/2017 | Takeuchi | A61B 1/00006 |
| 2017/0020627 | A1* | 1/2017 | Tesar | A61B 90/361 |
| 2017/0123237 | A1* | 5/2017 | DeMuth | B22F 12/70 |
| 2017/0209050 | A1* | 7/2017 | Fengler | G01J 3/4406 |
| 2018/0064321 | A1* | 3/2018 | Muramatsu | A61B 1/00057 |
| 2019/0011365 | A1* | 1/2019 | Ge | G02B 21/0076 |
| 2019/0206050 | A1* | 7/2019 | Yates | A61B 1/043 |
| 2019/0215925 | A1* | 7/2019 | Tanaka | A61B 1/0638 |
| 2020/0041257 | A1* | 2/2020 | Egan | H01S 5/4012 |
| 2020/0178781 | A1* | 6/2020 | Tabata | A61B 1/063 |
| 2020/0192017 | A1* | 6/2020 | Dülk | A61B 1/046 |
| 2020/0205648 | A1* | 7/2020 | Onobori | A61B 1/07 |
| 2021/0124178 | A1* | 4/2021 | Matsunobu | A61B 5/0071 |
| 2021/0190692 | A1* | 6/2021 | Aizawa | G01N 21/6458 |
| 2022/0244553 | A1* | 8/2022 | Arntsen | H04N 9/3147 |
| 2022/0390819 | A1* | 12/2022 | Chien | G03B 21/2013 |
| 2023/0092006 | A1* | 3/2023 | Jiang | G01N 21/6456 |
| | | | | 250/458.1 |

FOREIGN PATENT DOCUMENTS

| | | | |
|---|---|---|---|
| JP | 2008-256979 A | 10/2008 | |
| WO | 2017/041703 A1 | 3/2017 | |
| WO | WO-2019069775 A1 * | 4/2019 | G02B 26/10 |

* cited by examiner

MICROSCOPE SYSTEM AND MEDICAL LIGHT SOURCE APPARATUS

CROSS-REFERENCE TO RELATED APPLICATIONS

This application is based on PCT filing PCT/JP2019/014444, filed Apr. 1, 2019, which claims the benefit of Japanese Priority Patent Application JP 2018-076072, filed Apr. 11, 2018, and JP 2018-185381, filed Sep. 28, 2018, the entire contents of each are incorporated herein by reference.

TECHNICAL FIELD

The present technology relates to a microscope system and a medical light source apparatus.

BACKGROUND ART

In the medical field, a medical observation system that illuminates and captures images of a biological object, for example, including an endoscope system that images the inside of an observation object (inside of a living body) such as a human and observes the inside of the living body has been known. The endoscope system includes an endoscope to be inserted into a living body and a light source apparatus (see, for example, Patent Literature 1). Patent Literature 1 describes that a white light beam is generated by mixing colors of light beams from a red light source, a blue light source, and a green light source provided in a light source apparatus, and used as illumination light.

Further, in recent years, in the medical field, it is desired to mount an infrared laser light source or violet laser light source on a light source apparatus, for special light observation.

CITATION LIST

Patent Literature

PTL 1: WO 2015/166728

SUMMARY

Technical Problem

As described above, as the number of laser light sources mounted on a light source apparatus increases, the size of the light source apparatus increases. Meanwhile, it is desirable to reduce the size of the light source apparatus in the medical site.

In view of the circumstances as described above, it is an object of the present technology to provide a microscope system and a medical light source apparatus that can be miniaturized.

Solution to Problem

In order to achieve the above-mentioned object, a medical observation system for observing a biological object includes a medical light source apparatus for illuminating the biological object. The medical light source apparatus includes a first laser light source configured to emit a first laser light beam, a second laser light source configured to emit a second laser light beam having a wavelength band different from a wavelength band of the first laser light beam, an optical assembly including a reflecting surface disposed to reflect the first laser light beam, cause the second laser light beam to be transmitted therethrough, and guide the first laser light beam and the second laser light beam in a same direction. The medical light source apparatus also includes a reflection mirror having a reflecting surface that is not parallel with the reflecting surface of the optical assembly and configured to reflect the second laser light beam to cause the second laser light beam to enter the optical assembly. The medical observation system also includes a medical observation device including a detector for detecting a light received from the biological object.

With such a configuration, in the medical light source apparatus, since the first laser light source and the second laser light source are not arranged side by side so that the emitting direction of the laser light beam to be emitted is in the same direction, the optical path lengths of the first laser light beam and the second laser light beam to a laser-light-entering object such as a condenser lens can be substantially the same and shortened, and the entire optical system can be miniaturized.

In order to achieve the above-mentioned object, an embodiment of a medical light source apparatus for illuminating a biological object includes a first laser light source configured to emit a first laser light beam; a second laser light source configured to emit a second laser light beam having a wavelength band different from a wavelength band of the first laser light beam; and an optical assembly including a reflecting surface and disposed to reflect the first laser light beam, cause the second laser light beam to be transmitted therethrough, guide the first laser light beam and the second laser light beam in a same direction, and produce output light that illuminates the biological object. The medical light source apparatus also includes a reflection mirror having a reflecting surface that is not parallel with the reflecting surface of the optical assembly and configured to reflect the second laser light beam to cause the second laser light beam to enter the optical assembly.

With such a configuration, since the first laser light source and the second laser light source are not arranged side by side so that the emitting direction of the laser light beam to be emitted is in the same direction, the optical path lengths of the first laser light beam and the second laser light beam to a laser-light-entering object such as a condenser lens can be substantially the same and shortened, and the entire optical system can be miniaturized.

The first laser light beam and the second laser light beam may be emitted in opposite directions, which are directed approximately 180 degrees from each other. The reflecting surface of the optical assembly may be perpendicular to the reflecting surface of the reflection mirror.

The optical assembly, which may include a dichroic mirror, a dichroic filter, or a prism, may be configured to reflect the first laser light beam to redirect an optical path of the first laser light beam by 90 degrees, and the reflection mirror may be further configured to reflect the second laser light beam to redirect an optical path of the second laser light beam by 90 degrees.

The first laser light beam may have a wavelength shorter than a wavelength of the second laser light beam.

With such a configuration, it is possible to prevent optical characteristics of the optical assembly from being deteriorated with time, and obtain illumination light with stable color for a long time.

The first laser light source, the second laser light source, the optical assembly, and the reflection mirror may be configured to form one group, the medical light source apparatus may further include a third laser light source configured to emit a third laser light beam; a fourth laser light source configured to emit a fourth laser light beam having a wavelength band different from a wavelength band of the third laser light beam; a second optical assembly including a reflecting surface and disposed to reflect the third laser light beam, cause the fourth laser light beam to be transmitted therethrough, guide the third laser light beam and the fourth laser light beam in a same direction, and produce a second output light that illuminates the biological object; a second reflection mirror having a reflecting surface that is not parallel with the reflecting surface of the second optical assembly and configured to reflect the fourth laser light beam to cause the fourth laser light beam to enter the second optical assembly, the third laser light source, the fourth laser light source, the second optical assembly, and the second reflection mirror are configured to form a second group; and a condenser lens that receives the output light from the first group and the second output light from the second group and condenses the received light.

With such a configuration, since the laser light sources are arranged so that the direction of the optical path through which the laser light beam transmitted through or reflected by the optical assembly reaches the condenser lens in each group and the direction of the optical path through which the laser light beam emitted from each laser light source reaches the optical assembly or the reflection mirror are different from each other, the distance between the optical paths of light beams generated in the plurality of groups can be narrowed without being affected by the size of the laser light source. Therefore, it is possible to reduce the effective diameter of the condenser lens, and reduce the size of the entire optical system.

The medical light source apparatus may further include a rod integrator that receives a light beam condensed by the condenser lens.

By providing the rod integrator as described above, it is possible to make the energy distribution of light that has entered the rod integrator uniform and emit it, thereby obtaining illumination light having uniform illumination distribution.

The medical light source apparatus may include the first laser light source that is configured to emit the first laser light beam having a red wavelength band, the second laser light source that is configured to emit the second laser light beam having a blue wavelength band, a third laser light source that is configured to emit a third laser light beam having a green wavelength band. The medical light source apparatus further includes a condenser lens that receives the output light from the first group and condenses the received light. The received light received by the condenser lens may include a red light beam from the first laser light source, a blue light beam from the second laser light source, and a green light beam from the third laser light source that overlap each other at the condenser lens. An outermost portion of the received light at the condenser lens may include a portion of the red light beam, a portion of the blue light beam and a portion of the green light beam.

With such a configuration, it is possible to obtain illumination light with suppressed color unevenness in the irradiation area.

The medical light source apparatus may include a fifth laser light source configured to emit a fifth laser light beam; a sixth laser light source configured to emit a sixth laser light beam having a wavelength band different from a wavelength band of the fifth laser light beam; a third optical assembly including a reflecting surface and disposed to reflect the fifth laser light beam, cause the sixth laser light beam to be transmitted therethrough, guide the fifth laser light beam and the sixth laser light beam in a same direction, and produce a third output light that illuminates the biological object. The apparatus may further include a third reflection mirror having a reflecting surface that is not parallel with the reflecting surface of the third optical assembly and configured to reflect the sixth laser light beam to cause the sixth laser light beam to enter the third optical assembly. The fifth laser light source, the sixth laser light source, the third optical assembly, and the third reflection mirror are configured to form a third group. Two groups out of the first, second, and third groups include the green laser light source and the red laser light source, and a remaining one of the first, second, and third groups includes the blue laser light source and the green laser light source.

With such a configuration, by using the plurality of laser light sources of the same color, it is easy to generate illumination light of a desired color, and it is possible to increase the output of illumination light.

The medical light source apparatus may further include an infrared laser light source configured to emit an infrared light beam that enters the condenser lens.

Accordingly, it is possible to perform special observation using an infrared light beam.

The medical light source apparatus may further include a violet laser light source configured to emit a violet light beam that enters the condenser lens.

Accordingly, it is possible to perform special observation using a violet light beam.

The medical light source apparatus may further include an enclosure, the first laser light source and the second laser light source being placed on the same surface of the enclosure.

With such a configuration, it is possible to reduce the size of the entire optical system. Further, for example, in order to cool the heat generated from each laser light source, it only needs to provide one cooling mechanism on the surface of the enclosure opposite to the surface on which the laser light source is placed, and it is possible to reduce the size of the medical light source apparatus as compared with the case where two or more cooling mechanisms are provided.

The medical light source apparatus may further include a heat sink configured to cool (receive) heat generated from the first laser light source and the second laser light source. The heat sink may include a Peltier device.

An intensity of the output light may be adjusted by controlling output intensity of the first laser light beam and the second laser light beam.

The medical light source apparatus may be configured to supply the output light to a microscope or an endoscope. The optical viewing assembly may include a microscope or an endoscope.

Advantageous Effects

As described above, in accordance with to the present technology, it is possible to obtain a medical light source apparatus and an endoscope system that can be miniaturized. Note that, the advantages disclosed herein are merely examples and not limited thereto, and other advantages may be additionally obtained.

DESCRIPTION OF EMBODIMENTS

Hereinafter, an endoscope system to which a medical light source apparatus according to an embodiment of the present technology is applied will be described with reference to the drawings.

Configuration of Endoscope System

Figure 1:
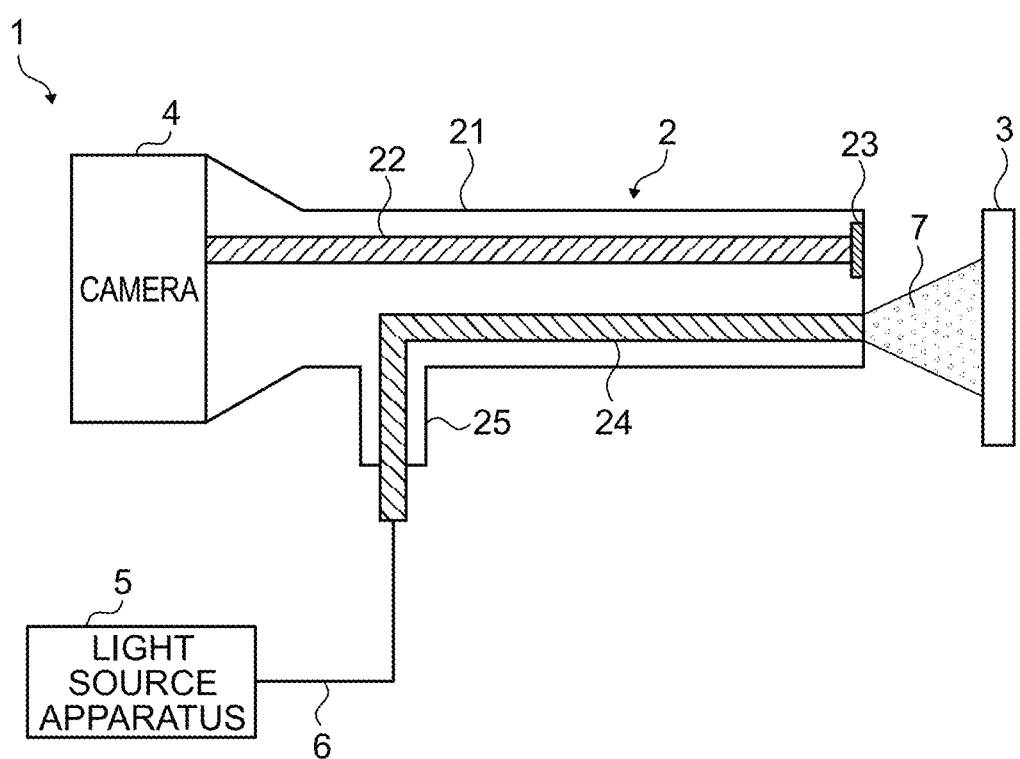
FIG. 1 is a schematic diagram of an example of a configuration of an endoscope system to which a medical light source apparatus according to a first embodiment of the present technology is applied.

An endoscope system 1 according to this embodiment will be described with reference to FIG. 1.

The endoscope system 1 is used in the medical field, and is a system for observing the inside of an observation object (inside of a living body) such as a human. The endoscope system 1 includes an endoscope 2, a camera 4, a medical light source apparatus 5 (hereinafter, referred to as the light source apparatus 5), and a light guide cable 6. The light source apparatus 5 is configured to be connectable to the endoscope 2.

The endoscope 2 includes an insertion tube 21 to be inserted into a living body, an optical system 22, an objective lens 23, and a light guide 24. The endoscope 2 irradiates, from the tip of the insertion tube 21, a part 3 to be observed that is an irradiated body with an irradiation light beam 7 supplied from the light source apparatus 5.

The insertion tube 21 is hard or at least partially soft, and has an elongated shape. On the outer peripheral surface of the insertion tube 21, a connection connector 25 that protrudes along the radial direction is provided. To the connection connector 25, another end of the light guide cable 6 is connected The objective lens 23 is provided at the tip inside the insertion tube 21, and condenses the light of the subject image.

The optical system 22 is provided inside the insertion tube 21, and guides the light of the subject image condensed by the objective lens 23 into the base end of the insertion tube 21.

The light guide 24 as a light guide body includes, for example, an optical fiber. The light guide 24 is routed from the tip to the side of the base end in the insertion tube 21, and extends so as to bend substantially perpendicular toward the connection connector 25 side. Surfaces that are perpendicular to each other are arranged approximately 90 degrees from each other.

In the state in which the light guide cable 6 is connected to the connection connector 25, a light beam supplied from the light source apparatus 5 is guided by the light guide cable 6 and the light guide 24, emitted from the tip of the insertion tube 21, and applied to the part 3 to be observed in a living body.

To the light source apparatus 5, an end of the light guide cable 6 is connected. The light source apparatus 5 supplies, to the light guide cable 6, a light beam to be applied to the part 3 to be observed. Details of the light source apparatus 5 will be described later.

One end of the light guide cable 6 is detachably connected to the light source apparatus 5, and the other end is detachably connected to the connection connector 25 of the insertion tube 21. The light guide cable 6 transmits, from the one end to the other end, the light beam supplied from the light source apparatus 5, and supplies it to the insertion tube 21.

The camera 4 is detachably connected to the base end of the insertion tube 21. The camera 4 includes an image sensor (not shown), and images the part 3 to be observed.

Configuration of Light Source Apparatus

First Embodiment

Figure 2:
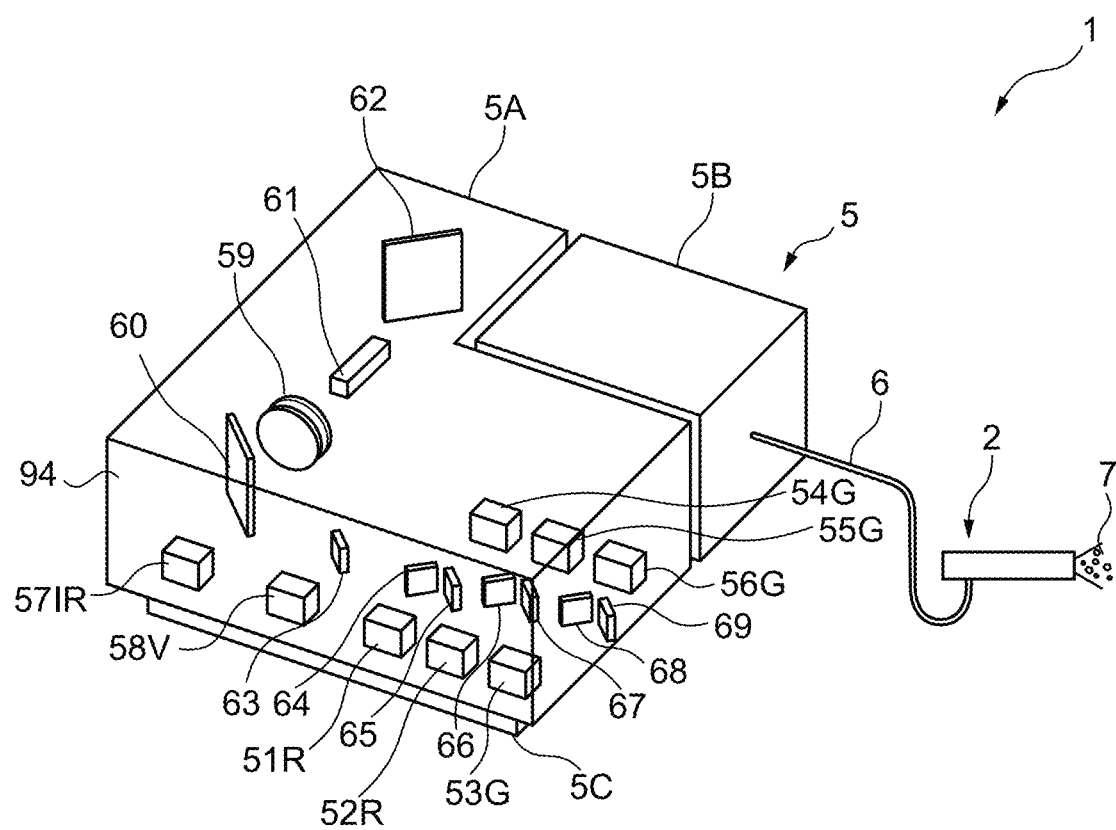
FIG. 2 is a schematic diagram of the endoscope system in FIG. 1, and is a perspective view for describing the configuration of the medical light source apparatus.
Figure 3:
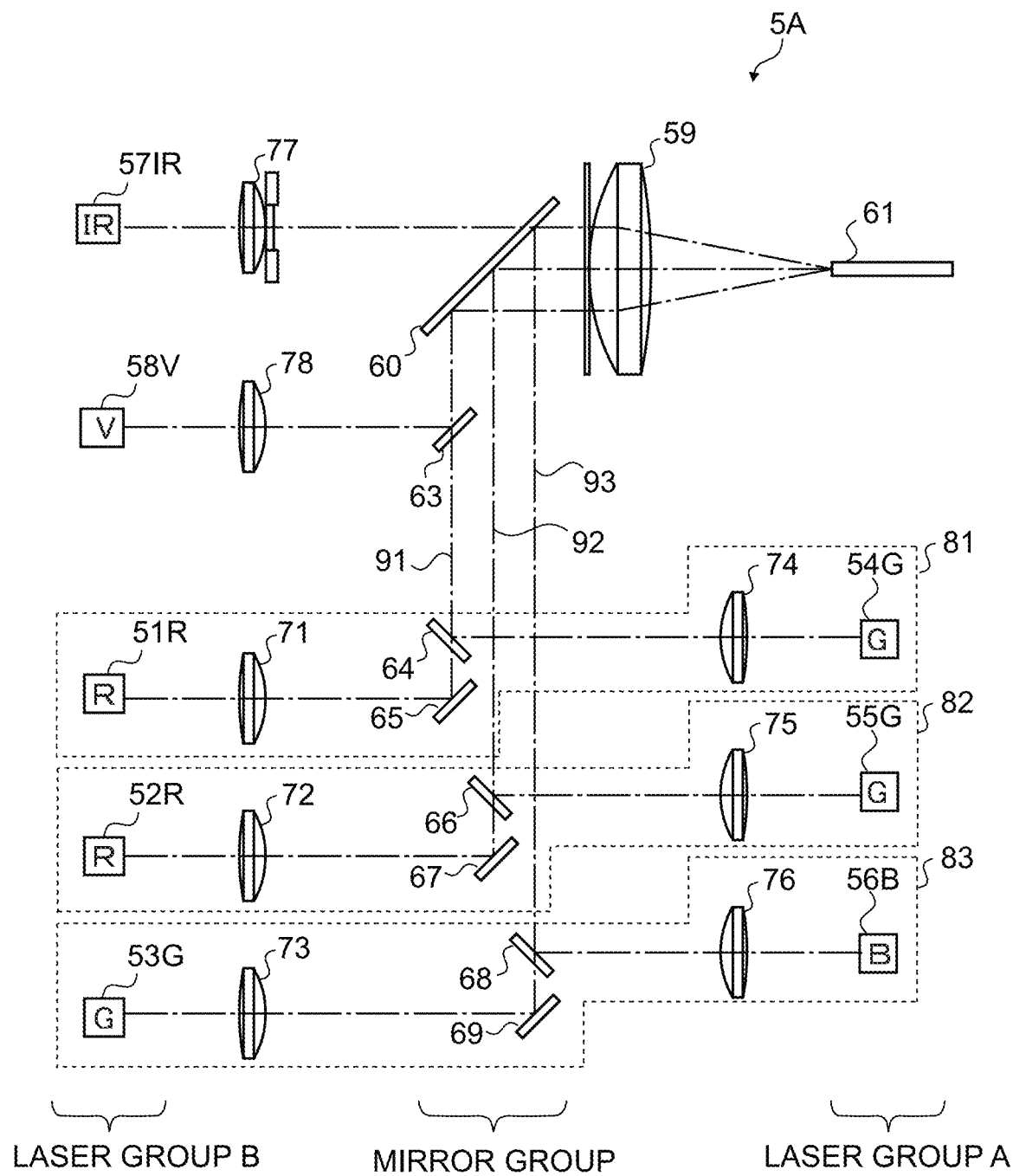
FIG. 3 is a diagram of the medical light source apparatus in FIG. 2 viewed from the above, and is a diagram for describing arrangement of an optical system.

FIG. 2 is a schematic diagram of the endoscope system 1, and is a perspective view for describing a configuration example of the light source apparatus 5. FIG. 3 is a schematic diagram showing a configuration example of a narrow-band light source unit 5A constituting a part of the light source apparatus 5.

As shown in FIG. 2, the light source apparatus 5 includes the narrow-band light source unit 5A, a multiplexing unit 5B, and a cooling unit 5C that functions as a cooling mechanism.

The narrow-band light source unit 5A includes an enclosure 94 having a hollow portion, and a plurality of laser light sources arranged in the hollow portion of the enclosure 94. Each of the plurality of laser light sources outputs laser light beam of the corresponding color, which is a narrow-band light beam. In this embodiment, since a laser light source that has a small light emission area and a narrow radiation angle and is capable of reducing the beam diameter by using a lens is used, the diameter of the endoscope can be reduced. Since the diameter of the endoscope to be inserted into the body of patient is reduced as described above, it is possible to reduce the physical burden on the patient. Details of the narrow-band light source unit 5A will be described later.

The multiplexing unit 5B includes a broadband light source (not shown) formed of a white LED (Light Emitting Diode), a dichroic mirror (not shown), and a condenser lens (not shown). The broadband light source emits a white light beam in the band of 400 nm to 700 nm, for example.

The multiplexing unit 5B is configured to be capable of generating a multiplexed white light beam obtained by combining the light beam from the narrow-band light source unit 5A and the white light beam emitted from the broadband light source by the dichroic mirror, and the multiplexed white light beam is condensed by the condenser lens. From the multiplexing unit 5B, the light beam condensed by the condenser lens is supplied to the endoscope 2 via the light guide cable 6.

The cooling unit 5C is disposed in contact with the outer bottom surface of the enclosure 94. Although the specific configuration of the cooling unit 5C is not limited, the cooling unit 5C typically includes a Peltier device and a heat sink provided in contact with each other. The plurality of laser light sources are placed on the inner bottom surface of the enclosure 94. The cooling unit 5C is provided on the outer bottom surface facing the inner bottom surface, and effectively cools the heat generated from each laser light source. The plurality of laser light sources placed on the same surface of the enclosure 94 are arranged so that the emission directions of laser light beams to be emitted therefrom are in parallel with each other.

As shown in FIG. 2 and FIG. 3, the narrow-band light source unit 5A includes a first optical system group 81, a second optical system group 82, a third optical system group 83, an infrared laser light source (hereinafter, referred to as the IR light source) 57IR, a violet laser light source (hereinafter, referred to as the V light source) 58V, a collimating lens 77 for the IR light source, a collimating lens 78 for the V light source, a dichroic mirror 63 for the V light source, a dichroic mirror 60, a condenser lens 59, and a rod integrator 61.

The first optical system group 81 includes a first red laser light source (hereinafter, referred to as the R light source) 51R, a second green light source (hereinafter, referred to as the G light source) 54G, a collimating lens 71 for the first R light source, a collimating lens for the second G light source, a first dichroic mirror 64, and a first reflection mirror 65.

The second optical system group 82 includes a second R light source 52R, a third G light source 55G, a collimating lens 72 for the second R light source, a collimating lens 75 for the third G light source, a second dichroic mirror 66, and a second reflection mirror 67.

The third optical system group 83 includes a first G light source 53G, a blue light source (hereinafter, referred to as the B light source) 56B, a collimating lens 73 for the first G light source, a collimating lens 76 for the B light source, a third dichroic mirror 68, and a third reflection mirror 69.

The IR light source 57IR emits an infrared laser light beam (hereinafter, referred to as the infrared light beam). The IR light source 57IR includes, for example, two IR light sources that emit the infrared light beam in the infrared band of 790 nm to 820 nm with the center wavelength of 805 nm and the infrared light beam in the infrared wavelength band of 905 to 970 nm with the center wavelength of 940 nm.

The infrared light beam emitted from the IR light source 57IR is collimated and becomes a substantially parallel light beam by being transmitted through the collimating lens 77 for the IR light source, enters the dichroic mirror 60, is transmitted through the dichroic mirror 60, and enters the condenser lens 59. The infrared light beam that is emitted from the IR light source 57IR and is transmitted through the dichroic mirror 60 takes the same optical path as the optical path (third optical path 93 to be described later) of the multiplexed light beam generated by the third optical system group 83.

The V light source 58V emits a violet laser light beam in a violet wavelength band of 405 nm (hereinafter, referred to as the violet light beam). The violet light beam emitted from the V light source 58V is collimated and becomes a substantially parallel light beam by being transmitted through the collimating lens 78 for the V light source, enters the dichroic mirror 63 for the V light source, and is reflected by the mirror. The violet light beam reflected by the dichroic mirror 63 for the V light source takes the same optical path as the optical path (first optical path 91 to be described later) of the multiplexed light beam generated by the first optical system group 81, is reflected by the dichroic mirror 60, and enters the condenser lens 59.

The dichroic mirror 63 for the V light source reflects the violet light beam from the V light source 58V, and causes a red laser light beam (hereinafter, referred to as the red light beam) from the first R light source 51R and a green laser light beam (hereinafter, referred to as the green light beam) from the second G light source 54G to be transmitted therethrough.

The dichroic mirror 60 causes the infrared light beam from the IR light source 57IR to be transmitted therethrough, and reflects the violet light beam, the red light beam, the green light beam, and a blue laser light beam (hereinafter, referred to as the blue light beam) from the V light source 58V, the R light sources 51R and 52R, the G light sources 53G, 54G, and 55G, and the B light source 56B, respectively.

The condenser lens 59 condenses the incident light beam from each laser light source, and causes it to enter the rod integrator 61.

The rod integrator 61 has a quadrangular prism shape, is formed of synthetic quartz, and has optically polished six surfaces. The rod integrator 61 totally reflects the incident laser light beam therein, and guides it.

On the incident surface of the rod integrator 61, the laser light beam of each wavelength has spot-like spatial distribution due to being transmitted through the condenser lens 59. By repeated total reflection in the rod integrator 61, the spot-like spatial distribution is made uniform to form a far field pattern.

As described above, the rod integrator 61 makes the illumination distribution of the incident light beam uniform and emits it. It is desired to make the shape of the waveguide of the rod integrator 61 polygonal. With this, as compared with the case of a cylindrical shape, it is possible to increase the effect of making the light beam uniform, shorten the total length of the rod integrator 61, and further reduce the size of the entire optical system.

The first R light source 51R and the second R light source 52R each emit the red light beam in the red band of 630 nm to 645 nm with the center wavelength of 638 nm, for example. The R light sources 51R and 52R each include a semiconductor laser such as a GaInP quantum well structure laser diode.

The first G light source 53G, the second G light source 54G, and the third G light source 55G each emit the green light beam in the green band of 515 nm to 540 nm with the center wavelength of 525 nm, for example. The G light sources 53G, 54G, and 55G each include a semiconductor laser such as a GaInN quantum well structure laser diode.

The B light source 56B emits the blue light beam in the blue band of 435 nm to 465 nm with the center wavelength of 445 nm. The B light source 56B includes a semiconductor laser such as a GaInN quantum well structure laser diode.

In the first optical system group 81, the first dichroic mirror 64 reflects the green light beam from the second G light source 54G, and causes the red light beam from the first R light source 51R to be transmitted therethrough. The first reflection mirror 65 reflects the red light beam from the first R light source 51R to cause it to enter the first dichroic mirror 64.

The optical path of the red light beam from the first R light source 51R is converted by 90 degrees by the first reflection mirror 65, enters the first dichroic mirror 64, and is transmitted therethrough. The optical path of the green light beam from the second G light source 54G is converted by 90 degrees by the first dichroic mirror 64, and combined with the red light beam transmitted through the first dichroic mirror 64. The multiplexed light beam takes the first optical path 91. The multiplexed light beam enters the dichroic mirror 60, is reflected by the dichroic mirror 60, and enters the condenser lens 59. The light beam condensed by the condenser lens 59 enters the rod integrator 61.

In the second optical system group 82, the second dichroic mirror 66 reflects the green light beam from the third G light source 55G, and causes the red light beam from the second R light source 52R to be transmitted therethrough. The second reflection mirror 67 reflects the red light beam from the second R light source 52R to cause it to enter the second dichroic mirror 66.

The optical path of the red light beam from the second R light source 52R is converted by 90 degrees by the second reflection mirror 67, enters the second dichroic mirror 66, and is transmitted therethrough. The optical path of the green light beam of the third G light source 55G is converted by 90 degrees by the second dichroic mirror 66, and combined with the red light beam transmitted through the second dichroic mirror 66. The multiplexed light beam takes a second optical path 92. The multiplexed light beam enters the dichroic mirror 60, is reflected by the dichroic mirror 60, and enters the condenser lens 59. The light beam condensed by the condenser lens 59 enters the rod integrator 61.

In the third optical system group 83, the third dichroic mirror 68 reflects the blue light beam from the B light source 56B, and causes the green light beam from the first G light source 53G to be transmitted therethrough. The third reflection mirror 69 reflects the green light beam from the first G light source 53G to cause it to enter the third dichroic mirror 68.

The optical path of the green light beam of the first G light source 53G is converted by 90 degrees by the third reflection mirror 69, enters the third dichroic mirror 68, and is transmitted therethrough. The optical path of the blue light beam from the B light source 56B is converted by 90 degrees by the third dichroic mirror 68, and combined with the green light beam transmitted through the third dichroic mirror 68. The multiplexed light beam takes the third optical path 93. The multiplexed light beam enters the dichroic mirror 60, is reflected by the dichroic mirror 60, and enters the condenser lens 59. The light beam condensed by the condenser lens 59 enters the rod integrator 61.

By combining the light beams emitted from the R light sources 51R, 52R, the G light sources 53G, 54G, and 55G, and the B light source 56B, a white light beam can be generated. By controlling the output intensity of each color (each wavelength), white balance of an image and the amount of emitted light beams can be adjusted.

In the normal light observation, the multiplexed white light beam generated by the multiplexing unit 5B by combining the white light beam from the broadband light source and the red light beam, the green light beam, and the blue light beam from the narrow-band light source unit 5A is applied as the irradiation light beam 7 to the part 3 to be observed. By generating a white light beam using red, green, and blue laser light beams, and combining it with a white light beam from the broadband light source, the multiplexed white light beam can be made closer to sunlight, and the color rendering is improved.

In the special light observation, the broadband light source does not emit a white light beam, and the narrow-band light source unit 5A emits a laser light beam of a predetermined wavelength band corresponding to the special light observation.

In the special light observation, for example, by using the wavelength dependency of light absorption in the body tissue to use the blue light beam and the green light beam, which are light beams of a narrower band than the illumination light at the time of the normal light observation (i.e., white light beam), as the irradiation light beam, so-called narrow-band light observation (Narrow Band Imaging) in which a predetermined tissue such as a blood vessel in a mucosal surface layer is imaged with high contrast is performed.

Alternatively, in the special light observation, autofluorescence observation in which an image is obtained by fluorescence generated by applying an excitation light beam may be performed. For example, by using indocyanine green (ICG) to use two infrared light beams having different wavelength bands as irradiation light beams, infrared light observation in which a substance with absorbance change in the infrared light beam region is expressed in color may be performed.

Further, by using 5-aminolevulinic acid (ALA), the violet light beam may be applied as an excitation light beam, and fluorescence (red light beam) of protoporphyrin IX generated by metabolism of 5-ALA taken in a tumor cell and accumulated may be used as an observation light beam.

In the normal light/special light observation, similarly to the normal light observation, a multiplexed white light beam is applied to the part 3 to be observed. At this time, output of a laser light beam of a predetermined wavelength band from the narrow-band light source unit 5A is adjusted to, for example, the intensity suitable for autofluorescence observation. Accordingly, an image in which the normal light observation image and the special light observation image are superimposed can be obtained.

In each of the optical system groups 81 to 83, the light sources 54G, 55G, and 56B that emit laser light beams reflected by the dichroic mirrors 64, 66, and 68 correspond to the first laser light source in the corresponding group. The laser light beam emitted from each first laser light source corresponds to the first laser light beam.

In each of the optical system groups 81 to 83, the light sources 51R, 52R, and 53G that emit laser light beams reflected by the reflection mirrors 65, 67, and 69 correspond to the second laser light source in the corresponding group. The laser light beam emitted from each second laser light source corresponds to the second laser light beam, and the wavelength band thereof is different from that of the first laser light beam.

A laser group A including the light sources 54G, 55G, and 56B corresponding to the first laser light source and a laser group B including the light sources 51R, 52R, and 53G corresponding to the second laser light source are arranged to face each other with a mirror group including the plurality of mirrors 64 to 69 disposed therebetween. Regarding the above-mentioned Peltier device, at least two Peltier devices are provided, i.e., at least one Peltier device is provided in the laser group A and at least one Peltier device is provided in the laser group B.

In each of the optical system groups 81 to 83, the two laser light sources are arranged so that the laser light beam that is emitted from each laser light source belonging to the same optical system group and reaches the dichroic mirror or the reflection mirror has a parallel optical path and an opposite emission direction.

In each of the optical system groups 81 to 83, the mirrors and the laser light sources are arranged so that the laser light beam from each of the plurality of laser light sources belonging to the optical system group has a different emission direction and takes the same optical path by being combined by the dichroic mirror. Therefore, in each optical system group, the dichroic mirror and the reflection mirror are not parallel with each other, i.e., in the positional relationship of 90 degrees in this embodiment.

Since the two laser light sources are arranged so that the emission directions of laser light beams are opposed to each other as described above, intervals between the plurality of optical paths of the light beams that enter the condenser lens from each optical system group can be narrowed and the lens diameter of the condenser lens can be reduced. Further, since the laser light sources are arranged in this way, the length of the optical path can be reduced. Therefore, it is possible to reduce the size of the entire optical system of the light source apparatus.

Figure 7:
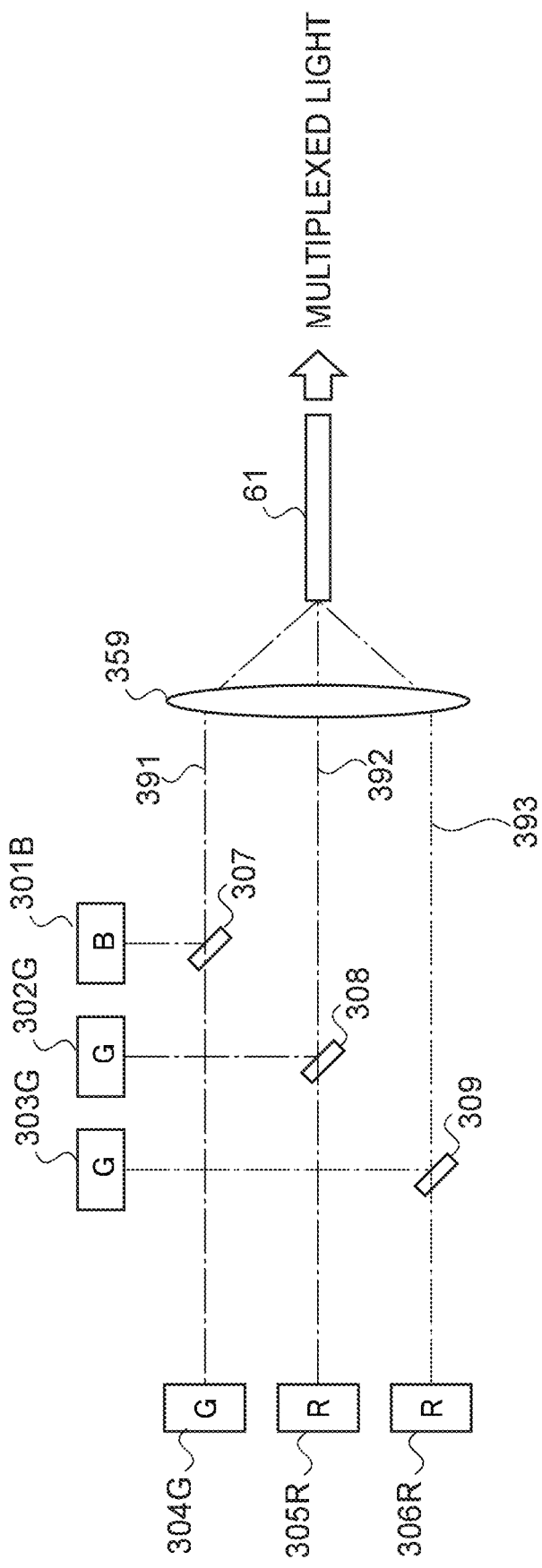
FIG. 7 is a partial diagram of a medical light source apparatus according to a comparative example, and is a diagram for describing arrangement of a red light source, a green light source, and a blue light source.
Figure 8:
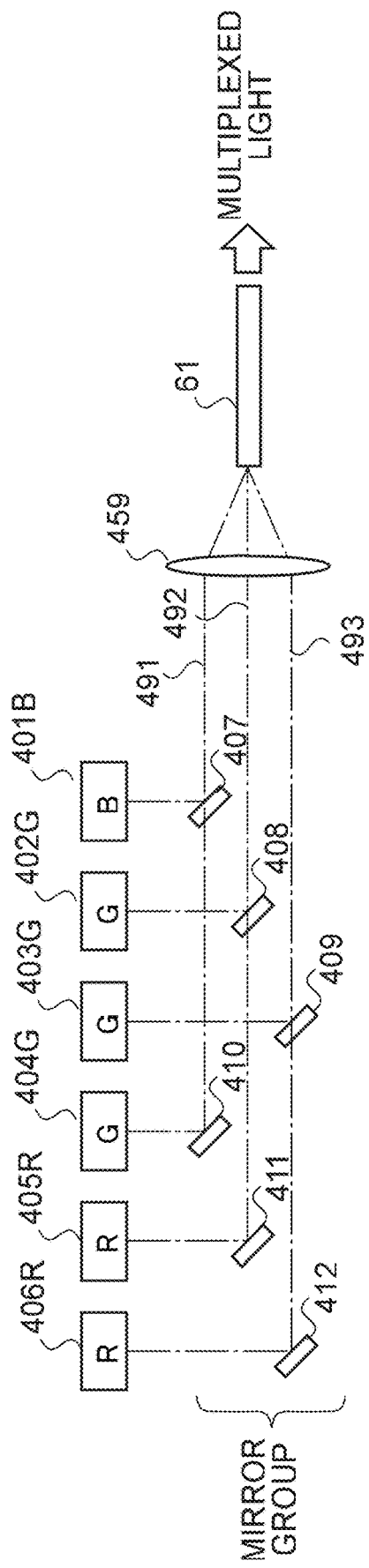
FIG. 8 is a partial diagram of a medical light source apparatus according to another comparative example, and is a diagram for describing arrangement of a red light source, a green light source, and a blue light source.

For example, as a comparative example, the reason why miniaturization can be performed will be described by taking arrangement shown in FIG. 7 and FIG. 8 as an example. FIG. 7 is a schematic diagram of the light source apparatus in which two R light sources, three G light sources, and one B light source are arranged. FIG. 8 is a schematic diagram of the light source apparatus in which two R light sources, three G light sources, and one B light source are arranged. Note that the same reference symbols are given to the same components as those in FIG. 3.

In the light source apparatus in FIG. 7 as a comparative example, a multiplexed light beam obtained by combining a blue light beam from a B light source 301B and a green light beam from a G light source 304G by a dichroic mirror 307 takes a first optical path 391, a multiplexed light beam obtained by combining a green light beam from a G light source 302G and a red light beam from an R light source 305R by a dichroic mirror 308 takes a second optical path 392, and a multiplexed light beam obtained by combining a green light beam from a G light source 303G and a red light beam from an R light source 306R by a dichroic mirror 309 takes a third optical path 393.

The light beam that takes the first to third optical paths 391 to 393 enters a condenser lens 359. In the embodiment of the comparative example shown in FIG. 7, the optical path direction of the laser light beam emitted from each of the G light source 304G, the R light source 305R, and the R light source 306R is not converted until it reaches the condenser lens 359.

Therefore, the arrangement intervals in the case where the light source of the G light source 304G, the light source of the R light source 305R, and the light source of the R light source 306R are arranged side by side are reflected in the optical path intervals of the first to third optical paths 391 to 393 as they are. Therefore, the optical path intervals of the first to third optical paths 391 to 393 are determined depending on the size of each light source, and the size of the condenser lens 359 is affected by the size of the light source.

In the light source apparatus in FIG. 8 as a comparative example, a green light beam that is emitted from a G light source 404G and reflected by a reflection mirror 410 enters a dichroic mirror 407 and is transmitted therethrough. A blue light beam from a B light source 401B is reflected by the dichroic mirror 407 and combined with the green light beam transmitted through the dichroic mirror 407. The multiplexed light beam takes a first optical path 491.

A red light beam that is emitted from R light source 405R and reflected by a reflection mirror 411 enters a dichroic mirror 408 and is transmitted therethrough. A green light beam from a G light source 402G is reflected by the dichroic mirror 408 and combined with the red light beam transmitted through the dichroic mirror 407. The multiplexed light beam takes a second optical path 492.

A red light beam that is emitted from an R light source 406R and reflected by a reflection mirror 412 enters a dichroic mirror 409 and is transmitted therethrough. A green light beam from a G light source 403G is reflected by the dichroic mirror 409 and combined with the red light beam transmitted through the dichroic mirror 409. The multiplexed light beam takes a third optical path 493.

The light beam that takes the first to third optical paths 491 to 493 enters a condenser lens 459. In the embodiment shown in FIG. 8, since the laser light sources are arranged side by side on one side with respect to the mirror group, the dichroic mirror and the reflection mirror corresponding to each optical path are positioned in parallel with each other.

In the embodiment of the comparative example shown in FIG. 8, the mirrors and the laser light sources are arranged so that the optical paths through which a plurality of laser light beams emitted from the laser light sources reach the dichroic mirror or the reflection mirror and the optical path through which the light beam obtained by combining the plurality of laser light beams enters the condenser lens are different by 90 degrees. Therefore, the effective diameter of the condenser lens 459 can be reduced without being affected by the size of the laser light source unit.

However, in the comparative example shown in FIG. 8, since the plurality of light sources are arranged side by side in the same column, the optical path length of each of the G light source 404G, the R light source 405R, and the R light source 406R is longer than that in this embodiment shown in FIG. 3. Therefore, although the laser light beam is excellent in directivity, it diffracts due to propagation and the collimation property decreases. Therefore, as the optical path length is longer, the decrease in collimation property is more remarkable.

Further, in the case where the optical path length differs in each laser light beam, it is difficult to balance the condensed state of all the laser light beams when being condensed by the same condenser lens 459. Therefore, it is difficult to efficiently couple the laser light beam to the rod integrator 61, and vignetting occurs on the incident surface.

In contrast to these comparative examples, in this embodiment, in each of the optical system groups 81 to 83, the mirrors and the laser light sources are arranged so that the optical paths through which the laser light beams emitted from the plurality of laser light sources belonging to the corresponding optical system group reach the dichroic mirror or the reflection mirror and the optical path through which the light beam obtained by combining the plurality of laser light beams by the dichroic mirror enters the condenser lens are different by 90 degrees as shown in FIG. 3. Further, in each of the optical system groups 81 to 83, the laser light sources are arranged so that the emission directions of the laser light beams emitted from the two laser light sources are opposed to each other.

As described above, in this embodiment, since the laser light beams from the plurality of laser light sources enter the condenser lens with the optical path directions thereof being converted unlike the embodiment shown in FIG. 7, the optical path intervals between the first to third optical paths 91 to 93 of the light beams that enter the condenser lens 59 are not affected by the size of the light source unit and can be narrowed.

Further, in this embodiment, the emission directions of the laser light beams emitted from the two laser light sources in each optical system group are opposed to each other, and the optical path lengths of the two laser light beams constituting each group are substantially the same.

Accordingly, it is possible to shorten the length of the entire optical path and prevent the collimation property of the laser light beam from decreasing. Further, since the optical path lengths are substantially the same, it is easy to balance the condensed state of both the laser light beams by the same condenser lens 59 and it is possible to efficiently couple both the laser light beams to the rod integrator 61.

As described above, in this embodiment, since the effective diameter of the condenser lens 59 can be reduced and the optical path lengths can be shortened, it is possible to reduce the size of the entire optical system and miniaturize the light source apparatus 5. Further, by shortening the optical path lengths and making the optical path lengths substantially the same, it is possible to efficiently couple the laser light beam to the rod integrator 61.

Further, in each of the optical system groups 81 to 83, the wavelength of the first laser light beam emitted from the first laser light source is shorter than that of the second laser light beam emitted from the second laser light source. That is, in the first optical system group 81, the wavelength of the green light beam emitted from the second G light source 54G is shorter than that of the red light beam emitted from the first R light source. In the second optical system group 82, the wavelength of the green light beam emitted from the third G light source 55G is shorter than that of the red light beam emitted from the second R light source 52R. In the third optical system group 83, the blue light beam emitted from the B light source 56B is shorter than that of the green light beam emitted from the first G light source 53G.

By arranging the dichroic mirrors 64, 66, and 68 so that the dichroic mirrors cause the laser light beam having a relatively longer wavelength to be transmitted therethrough and reflect the laser light beam having a relatively shorter wavelength in each of the optical system groups 81 to 83 including the plurality of laser light sources that emit laser light beams having different wavelength bands as described above, the optical characteristics of the dichroic mirrors are prevented from being deteriorated with time. Accordingly, the color of the illumination light emitted from the light source apparatus 5 can be stabilized for a long time, and the light source apparatus 5 having high reliability can be obtained. In particular, in the case of using a light source apparatus in medical applications, there is a high possibility that it is difficult to perform appropriate diagnosis or treatment, by deviation of the color due to attenuation of a part of illumination light of the laser light source. Therefore, the stability of color of illumination light is important, and is highly demanded by medical personnel. With the light source apparatus 5 according to this embodiment of the present technology, since the color of illumination light can be stabilized for a long time, it is possible to reliably perform appropriate diagnosis or treatment.

Figure 4:
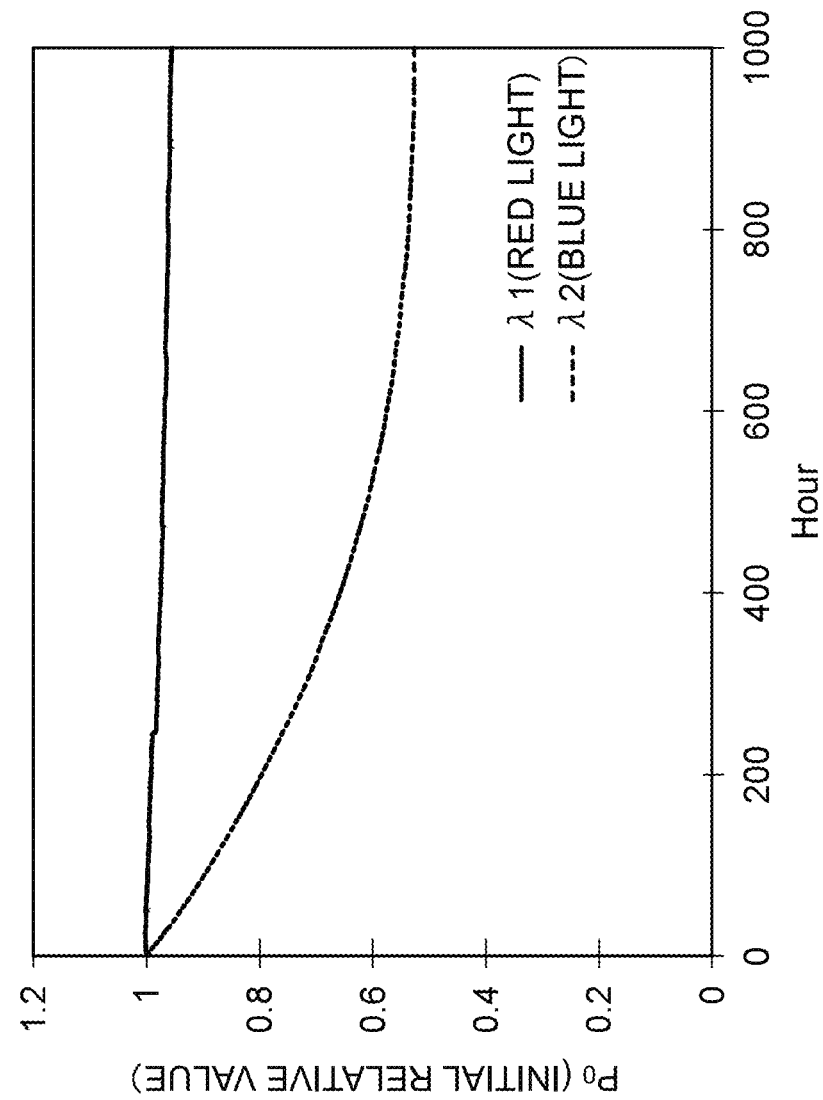
FIG. 4 is a diagram showing the change with time in the transmittance characteristics of the dichroic mirror due to the difference in wavelength of a light beam to be applied.
Figure 4:
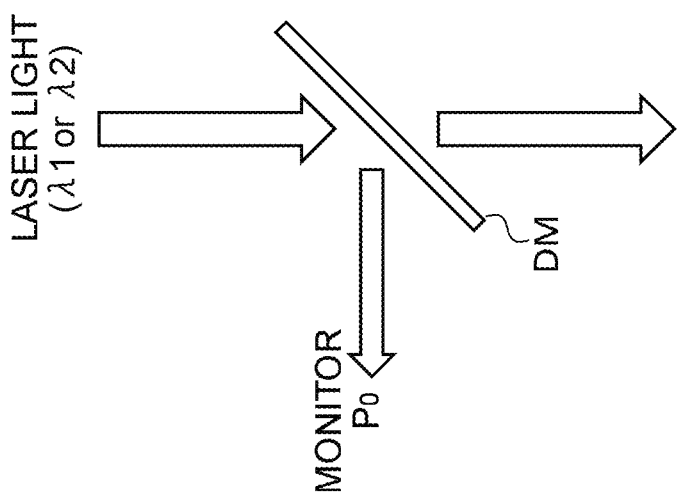

FIG. 4 is a diagram showing the change with time in the light beam reflection characteristics of the dichroic mirror when each of the red light beam and the blue light beam is applied to the dichroic mirror. In FIG. 4, the horizontal axis represents time and the vertical axis represents the relative value of the amount of reflected light beams based on the initial amount of reflected light beams. In FIG. 4, the solid line indicates the red light beam, and the broken line indicates the blue light beam.

As shown in FIG. 4, the change with time in the optical characteristics of the light beam having a relatively short wavelength is larger than that of the light beam having a relatively long wavelength. As described above, a dielectric multilayer film of the dichroic mirror configured by forming the dielectric multilayer film by a vacuum deposition method or the like is liable to be deteriorated by the light beam having a shorter wavelength as compared with the case of the light beam having a long wavelength.

For this reason, in the case where a plurality of laser light beams having different wavelength bands enter a dichroic mirror, it is favorable to dispose the dichroic mirror so that it causes the laser light beam having a relatively longer wavelength to be transmitted therethrough and reflects the laser light beam that has a relatively shorter wavelength and energy larger than that of the laser light beam having a long wavelength. Accordingly, it is possible to prevent the optical characteristics of the dichroic mirror from being deteriorated with time.

The first optical path 91 taken by the multiplexed light beam generated in the first optical system group 81, the second optical path 92 taken by the multiplexed light beam generated in the second optical system group 82, and the third optical path 93 taken by the multiplexed light beam generated in the third optical system group 83 are different from each other.

The light beam on the second optical path 92 enters the substantially center part of the dichroic mirror 60, and then enters the substantially center part of the condenser lens 59. On paper of FIG. 3, the light beam on the first optical path 91 enters the lower part of the dichroic mirror 60, and then enters the lower part of the condenser lens 59. The light beam of the third optical path 93 enters the upper part of the dichroic mirror 60, and then enters the upper part of the condenser lens 59. In this embodiment, the first optical path 91 and the third optical path 93 are each the optical path located on the outermost side when the light beam thereon enters the condenser lens 59.

In this embodiment, the multiplexed light beams taking the plurality of optical paths 91 to 93 enter the same condenser lens 59. In the case where a plurality of multiplexed light beams on different optical paths enter a condenser lens as described above, it is desired to arrange laser light sources and mirrors so that the light beam on each of the first optical path 91 and the third optical path 93 located on the outermost side includes at least one red light beam, at least one blue light beam, and at least one green light beam. Accordingly, in the case of using, as illumination light, a white light beam obtained by combining the red light beam, the blue light beam, and the green light beam, it is possible to obtain white illumination light with suppressed color unevenness in the irradiation area.

The red light beam, the green light beam, and the blue light beam that are condensed by the condenser lens 59 and enter the rod integrator 61 pass through the rod integrator 61, and are then emitted with the illumination distribution of the incident light beam being made uniform.

As described above, in the rod integrator 61, although the light beam is emitted with the illumination distribution of the light beam being made uniform, it is emitted from the rod integrator 61 while keeping the incident angle component at the time entering the rod integrator 61.

Therefore, for example, in the case where all of the red light beam, the green light beam, and the blue light beam are not present in the optical path located on the outermost side out of the plurality of optical paths, even when generating a white light beam using the red light beam, the green light beam, and the blue light beam, the center part of the irradiation area of the light beam emitted from the rod integrator 61 becomes white, but the periphery of the center part does not become white, thereby providing illumination light with color unevenness. This is because the emission point size and the radiation angle differ for the laser light beam of each color and the periphery of the center part of the irradiation area of the light beam does not become white due to a difference in radiation angle of the laser light beam of each color.

In this embodiment, in the case where light beams on a plurality of different optical paths are condensed by a condenser lens and enter a rod integrator, laser light sources and mirrors are arranged so that the light beam on the optical path located on the outermost side out of the light beams that enter the condenser lens includes at least one red light beam, at least one blue light beam, and at least one green light beam. Accordingly, the maximum incident angles become uniform. Therefore, it is possible to make the periphery of the center part of the irradiation area of the illumination light formed of the light beam emitted from the rod integrator 61 white, and the illumination light with suppressed color unevenness in the irradiation area can be obtained.

In this embodiment, since one B light source is provided, the light beam on the optical path located on the outermost side out of the plurality of optical paths includes a blue light beam from the viewpoint of suppressing the above-mentioned color unevenness.

Further, in this embodiment, although the light beams emitted from the IR light source 57IR and the V light source 58V used for the special light observation are included in the optical paths located on the outermost side out of the plurality of optical paths, the present technology is not limited to this, and the light beams may be included in the second optical path 92 at the center.

However, in the case of providing a function of superimposing the normal light observation image and the 5-ALA fluorescence image, or the normal light observation image and the ICG fluorescence image(pseudo-color) on one screen for display, it is favorable to make the radiation angle uniform by using all colors of the red light beam, the green light beam, the blue light beam, the violet light beam, and the infrared light beam, and it is favorable that the light beams emitted from the IR light source 57IR and the V light source 58V are included in the optical paths located on the outermost side out of the plurality of optical paths.

On the assumption that the violet light beam or infrared light beam which is an excitation light beam passes through the central optical path out of the three optical paths, since the radiation angles of the violet light beam and the infrared light beam are narrower than those of the red light beam, the green light beam, and the blue light beam, the imaging range of the fluorescence image (special light observation image) obtained by application of an excitation light beam is narrower than that of the normal light observation image. Therefore, in the image obtained by superimposing the normal light observation image and the special light observation such as the 5-ALA fluorescence image and the ICG fluorescence image, the fluorescence image is obtained only for the center part, which is inconvenient for an observer such as a doctor.

Therefore, it is favorable that the light beams emitted from the IR light source 57IR and the V light source 58V are included in the optical paths located on the outermost side out of the plurality of optical paths. Accordingly, it is possible to make the radiation angle uniform in all colors of the red light beam, the green light beam, the blue light beam, the violet light beam, and the infrared light beam, make the imaging ranges of the normal light observation image and the special light observation image substantially the same, and observe a superimposed image in a wide range.

As described above, in this embodiment, it is possible to reduce the size of the entire optical system even in the case where a plurality of laser light sources are provided.

Other Embodiments

In the above-mentioned embodiment, two R light sources, three G light sources, and one B light source are provided. However, the number of light sources are not limited thereto, and the output power of each light source and the number of light sources may be arbitrarily set so that a light beam of a desired color and desired power is emitted from the light source apparatus 5. Further, also the arrangement of the light sources and the type of the laser light source to be selected are not limited to those in the above-mentioned embodiment. Hereinafter, as other embodiments, second and third embodiments will be described.

Note that although the IR light source and the V light source have been taken as examples of a light source used for the special light observation other than the R, G, and B light sources in the above-mentioned embodiment, only one of them may be provided, and it does not necessarily need to provide the IR light source and the V light source.

Hereinafter, although the second embodiment and the third embodiment will be respectively described with reference to FIG. 5 and FIG. 6, the present technology is not limited to the configuration shown in FIG. 5 and FIG. 6 as long as the light source apparatus includes at least one optical system group.

This optical system group only needs to include two laser light sources from which laser light beams having different wavelength bands are emitted, a dichroic mirror that reflects the light beam from one laser light source, causes the light beam from the other laser light source to be transmitted therethrough, and combines the laser light beams, and a reflection mirror that reflects the light beam from the other laser light source to cause it to enter the dichroic mirror, and the dichroic mirror and the reflection mirror only need to be arranged so that they are not parallel with each other.

Figure 5:
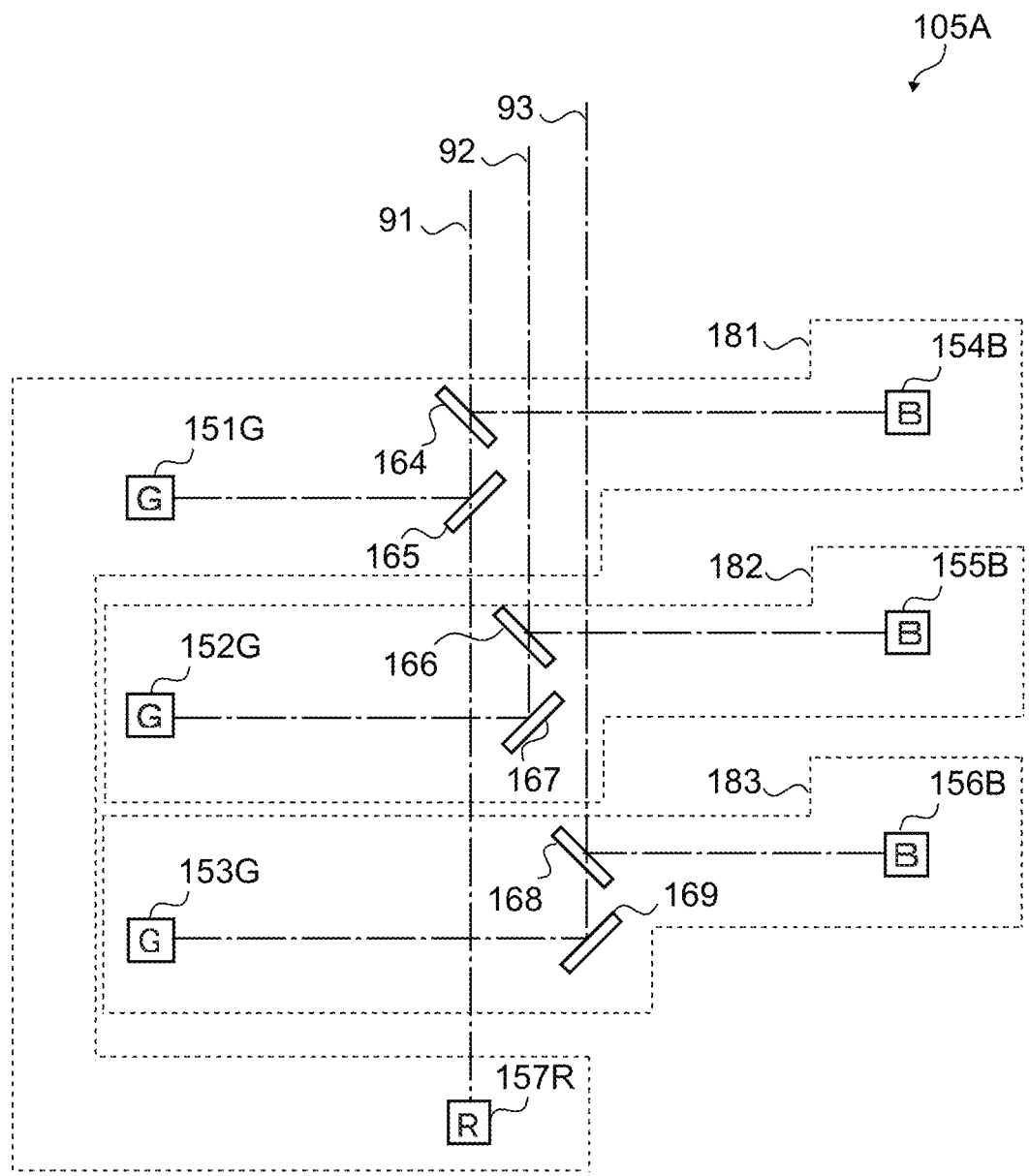
FIG. 5 is a partial diagram of a medical light source apparatus according to a second embodiment, and is a diagram for describing arrangement of a red light source, a green light source, and a blue light source.
Figure 6:
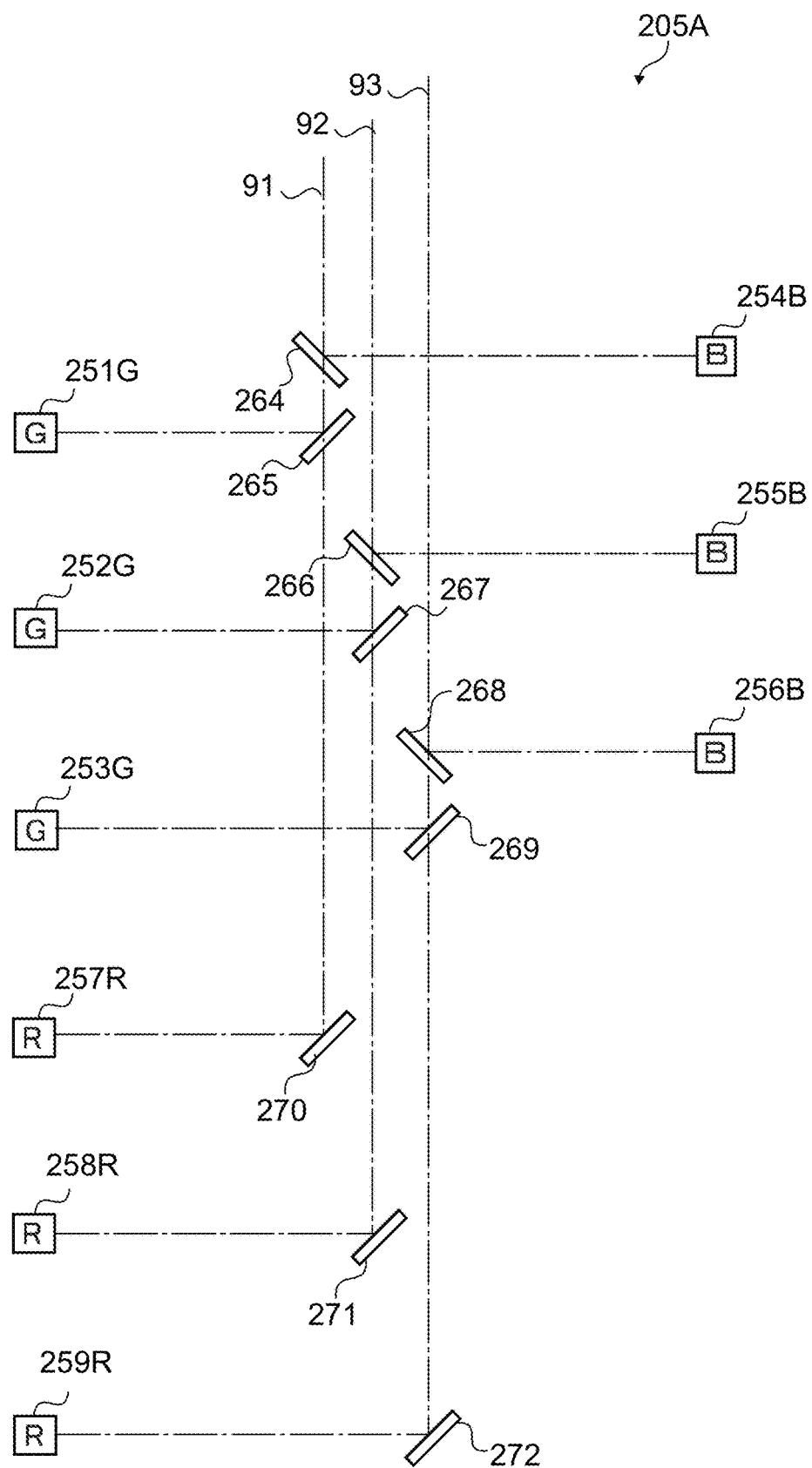
FIG. 6 is a partial diagram of a medical light source apparatus according to a third embodiment, and is a diagram for describing arrangement of a red light source, a green light source, and a blue light source.

Also, in the embodiments shown in FIG. 5 and FIG. 6, in each optical system group, the dichroic mirror reflects the laser light beam from one laser light source and converts the optical path by 90 degrees, and the reflection mirror reflects the laser light beam from the other laser light source and converts the optical path by 90 degrees. The dichroic mirror and the reflection mirror are arranged in the positional relationship of 90 degrees.

FIG. 5 and FIG. 6 are respectively partial diagrams of a narrow-band light source units 105A and 205A, and only arrangement of the R light source, G light source, and B light source is illustrated. Illustration of the dichroic mirror 60, the condenser lens 59, the rod integrator 61, the IR light source 57IR, the V light source 58V, the collimating lenses 77 and 78, and the collimating lenses of each optical system group will be omitted, and description thereof will be omitted in some cases. Further, the same components as those in the first embodiment will be denoted by the same reference symbols, and description thereof will be omitted in some cases.

Second Embodiment

FIG. 5 is a partial diagram of the narrow-band light source unit 105A of the light source apparatus according to this embodiment. In this embodiment, a case where one R light source, three G light sources, and three B light sources are provided will be shown.

The narrow-band light source unit 105A includes a first optical system group 181, a second optical system group 182, and a third optical system group 183. Only the first optical system group 181 includes three light sources. The second and third optical system groups 182 and 183 each include two light sources.

The first optical system group 181 includes an R light source 157R, a first G light source 151G, a first B light source 154B, a first dichroic mirror 164, and a first reflection mirror 165. The first dichroic mirror 164 reflects the blue light beam from the first B light source 154B, and causes the green light beam from the first G light source 151G and the red light beam from the R light source 157R to be transmitted therethrough.

The first reflection mirror 165 functions as a dichroic mirror that reflects the green light beam from the first G light source 151G and causes the red light beam from the R light source 157R to be transmitted therethrough. The optical path of the green light beam is converted by 90 degrees by the first reflection mirror 165, and the green light beam is combined with the red light beam and enters the first dichroic mirror 164. The optical path of the blue light beam is converted by 90 degrees by the first dichroic mirror 164, and the blue light beam is combined with the red light beam and the green light beam. The obtained multiplexed light beam takes the first optical path 91.

The second optical system group 182 includes a second G light source 152G, a second B light source 155B, a second dichroic mirror 166, and a second reflection mirror 167. The second dichroic mirror 166 reflects the blue light beam from the second B light source 155B, and causes the green light beam from the second G light source 152G to be transmitted therethrough. The second reflection mirror 167 reflects the green light beam from the second G light source 152G.

The optical path of the green light beam is converted by 90 degrees by the second reflection mirror 167, and the green light beam enters the second dichroic mirror 166. The optical path of the blue light beam is converted by 90 degrees by the second dichroic mirror 166, and the blue light beam is combined with the green light beam. The obtained multiplexed light beam takes the second optical path 92.

The third optical system group 183 includes a third G light source 153G, a third B light source 156B, a third dichroic mirror 168, and a third reflection mirror 169. The third dichroic mirror 168 reflects the blue light beam from the third B light source 156B, and causes the green light beam from the third G light source 153G to be transmitted therethrough. The third reflection mirror 169 reflects the green light beam from the third G light source 153G.

The optical path of the green light beam is converted by 90 degrees by the third reflection mirror 169, and the green light beam enters the third dichroic mirror 168. The optical path of the blue light beam is converted by 90 degrees by the third dichroic mirror 168, and combined with the green light beam. The obtained multiplexed light beam takes the third optical path 93.

In the optical system group 181 (182, 183), the G light source 151G (152G, 153G) and the B light source 154B (155B, 156B) are arranged so that the emission directions of the laser light beams therefrom are opposed to each other in parallel and differ by 180 degrees, similarly to the two laser light sources belonging to the same optical system in the first embodiment.

Further, in each of the optical system groups 181 to 183, the mirrors and the laser light sources are arranged so that the laser light beams from the plurality of laser light sources opposed to each other, which belong to the optical system group, are combined by the dichroic mirror and take the same optical path. In each optical system group, the dichroic mirror and the reflection mirror are not parallel with each other, and arranged so that the angle between the two mirrors is 90 degrees in this embodiment.

In this embodiment, the direction of the optical path of the red light beam emitted from the R light source 157R is not converted halfway, and the optical path finally takes the first optical path 91. However, since only one R light source 157R1 emits the light beam that takes such an optical path, there is substantially no influence on the selection of the size of the condenser lens.

Also, in this embodiment, the intervals between the plurality of optical paths of the light beams that enter the condenser lens from each optical system group can be narrowed, and the effective diameter of the condenser lens can be reduced. Further, the entire length of the optical path of the laser light beam can be shortened. Therefore, it is possible to reduce the size of the light source apparatus, and prevent the collimation property of the laser light beam from decreasing.

Further, in each optical system group, it is possible to make the optical path lengths of the laser light beams from the two laser light sources that emit the laser light beam whose emission directions are opposed to each other substantially the same, and efficiently couple both the laser light beams to the rod integrator.

Further, in the case where laser light sources that emit laser light beams having three different wavelength bands are used for the optical system group as in the first optical system group in this embodiment, it is favorable that laser light beam having a relatively longer wavelength is transmitted through the first dichroic mirror 164 and the first reflection mirror 165 that functions as the dichroic mirror, and laser light beam having a relatively shorter wavelength is reflected by the mirrors. Accordingly, it is possible to prevent the optical characteristics of the mirrors from being deteriorated with time, and obtain illumination light that is stable for a long time.

Third Embodiment

FIG. 6 is a partial diagram of the narrow-band light source unit 205A of the light source apparatus in this embodiment. In this embodiment, a case where three R light sources, three G light sources, and three B light sources are provided will be shown.

The narrow-band light source unit 205A includes first to third optical system groups. Each of the optical system groups includes three light sources of an R light source, a G light source, and a B light source.

The first optical system group includes a first R light source 257R, a first G light source 251G, a first B light source 254B, a first dichroic mirror 264, a first reflection mirror 265, and a first reflection mirror 270 for the red color.

The first dichroic mirror 264 reflects the blue light beam from the first B light source 254B, and causes the green light beam from the first G light source 251G and the red light beam from the first R light source 257R to be transmitted therethrough.

The first reflection mirror 265 functions as a dichroic mirror that reflects the green light beam from the first G light source 251G, and causes the red light beam from the first R light source 257R to be transmitted therethrough.

The first reflection mirror 270 for the red color reflects the red light beam from the first R light source 257R.

The optical path of the red light beam is converted by 90 degrees by the first reflection mirror 270 for the red color, and the red light beam enters the first reflection mirror 265. The optical path of the green light beam is converted by 90 degrees by the first reflection mirror 265, and the green light beam is combined with the red light beam to enter the first dichroic mirror 264. The optical path of the blue light beam is converted by 90 degrees by the first dichroic mirror 264, and the blue light beam is combined with the red light beam and the green light beam. The obtained multiplexed light beam takes the first optical path 91.

The second optical system group includes a second R light source 258R, a second G light source 252G, a second B light source 255B, a second dichroic mirror 266, a second reflection mirror 267, and a second reflection mirror 271 for the red color.

The second dichroic mirror 266 reflects the blue light beam from the second B light source 255B, and causes the green light beam from the second G light source 252G and the red light beam from the second R light source 258R to be transmitted therethrough.

The second reflection mirror 267 functions as a dichroic mirror that reflects the green light beam from the second G light source 252G, and causes the red light beam from the second R light source 258R to be transmitted therethrough.

The second reflection mirror 271 for the red color reflects the red light beam from the second R light source 258R.

The optical path of the red light beam is converted by 90 degrees by the second reflection mirror 271 for the red color, and the red light beam enters the second reflection mirror 267. The optical path of the green light beam is converted by 90 degrees by the second reflection mirror 267, and the green light beam is combined with the red light beam to enter the second dichroic mirror 266. The optical path of the blue light beam is converted by 90 degrees by the second dichroic mirror 266, and the blue light beam is combined with the red light beam and the green light beam. The obtained multiplexed light beam takes the second optical path 92.

The third optical system group includes a third R light source 259R, a third G light source 253G, a third B light source 256B, a third dichroic mirror 268, a third reflection mirror 269, and a third reflection mirror 272 for the red color.

The third dichroic mirror 268 reflects the blue light beam from the third B light source 256B, and causes the green light beam from the third G light source 253G and the red light beam from the third R light source 259R to be transmitted therethrough.

The third reflection mirror 269 functions as a dichroic mirror that reflects the green light beam from the third G light source 253G, and causes the red light beam from the third R light source 259R to be transmitted therethrough.

The third reflection mirror 272 for the red color reflects the red light beam from the third R light source 259R.

The optical path of the red light beam is converted by 90 degrees by the third reflection mirror 272 for the red color, and the red light beam enters the third reflection mirror 269. The optical path of the green light beam is converted by 90 degrees by the third reflection mirror 269, and combined with the red light beam to enter the third dichroic mirror 268. The optical path of the blue light beam is converted by 90 degrees by the third dichroic mirror 268, and the blue light beam is combined with the red light beam and the green light beam. The obtained multiplexed light beam takes the third optical path 93.

In each optical system group, the laser light sources and the mirrors are arranged so that the optical paths of the laser light beams that are emitted from the three laser light sources and reach the dichroic mirror, the reflection mirror, and the reflection mirror for the red are in parallel with each other.

Further, in each optical system group, the directions of the optical paths of the laser light beams that are emitted from the three laser light sources and reach the dichroic mirror, the reflection mirror, and the reflection mirror for the red and the direction of each of the optical paths 91 to 93 taken by the multiplexed light beam combined by the dichroic mirror of each optical system group differ by 90 degrees.

Further, the dichroic mirror and the reflection mirror in each optical system group are arranged so that the angle between them is 90 degrees.

As described above, each optical system group may include three laser light sources. Also, in this embodiment, intervals between the plurality of optical paths of the light beams that enter the condenser lens from each optical system group can be narrowed and the effective diameter of the condenser lens can be reduced. It is possible to reduce the size of the light source apparatus.

The embodiments of the present technology are not limited to the above-mentioned embodiments, and various modifications can be made without departing from the essence of the present technology.

For example, although monitor observation by the camera 4 can be performed in the above-mentioned endoscope system 1, the medical light source apparatus may be connected to a microscope and applied to surgical microscope for brain surgery or the like, so that illumination light suitable for macroscopic observation can be obtained.

Further, although the case where the number of optical paths of light beams that enter the condenser lens is three has been described as an example in the above-mentioned embodiments, the present technology is not limited thereto, and the number of optical paths only needs to be one or more and may be, for example, two, four, or five.

For example, in the case where one optical system group including three laser light sources of an R light source, a G light source, and a B light source is provided and one optical path is generated by this optical system group, the B light source and the G light source are arranged so that the emission directions of laser light beams are opposed to each other as in the first optical system group 181 of the second embodiment.

With such a configuration, for example, it is possible to shorten the optical path length of the light source as compared with the case where all the laser light sources are arranged on one side with respect to the mirror group as in the comparative example shown in FIG. 8. Therefore, it is possible to make the entire optical system small and reduce the size of the light source apparatus. Note that in the case where the number of optical paths is one, the size of the condenser lens can be arbitrarily set.

Further, in the first embodiment, although the example in which the laser group A and the laser group B are arranged on the same inner bottom surface of the enclosure 94 has been described, the present technology is not limited thereto. For example, the laser group B may be disposed on the inner upper surface opposite to the inner bottom surface of the enclosure so that the emission directions of laser light beams emitted from the laser group B are directed from the inner upper surface of the enclosure to the inner bottom surface. In this case, the reflection mirror is disposed so as to reflect the laser light beam from the laser group B and causes it to enter the dichroic mirror.

In such a configuration, it only needs to dispose cooling units at two places of the bottom surface and the upper surface of the enclosure. Note that by disposing each laser light source on the same surface of the enclosure as in the first to third embodiments, it only needs to cool only from one surface side of the enclosure. Therefore, it is possible to reduce the number of cooling units and achieve further miniaturization.

Further, in the above-mentioned embodiments, the optical path of the laser light beams emitted from the two laser light sources is converted by 90 degrees by the dichroic mirror or the reflection mirror in each optical system group. However, the conversion angle is not limited to 90 degrees. The incident angle of the laser light beam to the mirror may be set to one other than 45 degrees within the range in which the optical characteristics by the light beam incident angle of each mirror do not change, and the conversion angle of the optical path may be one other than 90 degrees, e.g., 80 degrees.

Further, although the example in which a light source (a laser light source) including a semiconductor laser device that is a monochromatic light emission device is used as a light source has been described in the above-mentioned embodiments, a light source (LED light source) including an LED (Light Emitting Diode) that is a monochromatic light emission device may be used.

Also in the case of using the LED light source, similarly to the case of using the laser light source, by arranging a first LED light source and a second LED light source so that the emission directions of a first light beam (corresponding to the first laser light beam in the case of using the laser light source) and a second light beam to be emitted are opposed to each other, it is possible to reduce the size of the entire optical apparatus.

Note that the first light beam (second light beam) emitted from the first LED light source (second LED light source) corresponds to the first laser light beam (second laser light beam) in the case of using the first laser light source (second laser light source).

Further, although the case where the first laser light source and the second laser light source whose emission directions of light beams are opposed each other each include any one of the R light source, the G light source, and the B light source has been described in the above-mentioned embodiments, they may each include a special light source such as an IR light source and a V light source.

Further, although the dichroic mirror has been described as an example of the multiplexing member generating the multiplexed light beam of the first laser light beam and the second laser light beam in the above-mentioned embodiments, a prism may be used.

Figure 9:
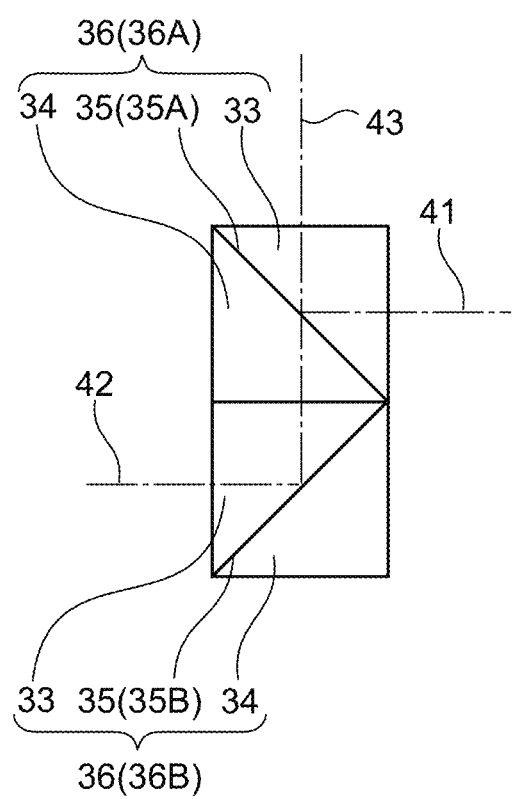
FIG. 9 is a schematic diagram of a multiplexing member using a prism.

For example, as shown in FIG. 9, a dichroic mirror film 35 may be applied to the slope of two 45° right angle prisms 33 and 34, and a beam splitter 36 having a rectangular parallelepiped shape obtained by bonding them can be used as a multiplexing member. The dichroic mirror film 35 reflects the light beam having a specific wavelength and causes the light beam having other wavelengths to be transmitted therethrough.

As shown in FIG. 9, an optical member obtained by combining two beam splitters of the beam splitters 36A and 36B each having a rectangular parallelepiped shape may be replaced with a dichroic mirror and a reflection mirror constituting a part of one optical group to configure a medical light source apparatus.

In the optical member shown in FIG. 9, the dichroic mirror film 35A of the beam splitter 36A and the dichroic mirror film 35B of the beam splitter 36B are positioned to not be parallel with each other. In other words, they are positioned so that the bonding surfaces of the beam splitters 36A and 36B are not parallel with each other.

The optical member obtained by combining the two beam splitters 36A and 36B shown in FIG. 9 is an optical member that combines the first laser light beam and the second laser light beam whose emission directions are different from each other. That is, as shown in FIG. 9, a second laser light beam 42 is reflected by the dichroic mirror film 35B of the beam splitter 36B and enters the beam splitter 36A. In the beam splitter 36A, the second laser light beam 42 that enters the beam splitter 36A and is transmitted therethrough and a first laser light beam 41 that enters the beam splitter 36A and is reflected by the dichroic mirror film 35A are combined. A multiplexed light beam 43 generated by the beam splitter 36B is emitted from the beam splitter 36A.

By using an optical member obtained by two beam splitters of the beam splitters 36A and 36B each having a rectangular parallelepiped shape as described above, it is possible to reduce the size of the optical member. By configuring a medical light source apparatus using such an optical member, it is possible to reduce the size of the light source apparatus.

Further, by providing a dielectric multilayer film that causes one of P polarized light and S polarized light and reflects the other instead of the dichroic mirror film 35 to configure a beam splitter as a multiplexing member, the first laser light beam and the second laser light beam may be polarized and combined by the beam splitter.

As described above, by using a multiplexing member that performs polarization and multiplex instead of the dichroic mirror, a first laser light source and a second laser light source arranged so that emission directions of laser light beams to be emitted therefrom are opposed to each other can be light sources of the same color, and the design range can be expanded.

Further, the special light observation image and normal light observation image in the above-mentioned special light observation may be obtained by performing imaging while switching the special light and the normal light in time division. Alternatively, the visible light observation image and the fluorescence observation image may be obtained in real time.

In the imaging performed while switching the special light and the normal light in time division, by applying the special light and the normal light to the observation target in time division and controlling the driving of the imaging device of the camera in synchronization with the application timing, it is possible to capture a special light observation image and a normal light observation image in time division.

Figure 21:
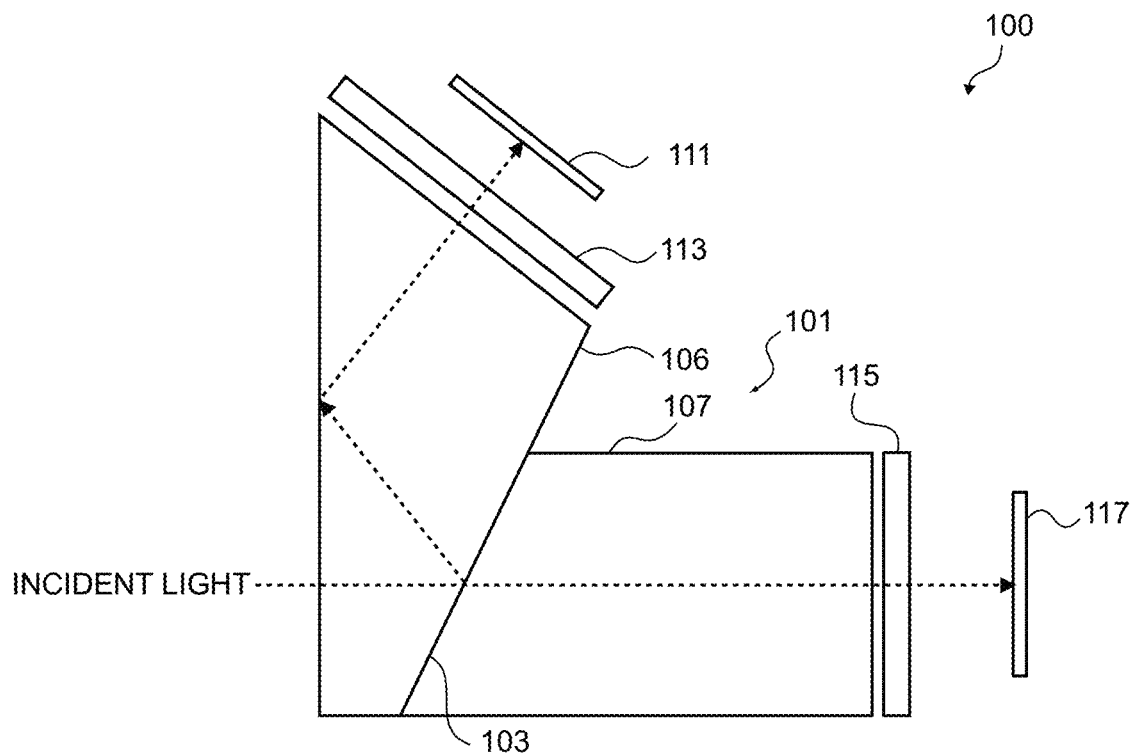
FIG. 21 is an explanatory diagram schematically showing an example of a configuration of an optical unit of an imaging apparatus capable of simultaneously capturing a visible light image and a fluorescence observation image.

The visible light image and fluorescence image of the part 3 to be observed irradiated with light from the medical light source apparatus 5 can be simultaneously captured by using, for example, an the optical unit 100 shown in FIG. 21.

The optical unit 100 shown in FIG. 21 includes a color separation prism 101, an imaging device 111 for imaging a visible light image, an infrared cut filter 113, a band-path filter 115, and an imaging device 117 for imaging a fluorescence image.

The color separation prism 101 is configured by joining a first prism 106 and a second prism 107 via a dichroic film 103. The color separation prism 101 is an optical member that separates the light that has entered the optical unit 100 into a light beam belonging to a visible light wavelength band and a light beam belonging to a fluorescence light wavelength band by the dichroic film 103.

The first prism 106 is a prism that functions as an optical path for visible light. The light beam belonging to a visible light wavelength band and the light beam belonging to a fluorescence light wavelength band (i.e., incident light beam) enter the optical path, and the light beam belonging to a visible light wavelength band is guided by the optical path.

The second prism 107 is a prism that functions as an optical path for fluorescence light. The light beam belonging to a fluorescence light wavelength band is guided by the optical path.

The light that has entered the first prism 106 goes straight in the first prism 106, and is separated into a light beam belonging to a visible light wavelength band and a light beam belonging to a fluorescence light wavelength band by the dichroic film 103.

The light beam belonging to a visible light wavelength band is reflected by the dichroic film 103, and guided in the first prism 106. The visible light beam transmitted therethrough the first prism 106 is guided to the imaging device 111 for imaging a visible light image. At this time, the infrared cut filter 113 may be provided between the first prism 106 and the imaging device 111 for imaging a visible light image.

A visible light image is generated by forming an image of the light belonging to a visible light wavelength band on the imaging device 111 for imaging a visible light image.

Meanwhile, the light belonging to a fluorescence light wavelength band transmitted through the dichroic film 103 enters the second prism 107, goes straight in the second prism 107, and is transmitted through the second prism 107 to the outside. The light belonging to a fluorescence light wavelength band transmitted through the second prism 107 enters the band-path filter 115.

The band-path filter 115 reflects light beams other than the light of a fluorescence light wavelength band, and causes only the light of a fluorescence light wavelength band to be transmitted therethrough. A fluorescence light image is generated by forming an image of the light of a fluorescence light wavelength band transmitted through the band-path filter 115 on the imaging device 117 for imaging a fluorescence image.

Further, as still another embodiment, a narrow-band light source unit constituting a part of the medical light source apparatus may take the configurations shown in FIG. 10 to FIG. 13. Hereinafter, a fourth embodiment, fifth embodiment, and sixth embodiment will be respectively described with reference to FIG. 10, FIG. 11, and FIG. 12.

FIG. 10 to FIG. 13 are each a schematic diagram showing another configuration example of a narrow-band light source unit constituting a part of the medical light source apparatus. In each figure, the same configurations as those in the above-mentioned embodiments will be denoted by the same reference symbols, and description thereof will be omitted in some cases. Now, a characteristic configuration will be mainly described.

Since the wavelength and radiation angle of the collimating lens disposed between the laser light source and the reflection mirror differ for each type of laser light beam, a suitable collimating lens can be designed for each different type of laser light source. Meanwhile, as shown in the following fourth to sixth embodiments, the same type of collimating lens may be used for a different type of laser light beam.

Fourth Embodiment

Figure 10:
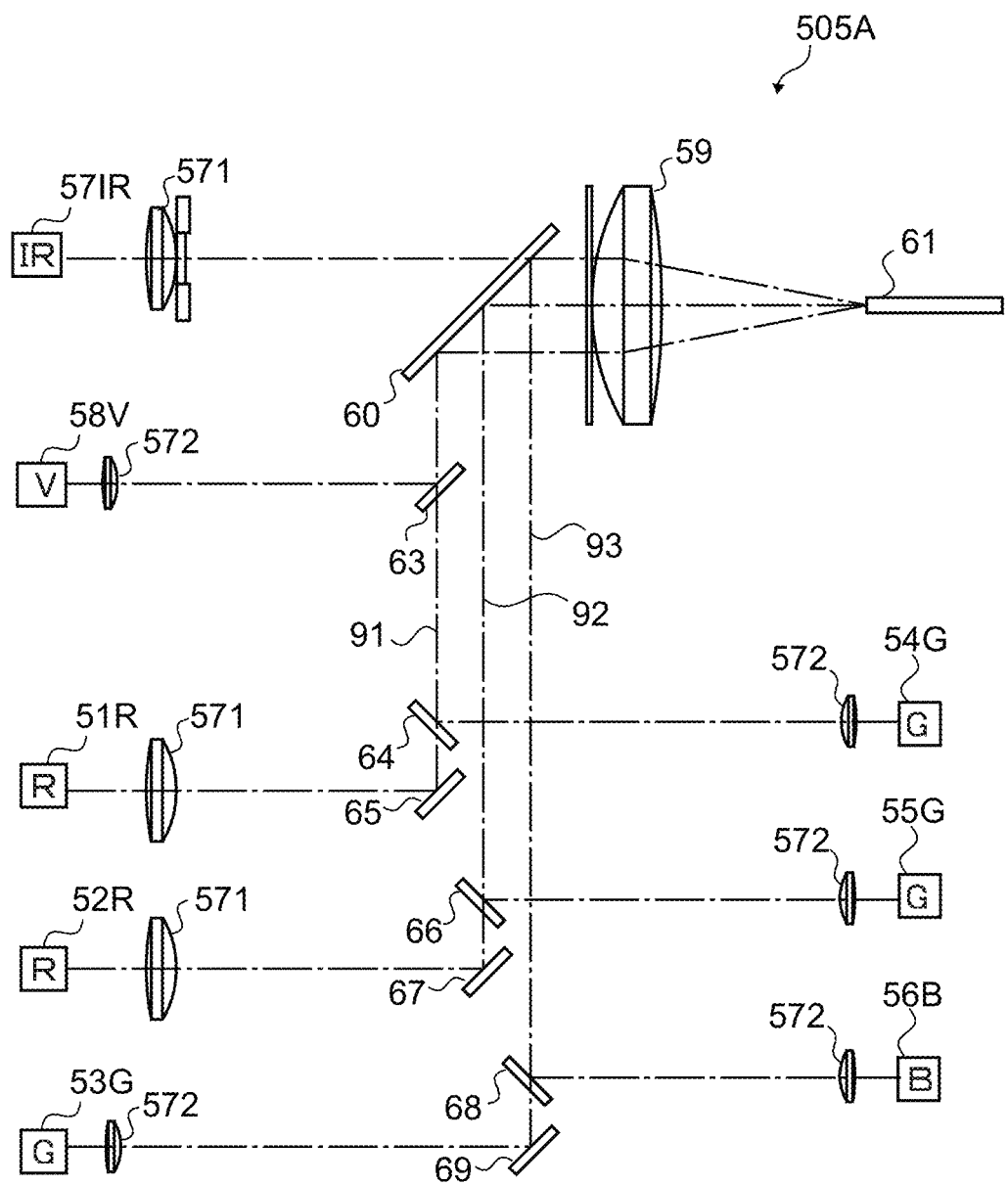
FIG. 10 is a diagram for describing a configuration example of a narrow-band light source unit constituting a part of a medical light source apparatus according to a fourth embodiment, and is a diagram for describing arrangement of an optical system.

As in a narrow-band light source unit 505A shown in FIG. 10, two types of collimating lenses, i.e., collimating lenses 571 and 572 may be used as collimating lenses positioned between laser light sources and reflection mirrors corresponding to the laser light sources in the entire narrow-band light source unit 505A.

In this embodiment, first collimating lenses 571 are disposed corresponding to laser light sources that emit laser light beams each having a relatively wide radiation angle, such as the R light sources 51R and 52R and the IR light source 57IR.

Meanwhile, second collimating lenses 572 are disposed corresponding to laser light sources that emit laser light beams each having a relatively narrow radiation angle, such as the V light source 58V, the B light source 56B, the G light sources 53G, 54G, and 55G The first collimating lenses 571 and the second the collimating lenses 572 are designed so that the cross-sectional shapes of the light beams at the time when each of the red light beam, the blue light beam, and the green light beam forming a white light beam (multiplexed light beam) is emitted from the laser light source, passes through the corresponding collimating lens, and enters the reflection mirror have substantially the same size.

Further, in this embodiment, the first collimating lens 571 is designed so that a common lens is used as the collimating lens that the red light beam or infrared light beam having a wide radiation angle and long wavelength enters. The second the collimating lens 572 is designed so that a common lens is used as the collimating lens that the violet light beam, green light beam, or blue light beam having a narrow radiation angle and short wavelength enters.

Note that the cross-sectional shapes of the light beams emitted from the laser light sources are elliptical, and the cross-sectional shapes of the light beams that enter the reflection mirror are elliptical.

"The cross-sectional shapes of the light beams the time of entering the reflection mirror have substantially the same size" described above represents that the diameters, .e.g., the values of short diameters, of the elliptical cross-sections of the light beams of all colors are within the range of ±50% of the average value of the short diameters of the elliptical cross-sections of the light beams of all colors.

As described above, the light beams emitted from the laser light sources, which form the multiplexed light beam (white light beam), are set so that the cross-sectional shapes of the light beams the time of entering the reflection mirror by the collimating lens are substantially the same.

Accordingly, for example, by designing the first collimating lens 571 so that the size of the cross-sectional shape of the light beam at the time when the red light beam having a wide radiation angle enters the reflection mirror is substantially the same as that of the cross-sectional shape of the light beam at the time when the blue light beam having a narrow radiation angle enters the reflection mirror, it is possible to reduce the size of the reflection mirror that the red light beam enters. Further, the size of the reflection mirror corresponding to each laser light source can be made the same.

As described above, by designing the collimating lens so that the cross-sectional shapes of the light beams of all colors the time of entering the reflection mirror are substantially the same, it is possible to reduce the size of the reflection mirror. Therefore, it is possible to improve the degree of freedom of arrangement position of the reflection mirror and reduce the size of the medical light source apparatus.

Since the wavelength and radiation angle of the laser light source differ for each type of laser light beam, a suitable collimating lens can be designed for each different type of laser light source. However, it is costly to prepare the collimating lens for each of all the laser light sources.

Meanwhile, in this embodiment, the red light beam and infrared light beam each having a wide radiation angle enter the same type of collimating lenses and the green light beam, blue light beam, and violet light beam each having a narrow radiation angle enter the same type of collimating lenses, i.e., two types of collimating lenses are used to configure the narrow-band light source unit.

In this embodiment, since a suitable collimating lens is selected for each laser light beam from the two types of collimating lenses, the difference in imaging position due to axial chromatic aberration is suppressed, the multiplexing efficiency to the rod integrator 61 can be enhanced, and the cost can be reduced by communalizing parts.

Note that in this embodiment, the example in which two type of collimating lenses are used to configure the narrow-band light source unit has been described.

Meanwhile, even in the case where the collimating lenses are different for each light source, by designing the collimating lens so that the size of the reflection mirror is determined corresponding to the light having a narrow radiation angle and the cross-sectional shapes of the light beams of all the colors the time of entering the reflection mirror are substantially the same, it is possible to reduce the size of the reflection mirror. Therefore, it is possible to improve the degree of freedom of arrangement position of the reflection mirror and reduce the size of the medical light source apparatus.

Fifth Embodiment

Hereinafter, a fifth embodiment will be described with reference to FIG. 11. The same components as those in the above-mentioned embodiments will be denoted by the same reference symbols, and description thereof will be omitted in some cases.

In the above-mentioned embodiments, the case where two R light sources are provided has been described. However, only one R light source may be provided as in a narrow-band light source unit 605A shown in FIG. 11. In this embodiment, by reducing the number of R light sources, it is possible to reduce the cost.

In this embodiment, the narrow-band light source unit 605A includes, as light sources, one R light source 652R, three G light source 651G, 653G, and 655G, one B light source 656B, one V light source 654V, and one IR light source 657IR. Further, similarly to the fourth embodiment, the narrow-band light source unit includes two types of collimating lenses, i.e., the first collimating lens 571 and the second the collimating lens 572.

Figure 11:
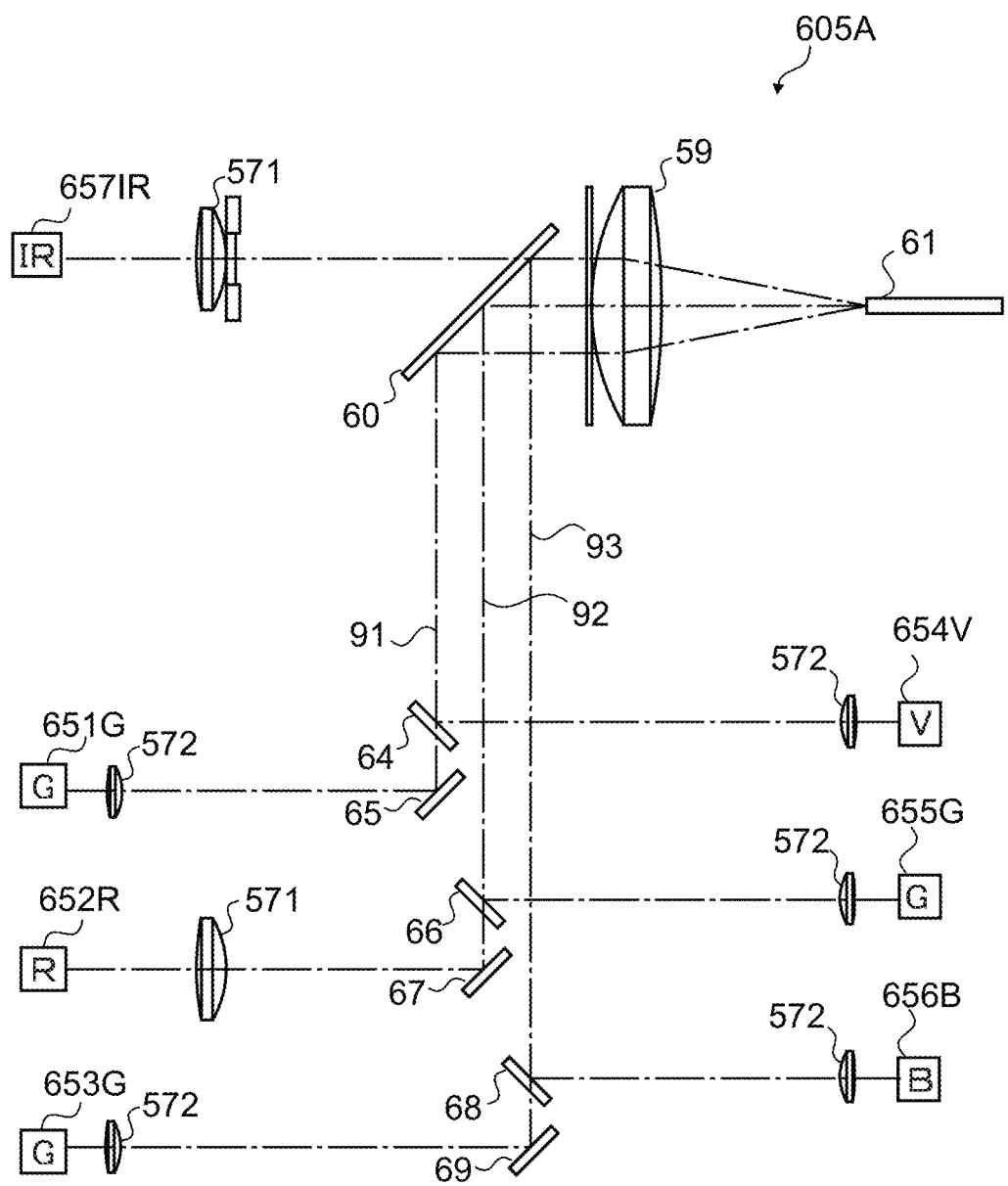
FIG. 11 is a diagram for describing a configuration example of a narrow-band light source unit constituting a part of a medical light source apparatus according to a fifth embodiment, and is a diagram for describing arrangement of an optical system.

In order to suppress color unevenness of a white light beam that is the multiplexed light beam of the red light beam, the blue light beam, and the green light beam, it is favorable that at least one red light beam, at least one blue light beam, and at least one green light beam pass through the optical paths located on the outermost side (the first optical path 91 and the third optical path 93 in the example shown in FIG. 11) when entering the condenser lens 59.

However, in the case where it is difficult to design such that all the laser light beams having different wavelengths pass through the optical paths located on the outermost side, it is favorable that a laser light beam having a relatively narrower radiation angle and laser light beam having a relatively wider radiation angle out of the plurality of laser light beams having different wavelengths respectively pass through the optical path located on the outermost side and the optical path located closer to the center.

Accordingly, it is possible to minimize the occurrence of color unevenness.

For example, in this embodiment, the violet light beam and blue light beam each having a narrow radiation angle pass through the optical paths located on the outermost side (the first optical path 91 and the third optical path 93), and the red light beam having a wide radiation angle passes through the optical path located at the center (the second optical path 92).

The light beam having a wide radiation angle has less risk of color unevenness than the light having a narrow radiation angle.

In the case of generating the multiplexed light beam (in this embodiment, the white light) using a plurality of light beams (in this embodiment, the red light beam, the blue light beam, and the green light beam) as in this embodiment, it is favorable to arrange, when the arrangement of laser light sources is limited and therefore all the light beams do not pass through the optical paths on the outside, laser light sources so that the light beam having a narrow radiation angle passes through the optical path on the outside and the light beam having a wide radiation angle passes through the optical path closer to the center. Accordingly, it is possible to generate the multiplexed light beam in which the occurrence of color unevenness is suppressed to the minimum.

Sixth Embodiment

Figure 12:
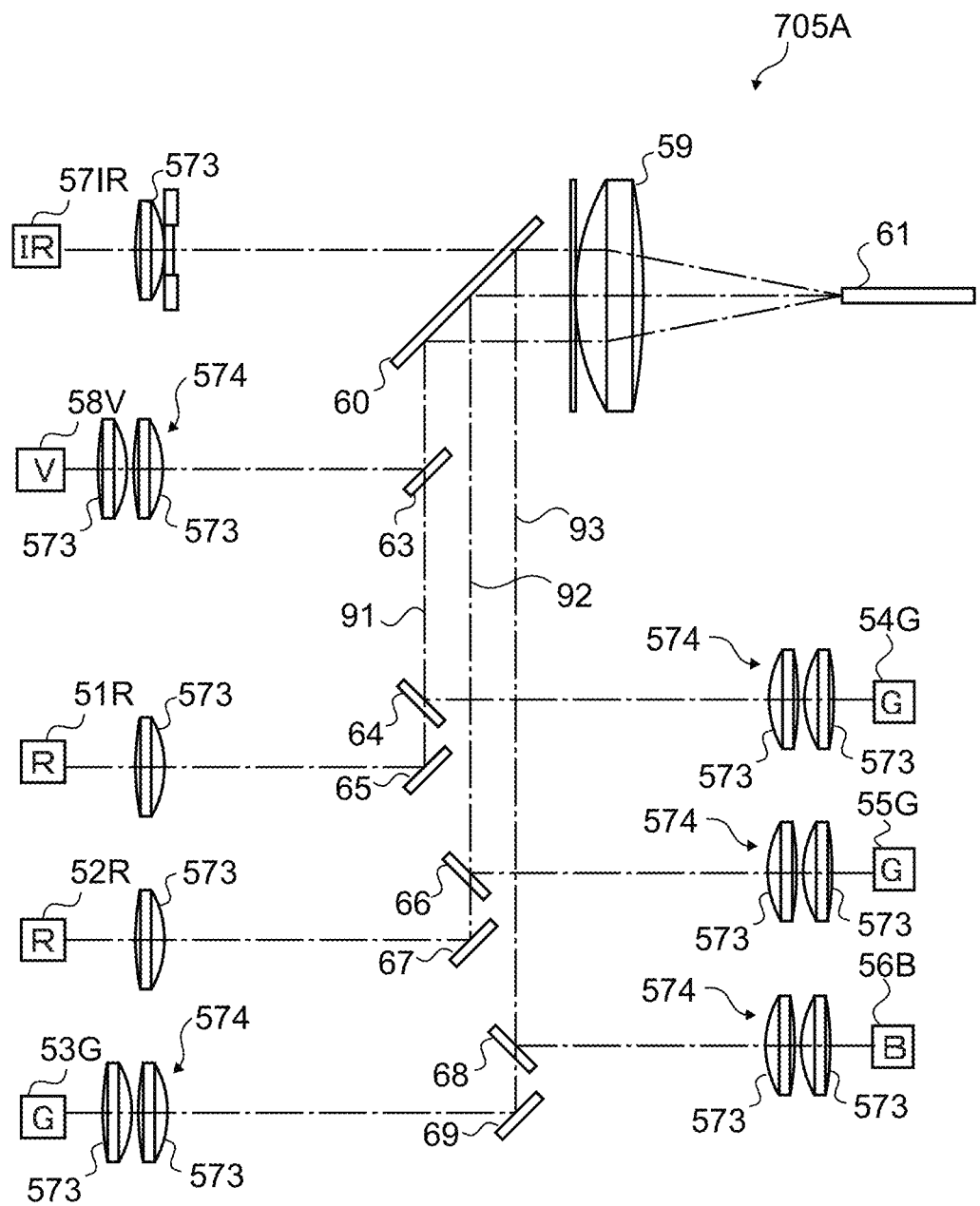
FIG. 12 is a diagram for describing a configuration example of a narrow-band light source unit constituting a part of a medical light source apparatus according to a sixth embodiment, and is a diagram for describing arrangement of an optical system.

In the examples shown in FIG. 10 and FIG. 11, the example in which two types of collimating lenses are used has been described. Meanwhile, as shown in FIG. 12, one type of collimating lenses may be used, and the number of collimating lenses to be used may be changed for each laser light source. Accordingly, since the same type of collimating lenses can be used in common, it is possible to reduce the cost.

In a narrow-band light source unit 705A shown in FIG. 12, the number of collimating lenses 573 arranged between each laser light source and each reflection mirror is one for the laser light source that emits a light beam having a relatively longer wavelength, such as the R light sources 51R and 52R and the IR light source 57IR.

Meanwhile, the number of collimating lenses 573 is two for the laser light source that emits a light beam having a relatively shorter wavelength, such as the V light source 58V, the B light source 56B, and the G light sources 53G, 54G, and 55G. The one in which two collimating lenses 573 are arranged is referred to as the combined lenses 574.

Figure 13:
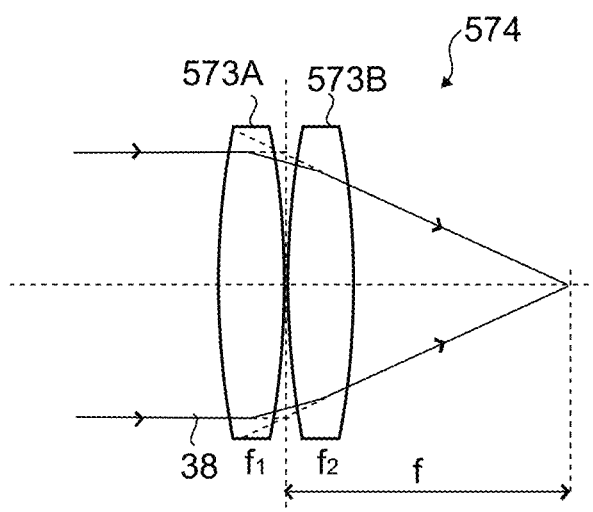
FIG. 13 is a diagram for describing a composite focal length.

Now, the composite focal length of the combined lenses 574 will be described with reference to FIG. 13. In FIG. 13, the two collimating lenses 573 having the same shape and type will be referred to as the first collimating lens 573A and the second collimating lens 573B.

As shown in FIG. 13, in the case where the approximate value of the distance between the first collimating lens 573A and the second collimating lens 573B in the combined lenses 574 obtained by superimposing the two collimating lenses 573A and 573B is zero, a composite focal length f is expressed as follows.

(Math. 1)

In the formula, f1 represents the focal length of the first collimating lens 573A and f2 represents the focal length of the second collimating lens 573B.

The composite focal length f is the distance between the principal point, which is a point of the light refraction position on the optical axis and the focal point at the time of assuming that an incident light beam 38 to the optical system of the entire combined lenses 574 is refracted only once in the optical system to be an emission light beam.

In the case where f1=f2=10 (mm), the composite focal length f is calculated to be 5 mm from the above-mentioned formula. That is, by superimposing two collimating lenses, the focal length can be reduced to half of that in the case of one collimating lens.

As described above, it is possible to change the focal length by the number of collimating lenses to be superimposed and reduce the focal length as the number of collimating lenses to be superimposed increases.

By arranging the collimating lenses so that the focal lengths of the red light beam and infrared light beam each having a wide radiation angle are long, it is possible to reduce the light flux of light to be emitted from the collimating lens.

In this embodiment, the collimating lens (collimating lenses 573 disposed corresponding to the light sources 51R and 52R in FIG. 12) corresponding to the light beam having a wide radiation angle is used as the collimating lens 573 used in common. Regarding the collimating lenses disposed corresponding to other light beams, the number of collimating lenses 573 used in common is two, which makes it possible to adjust the focal length.

As described above, in this embodiment, it is possible to use parts (collimating lenses) in common in each laser light source, and reduce the cost as compared with the case of preparing different collimating lenses for each laser light source.

Next, how much the size of the medical light source apparatus can be reduced will be specifically described with reference to FIG. 14.

Figure 14A:
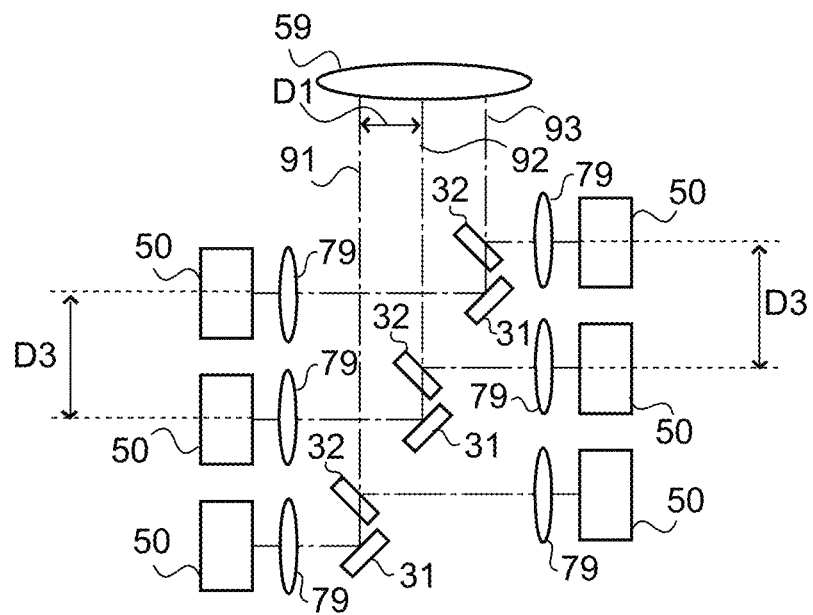
FIG. 14 is a diagram for describing that a medical light source apparatus can be miniaturized.

FIG. 14A is a diagram describing arrangement of laser light sources in a narrow-band light source unit of a medical light source apparatus according to an embodiment of the present technology. Two laser light sources that emit light beams entering the same dichroic mirror are disposed opposed to each other. The laser light beams emitted from the two laser light sources arranged opposed to each other are emitted in opposite directions.

Figure 14B:
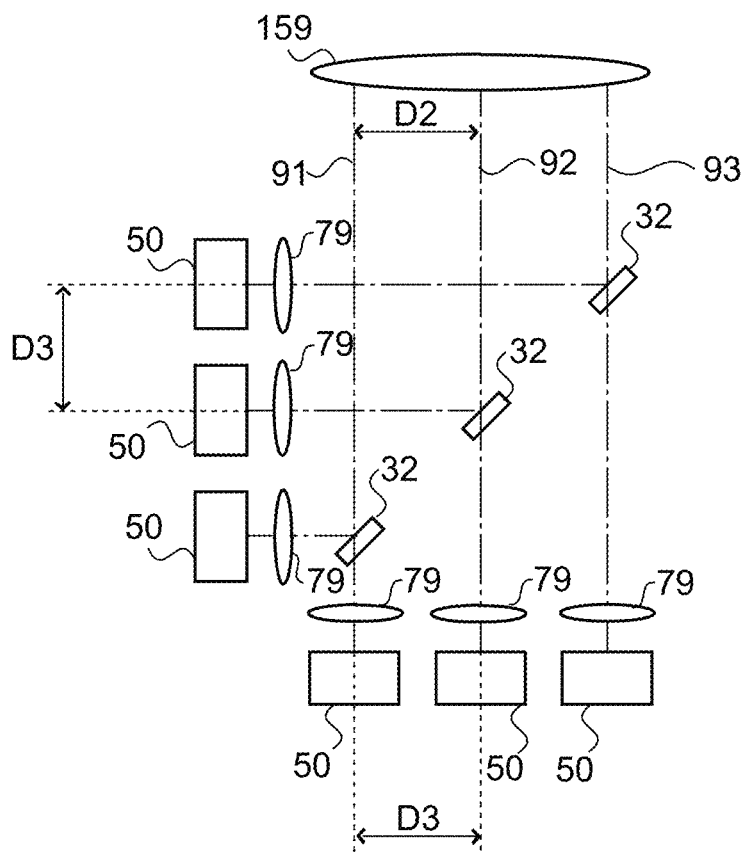

FIG. 14B shows an arrangement example of laser light sources in a narrow-band light source unit of a medical light source apparatus according to a comparative example.

In FIGS. 14A and 14B, for the sake of convenience, a reference symbol 50 is given to each laser light source, a reference symbol 79 is given to each collimating lens, a reference symbol 31 is given to each reflection mirror, and a reference symbol 32 is given to a dichroic mirror. A reference symbol 59 is given to a condenser lens in FIG. 14A, and a reference symbol 159 is given to a condenser lens in FIG. 14B. Further, the first to third optical paths 91 to 93 represent the optical paths of light beams that enter the condenser lens 59 or 159.

At present, for applications of medical lighting, a high output class laser diode is necessary, and for example, a laser diode with a package shape of φ9 mm CAN is used. Optical members such as a laser light source, a collimating lens, a dichroic mirror, a reflection mirror, and a condenser lens are arranged considering the heat crosstalk of the laser light source and the vignetting of the laser light beam, and the size of the condenser lens is determined on the basis of the arrangement position.

In the arrangement example shown in FIG. 14B, considering the heat crosstalk of laser light sources 50 and the vignetting of the laser light beams, for example, the laser light sources 50 are arranged at such intervals that a distance D3 between adjacent laser light sources is 20 mm.

In the example shown in FIG. 14B, the arrangement intervals of the laser light sources 50 emitting light beams that are transmitted through dichroic mirrors 32 and enter a condenser lens 159 without being refracted are directly reflected in a distance D2 between the first to third optical paths 91 to 93. Accordingly, the length of the distance D2 between the optical paths is set to, for example, 20 mm, and a lens with a diameter of 50 mm is used as the condenser lens 159.

Such a medical light source apparatus has a size of, for example, 7 cm in length, 7 cm in width, 7 cm in height, and 343 cm$^3$ in volume.

Meanwhile, in the arrangement example shown in FIG. 14A, the two laser light sources 50 emitting light beams that enter the same dichroic mirror 32 are disposed opposed to each other. The laser light beams emitted from the laser light sources 50 are reflected by the reflection mirror 31 or the dichroic mirror 32, and the optical paths of the laser light beams are changed in a direction different from the emission directions from the laser light sources 50. Then, the laser light beams enter the condenser lens 59.

Therefore, in the example shown in FIG. 14A, the arrangement intervals of the laser light sources 50 do not affect the determination of a distance D1 between the first to third optical paths 91 to 93. The distance D1 between the optical paths is set, for example, 5 mm, and a lens with a diameter of 20 mm is used as the condenser lens 59.

For example, as described in the fourth embodiment, by designing the collimating lenses 79 so that the cross-sectional shapes of the light beams of all colors at the time of entering the reflection mirror are substantially the same, the size of the reflection mirror can be reduced. Therefore, it is possible to shorten the arrangement intervals of the reflection mirrors.

Accordingly, as shown in FIG. 14A, by reducing the size of the reflection mirror, it is possible to reduce the distance D1 between the optical paths to, for example, 5 mm, and reduce the size of the medical light source apparatus.

The size of the medical light source apparatus with such arrangement has a size of, for example, 6 cm in length, 6 cm in width, 6 cm in height, and 144 $cm^3$ in volume.

As described above, the medical light source apparatus according to an embodiment of the present technology shown in FIG. 14A can be downsized by ½ or more in volume ratio as compared with the medical light source apparatus according to the comparative example shown in FIG. 14B.

The medical light source apparatus according to an embodiment of the present disclosure is applicable to an endoscope system and a microscope system. Hereinafter, an endoscope surgery system and a microscopic surgery system will be respectively described with reference to FIG. 15 to FIG. 18 and FIG. 19 and FIG. 20.

Endoscope Surgery System

Hereinafter, an endoscope surgery system to which the technology according to an embodiment of the present disclosure can be applied will be described with reference to FIG. 15 to FIG. 18.

Figure 17:
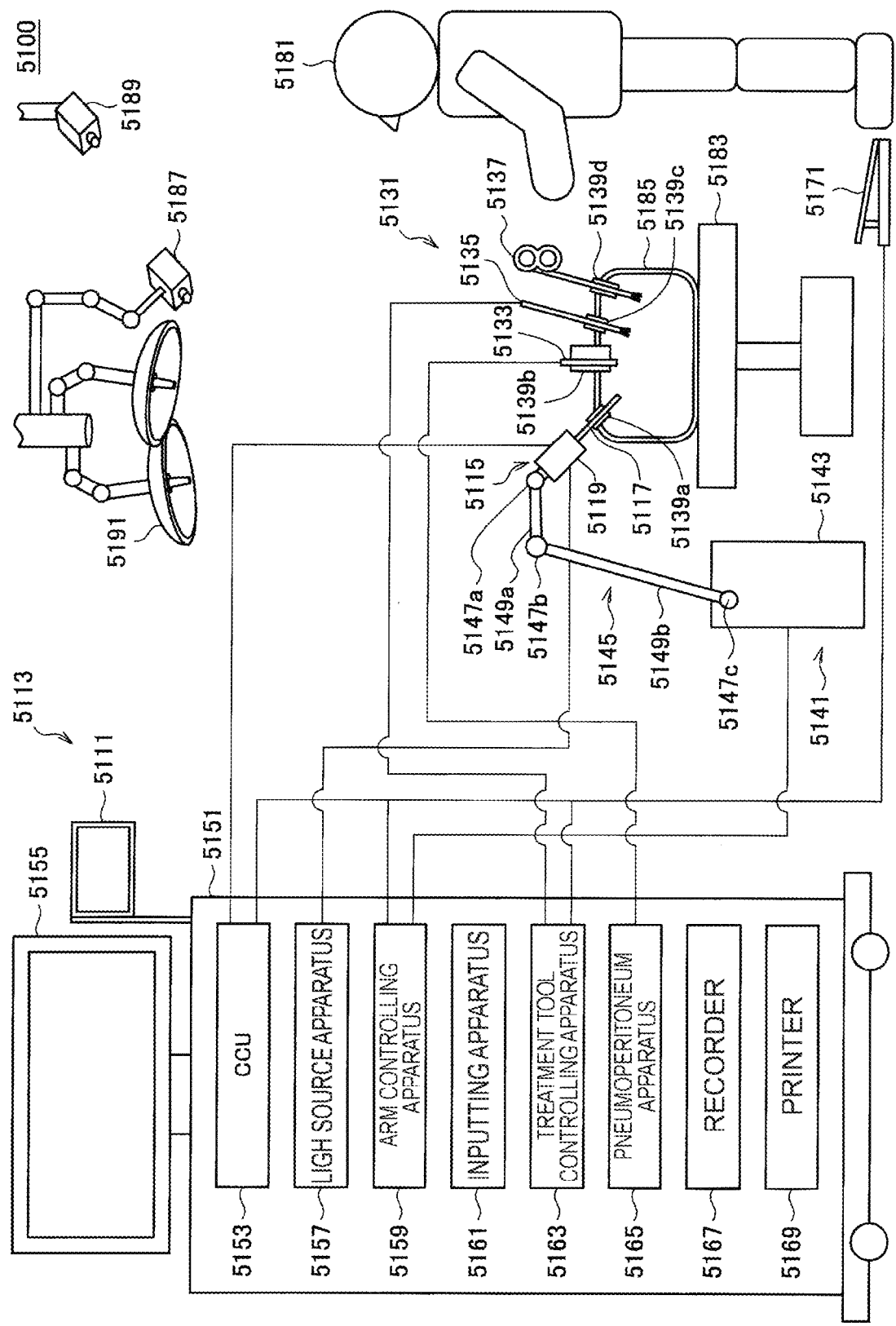
FIG. 17 is a view illustrating an example of a state of surgery to which the surgery room system is applied.

In FIG. 17, a light source apparatus denoted by a reference symbol 5157 corresponds to the medical light source apparatus according to an embodiment of the present disclosure. In the endoscope surgery system, an endoscope that is connected to a medical light source apparatus, guides output light from the medical light source apparatus, and applies it to a part to be observed is provided.

Figure 15:
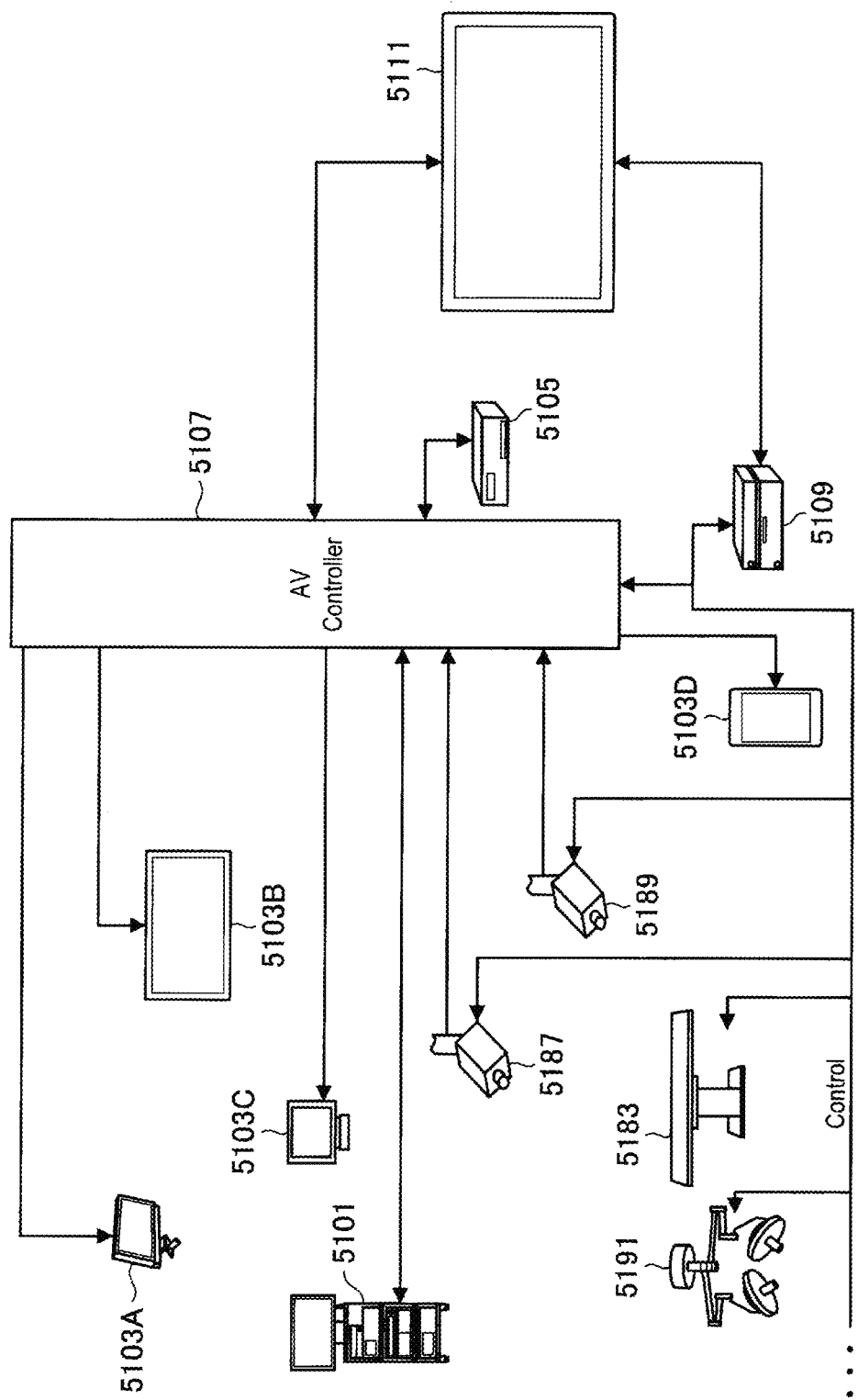
FIG. 15 is a view schematically depicting a general configuration of a surgery room system.

FIG. 15 is a view schematically depicting a general configuration of a surgery room system 5100 to which the technology according to an embodiment of the present disclosure can be applied. Referring to FIG. 15, the surgery room system 5100 is configured such that a group of apparatus installed in a surgery room are connected for cooperation with each other through an audiovisual (AV) controller 5107 and a surgery room controlling apparatus 5109.

In the surgery room, various apparatus may be installed. In FIG. 15, as an example, various apparatus group 5101 for endoscopic surgery, a ceiling camera 5187, a surgery field camera 5189, a plurality of display apparatus 5103A to 5103D, a recorder 5105, a patient bed 5183 and an illumination 5191 are depicted. The ceiling camera 5187 is provided on the ceiling of a surgery room and images the hands of a surgeon. The surgery field camera 5189 is provided on the ceiling of the surgery room and images a state of the entire surgery room.

Among the apparatus mentioned, the apparatus group 5101 belongs to an endoscopic surgery system 5113 hereinafter described and include an endoscope, a display apparatus which displays an image picked up by the endoscope and so forth. Various apparatus belonging to the endoscopic surgery system 5113 are referred to also as medical equipment. Meanwhile, the display apparatus 5103A to 5103D, the recorder 5105, the patient bed 5183 and the illumination 5191 are apparatus which are equipped, for example, in the surgery room separately from the endoscopic surgery system 5113. The apparatus which do not belong to the endoscopic surgery system 5113 are referred to also as non-medical equipment. The audiovisual controller 5107 and/or the surgery room controlling apparatus 5109 cooperatively control operation of the medical equipment and the non-medical equipment with each other.

The audiovisual controller 5107 integrally controls processes of the medical equipment and the non-medical equipment relating to image display. Specifically, each of the apparatus group 5101, the ceiling camera 5187 and the surgery field camera 5189 from among the apparatus provided in the surgery room system 5100 may be an apparatus having a function of sending information to be displayed during surgery (such information is hereinafter referred to as display information, and the apparatus mentioned is hereinafter referred to as apparatus of a sending source). Meanwhile, each of the display apparatus 5103A to 5103D may be an apparatus to which display information is outputted (the apparatus is hereinafter referred to also as apparatus of an output destination). Further, the recorder 5105 may be an apparatus which serves as both of an apparatus of a sending source and an apparatus of an output destination. The audiovisual controller 5107 has a function of controlling operation of an apparatus of a sending source and an apparatus of an output destination to acquire display information from the apparatus of a sending source and transmit the display information to the apparatus of an output destination so as to be displayed or recorded. It is to be noted that the display information includes various images picked up during surgery, various kinds of information relating to the surgery (for example, physical information of a patient, inspection results in the past or information regarding a surgical procedure) and so forth.

Specifically, to the audiovisual controller 5107, information relating to an image of a surgical region in a body lumen of a patient imaged by the endoscope may be transmitted as the display information from the apparatus group 5101. Further, from the ceiling camera 5187, information relating to an image of the hands of the surgeon picked up by the ceiling camera 5187 may be transmitted as display information. Further, from the surgery field camera 5189, information relating to an image picked up by the surgery field camera 5189 and illustrating a state of the entire surgery room may be transmitted as display information. It is to be noted that, if a different apparatus having an image pickup function exists in the surgery room system 5100, then the audiovisual controller 5107 may acquire information relating to an image picked up by the different apparatus as display information also from the different apparatus.

Alternatively, for example, in the recorder 5105, information relating to such images as mentioned above picked up in the past is recorded by the audiovisual controller 5107. The audiovisual controller 5107 can acquire, as display information, information relating to the images picked up in the past from the recorder 5105. It is to be noted that also various pieces of information relating to surgery may be recorded in advance in the recorder 5105.

The audiovisual controller 5107 controls at least one of the display apparatus 5103A to 5103D, which are apparatus of an output destination, to display acquired display information (namely, images picked up during surgery or various pieces of information relating to the surgery). In the example depicted, the display apparatus 5103A is a display apparatus installed so as to be suspended from the ceiling of the surgery room; the display apparatus 5103B is a display apparatus installed on a wall face of the surgery room; the display apparatus 5103C is a display apparatus installed on a desk in the surgery room; and the display apparatus 5103D is a mobile apparatus (for example, a tablet personal computer (PC)) having a display function.

Further, though not depicted in FIG. 15, the surgery room system 5100 may include an apparatus outside the surgery room. The apparatus outside the surgery room may be, for example, a server connected to a network constructed inside and outside the hospital, a PC used by medical staff, a projector installed in a meeting room of the hospital or the like. Where such an external apparatus is located outside the hospital, also it is possible for the audiovisual controller 5107 to cause display information to be displayed on a display apparatus of a different hospital through a teleconferencing system or the like to perform telemedicine.

The surgery room controlling apparatus 5109 integrally controls processes other than processes relating to image display on the non-medical equipment. For example, the surgery room controlling apparatus 5109 controls driving of the patient bed 5183, the ceiling camera 5187, the surgery field camera 5189 and the illumination 5191.

In the surgery room system 5100, a centralized operation panel 5111 is provided such that it is possible to issue an instruction regarding image display to the audiovisual controller 5107 or issue an instruction regarding operation of the non-medical equipment to the surgery room controlling apparatus 5109 through the centralized operation panel 5111. The centralized operation panel 5111 is configured by providing a touch panel on a display face of a display apparatus.

Figure 16:
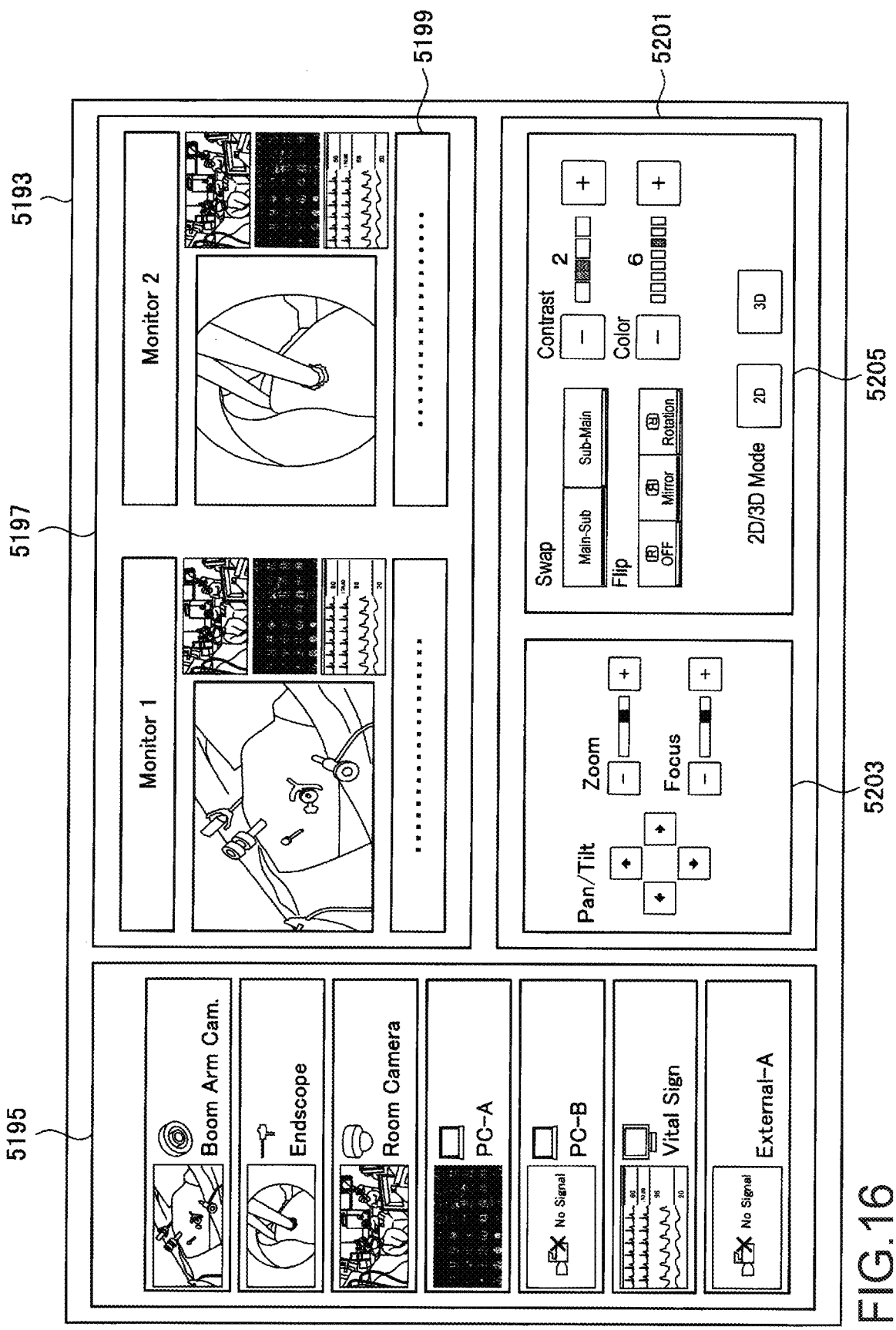
FIG. 16 is a view depicting an example of display of an operation screen image of a centralized operation panel.

FIG. 16 is a view depicting an example of display of an operation screen image on the centralized operation panel 5111. In FIG. 16, as an example, an operation screen image is depicted which corresponds to a case in which two display apparatus are provided as apparatus of an output destination in the surgery room system 5100. Referring to FIG. 16, the operation screen image 5193 includes a sending source selection region 5195, a preview region 5197 and a control region 5201.

In the sending source selection region 5195, the sending source apparatus provided in the surgery room system 5100 and thumbnail screen images representative of display information the sending source apparatus have are displayed in an associated manner with each other. A user can select display information to be displayed on the display apparatus from any of the sending source apparatus displayed in the sending source selection region 5195.

In the preview region 5197, a preview of screen images displayed on two display apparatus (Monitor 1 and Monitor 2) which are apparatus of an output destination is displayed. In the example depicted, four images are displayed by picture in picture (PinP) display in regard to one display apparatus. The four images correspond to display information sent from the sending source apparatus selected in the sending source selection region 5195. One of the four images is displayed in a comparatively large size as a main image while the remaining three images are displayed in a comparatively small size as sub images. The user can exchange between the main image and the sub images by suitably selecting one of the images from among the four images displayed in the region. Further, a status displaying region 5199 is provided below the region in which the four images are displayed, and a status relating to surgery (for example, elapsed time of the surgery, physical information of the patient and so forth) may be displayed suitably in the status displaying region 5199.

A sending source operation region 5203 and an output destination operation region 5205 are provided in the control region 5201. In the sending source operation region 5203, a graphical user interface (GUI) part for performing an operation for an apparatus of a sending source is displayed. In the output destination operation region 5205, a GUI part for performing an operation for an apparatus of an output destination is displayed. In the example depicted, GUI parts for performing various operations for a camera (panning, tilting and zooming) in an apparatus of a sending source having an image pickup function are provided in the sending source operation region 5203. The user can control operation of the camera of an apparatus of a sending source by suitably selecting any of the GUI parts. It is to be noted that, though not depicted, where the apparatus of a sending source selected in the sending source selection region 5195 is a recorder (namely, where an image recorded in the recorder in the past is displayed in the preview region 5197), GUI parts for performing such operations as reproduction of the image, stopping of reproduction, rewinding, fast-feeding and so forth may be provided in the sending source operation region 5203.

Further, in the output destination operation region 5205, GUI parts for performing various operations for display on a display apparatus which is an apparatus of an output destination (swap, flip, color adjustment, contrast adjustment and switching between two dimensional (2D) display and three dimensional (3D) display) are provided. The user can operate the display of the display apparatus by suitably selecting any of the GUI parts.

It is to be noted that the operation screen image to be displayed on the centralized operation panel 5111 is not limited to the depicted example, and the user may be able to perform operation inputting to each apparatus which can be controlled by the audiovisual controller 5107 and the surgery room controlling apparatus 5109 provided in the surgery room system 5100 through the centralized operation panel 5111.

FIG. 17 is a view illustrating an example of a state of surgery to which the surgery room system described above is applied. The ceiling camera 5187 and the surgery field camera 5189 are provided on the ceiling of the surgery room such that it can image the hands of a surgeon (medical doctor) 5181 who performs treatment for an affected area of a patient 5185 on the patient bed 5183 and the entire surgery room. The ceiling camera 5187 and the surgery field camera 5189 may include a magnification adjustment function, a focal distance adjustment function, an imaging direction adjustment function and so forth. The illumination 5191 is provided on the ceiling of the surgery room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 are connected for cooperation with each other through the audiovisual controller 5107 and the surgery room controlling apparatus 5109 (not depicted in FIG. 17) as depicted in FIG. 15. The centralized operation panel 5111 is provided in the surgery room, and the user can suitably operate the apparatus existing in the surgery room through the centralized operation panel 5111 as described hereinabove.

In the following, a configuration of the endoscopic surgery system 5113 is described in detail. As depicted, the endoscopic surgery system 5113 includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139a to 5139d are used to puncture the abdominal wall. Then, a lens barrel 5117 of the endoscope 5115 and the other surgical tools 5131 are inserted into body lumens of the patient 5185 through the trocars 5139a to 5139d. In the example depicted, as the other surgical tools 5131, a pneumoperitoneum tube 5133, an energy treatment tool 5135 and forceps 5137 are inserted into body lumens of the patient 5185. Further, the energy treatment tool 5135 is a treatment tool for performing incision and peeling of a tissue, sealing of a blood vessel or the like by high frequency current or ultrasonic vibration. However, the surgical tools 5131 depicted are mere examples at all, and as the surgical tools 5131, various surgical tools which are generally used in endoscopic surgery such as, for example, a pair of tweezers or a retractor may be used.

An image of a surgical region in a body lumen of the patient 5185 picked up by the endoscope 5115 is displayed on a display apparatus 5155. The surgeon 5181 would use the energy treatment tool 5135 or the forceps 5137 while watching the image of the surgical region displayed on the display apparatus 5155 on the real time basis to perform such treatment as, for example, resection of an affected area. It is to be noted that, though not depicted, the pneumoperitoneum tube 5133, the energy treatment tool 5135, and the forceps 5137 are supported by the surgeon 5181, an assistant or the like during surgery.

Supporting Arm Apparatus

The supporting arm apparatus 5141 includes an arm unit 5145 extending from a base unit 5143. In the example depicted, the arm unit 5145 includes joint portions 5147a, 5147b and 5147c and links 5149a and 5149b and is driven under the control of an arm controlling apparatus 5159. The endoscope 5115 is supported by the arm unit 5145 such that the position and the posture of the endoscope 5115 are controlled. Consequently, stable fixation in position of the endoscope 5115 can be implemented.

Endoscope

The endoscope 5115 includes the lens barrel 5117 which has a region of a predetermined length from a distal end thereof to be inserted into a body lumen of the patient 5185, and a camera head 5119 connected to a proximal end of the lens barrel 5117. In the example depicted, the endoscope 5115 is depicted which is configured as a hard mirror having the lens barrel 5117 of the hard type. However, the endoscope 5115 may otherwise be configured as a soft mirror having the lens barrel 5117 of the soft type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body lumen of the patient 5185 through the objective lens. It is to be noted that the endoscope 5115 may be a direct view mirror or may be a perspective view mirror or a side view mirror.

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5153. It is to be noted that the camera head 5119 has a function incorporated therein for suitably driving the optical system of the camera head 5119 to adjust the magnification and the focal distance.

It is to be noted that, in order to establish compatibility with, for example, a stereoscopic vision (3D display), a plurality of image pickup elements may be provided on the camera head 5119. In this case, a plurality of relay optical systems are provided in the inside of the lens barrel 5117 in order to guide observation light to the plurality of respective image pickup elements.

Various Apparatus Incorporated in Cart

The CCU 5153 includes a central processing unit (CPU), a graphics processing unit (GPU) or the like and integrally controls operation of the endoscope 5115 and the display apparatus 5155. Specifically, the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. Further, the audiovisual controller 5107 depicted in FIG. 15 is connected to the CCU 5153. The CCU 5153 provides the image signal for which the image processes have been performed also to the audiovisual controller 5107. Further, the CCU 5153 transmits a control signal to the camera head 5119 to control driving of the camera head 5119. The control signal may include information relating to an image pickup condition such as a magnification or a focal distance. The information relating to an image pickup condition may be inputted through the inputting apparatus 5161 or may be inputted through the centralized operation panel 5111 described hereinabove.

The display apparatus 5155 displays an image based on an image signal for which the image processes have been performed by the CCU 5153 under the control of the CCU 5153. If the endoscope 5115 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5155. Where the apparatus is ready for imaging of a high resolution such as 4K or 8K, if the display apparatus used as the display apparatus 5155 has a size of equal to or not less than 55 inches, then a more immersive experience can be obtained. Further, a plurality of display apparatus 5155 having different resolutions and/or different sizes may be provided in accordance with purposes.

The light source apparatus 5157 includes a light source such as, for example, a light emitting diode (LED) and supplies irradiation light for imaging of a surgical region to the endoscope 5115.

The arm controlling apparatus 5159 includes a processor such as, for example, a CPU and operates in accordance with a predetermined program to control driving of the arm unit 5145 of the supporting arm apparatus 5141 in accordance with a predetermined controlling method.

An inputting apparatus 5161 is an input interface for the endoscopic surgery system 5113. A user can perform inputting of various kinds of information or instruction inputting to the endoscopic surgery system 5113 through the inputting apparatus 5161. For example, the user would input various kinds of information relating to surgery such as physical information of a patient, information regarding a surgical procedure of the surgery and so forth through the inputting apparatus 5161. Further, the user would input, for example, an instruction to drive the arm unit 5145, an instruction to change an image pickup condition (type of irradiation light, magnification, focal distance or the like) by the endoscope 5115, an instruction to drive the energy treatment tool 5135 or a like through the inputting apparatus 5161.

The type of the inputting apparatus 5161 is not limited and may be that of any one of various known inputting apparatus. As the inputting apparatus 5161, for example, a mouse, a keyboard, a touch panel, a switch, a foot switch 5171 and/or a lever or the like may be applied. Where a touch panel is used as the inputting apparatus 5161, it may be provided on the display face of the display apparatus 5155.

The inputting apparatus 5161 is otherwise a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5161 includes a camera which can detect a motion of a user, and various kinds of inputting are performed in response to a gesture or a line of sight of a user detected from a video picked up by the camera. Further, the inputting apparatus 5161 includes a microphone which can collect the voice of a user, and various kinds of inputting are performed by voice through the microphone. By configuring the inputting apparatus 5161 such that various kinds of information can be inputted in a contactless fashion in this manner, especially a user who belongs to a clean area (for example, the surgeon 5181) can operate an apparatus belonging to an unclean area in a contactless fashion. Further, since the user can operate an apparatus without releasing a possessed surgical tool from its hand, the convenience to the user is improved.

A treatment tool controlling apparatus 5163 controls driving of the energy treatment tool 5135 for cautery or incision of a tissue, sealing of a blood vessel or the like. A pneumoperitoneum apparatus 5165 feeds gas into a body lumen of the patient 5185 through the pneumoperitoneum tube 5133 to inflate the body lumen in order to secure the field of view of the endoscope 5115 and secure the working space for the surgeon. A recorder 5167 is an apparatus capable of recording various kinds of information relating to surgery. A printer 5169 is an apparatus capable of printing various kinds of information relating to surgery in various forms such as a text, an image or a graph.

In the following, especially a characteristic configuration of the endoscopic surgery system 5113 is described in more detail.

Supporting Arm Apparatus

The supporting arm apparatus 5141 includes the base unit 5143 serving as a base, and the arm unit 5145 extending from the base unit 5143. In the example depicted, the arm unit 5145 includes the plurality of joint portions 5147*a*, 5147*b* and 5147*c* and the plurality of links 5149*a* and 5149*b* connected to each other by the joint portion 5147*b*. In FIG. 17, for simplified illustration, the configuration of the arm unit 5145 is depicted in a simplified form. Actually, the shape, number and arrangement of the joint portions 5147*a* to 5147*c* and the links 5149*a* and 5149*b* and the direction and so forth of axes of rotation of the joint portions 5147*a* to 5147*c* can be set suitably such that the arm unit 5145 has a desired degree of freedom. For example, the arm unit 5145 may preferably be included such that it has a degree of freedom equal to or not less than 6 degrees of freedom. This makes it possible to move the endoscope 5115 freely within the movable range of the arm unit 5145. Consequently, it becomes possible to insert the lens barrel 5117 of the endoscope 5115 from a desired direction into a body lumen of the patient 5185.

An actuator is provided in the joint portions 5147*a* to 5147*c*, and the joint portions 5147*a* to 5147*c* include such that they are rotatable around predetermined axes of rotation thereof by driving of the actuator. The driving of the actuator is controlled by the arm controlling apparatus 5159 to control the rotational angle of each of the joint portions 5147*a* to 5147*c* thereby to control driving of the arm unit 5145. Consequently, control of the position and the posture of the endoscope 5115 can be implemented. Thereupon, the arm controlling apparatus 5159 can control driving of the arm unit 5145 by various known controlling methods such as force control or position control.

For example, if the surgeon 5181 suitably performs operation inputting through the inputting apparatus 5161 (including the foot switch 5171), then driving of the arm unit 5145 may be controlled suitably by the arm controlling apparatus 5159 in response to the operation input to control the position and the posture of the endoscope 5115. After the endoscope 5115 at the distal end of the arm unit 5145 is moved from an arbitrary position to a different arbitrary position by the control just described, the endoscope 5115 can be supported fixedly at the position after the movement. It is to be noted that the arm unit 5145 may be operated in a master-slave fashion. In this case, the arm unit 5145 may be remotely controlled by the user through the inputting apparatus 5161 which is placed at a place remote from the surgery room.

Further, where force control is applied, the arm controlling apparatus 5159 may perform power-assisted control to drive the actuators of the joint portions 5147*a* to 5147*c* such that the arm unit 5145 may receive external force by the user and move smoothly following the external force. This makes it possible to move the arm unit 5145 with comparatively weak force when the user directly touches with and moves the arm unit 5145. Accordingly, it becomes possible for the user to move the endoscope 5115 more intuitively by a simpler and easier operation, and the convenience to the user can be improved.

Here, generally in endoscopic surgery, the endoscope 5115 is supported by a medical doctor called scopist. In contrast, where the supporting arm apparatus 5141 is used, the position of the endoscope 5115 can be fixed with a higher degree of certainty without hands, and therefore, an image of a surgical region can be obtained stably and surgery can be performed smoothly.

It is to be noted that the arm controlling apparatus 5159 may not necessarily be provided on the cart 5151. Further, the arm controlling apparatus 5159 may not necessarily be a single apparatus. For example, the arm controlling apparatus 5159 may be provided in each of the joint portions 5147a to 5147c of the arm unit 5145 of the supporting arm apparatus 5141 such that the plurality of arm controlling apparatus 5159 cooperate with each other to implement driving control of the arm unit 5145.

Light Source Apparatus

The light source apparatus 5157 supplies irradiation light upon imaging of a surgical region to the endoscope 5115. The light source apparatus 5157 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5157. Further, in this case, if laser beams from the RGB laser light sources are applied time-divisionally on an observation target and driving of the image pickup elements of the camera head 5119 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5157 may be controlled such that the intensity of light to be outputted is changed for each predetermined time. By controlling driving of the image pickup element of the camera head 5119 in synchronism with the timing of the change of the intensity of light to acquire images time-divisionally and synthesizing the images, an image of a high dynamic range free from underexposed blocked up shadows and overexposed highlights can be created.

Further, the light source apparatus 5157 may be configured to supply light of a predetermined wavelength band ready for special light observation. In special light observation, for example, by utilizing the wavelength dependency of absorption of light of a body tissue, narrow band light observation (narrow band imaging) of imaging a predetermined tissue such as a blood vessel of a superficial portion of the mucous membrane or the like in a high contrast is performed by applying light of a narrower band in comparison with irradiation light upon ordinary observation (namely, white light). Alternatively, in special light observation, fluorescent observation for obtaining an image from fluorescent light generated by irradiation of excitation light may also be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5157 can be configured to supply such narrow-band light and/or excitation light suitable for special light observation as described above.

Camera Head and CCU

Figure 18:
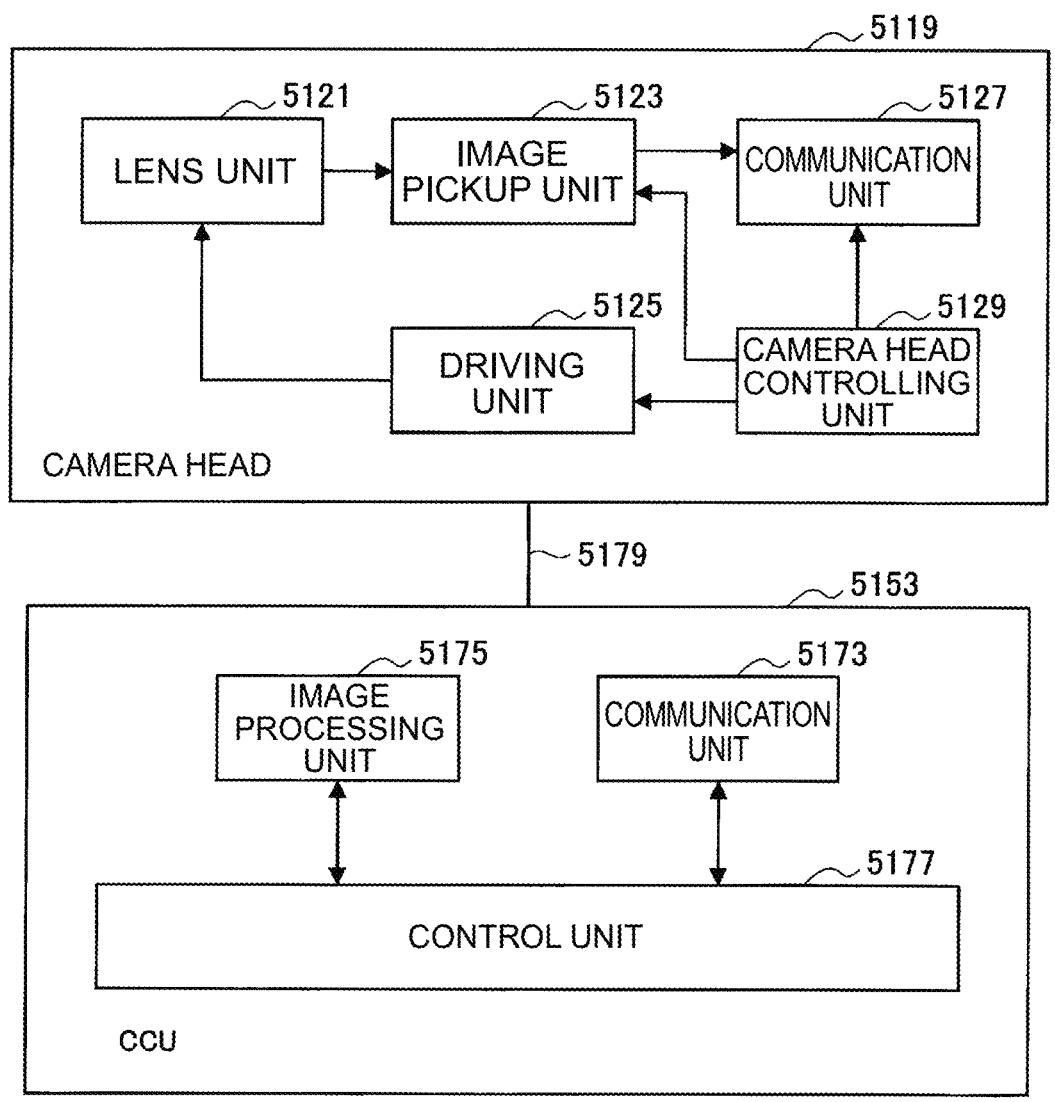
FIG. 18 is a block diagram depicting an example of a functional configuration of a camera head and a camera control unit (CCU) depicted in FIG. 17.

Functions of the camera head 5119 of the endoscope 5115 and the CCU 5153 are described in more detail with reference to FIG. 18. FIG. 18 is a block diagram depicting an example of a functional configuration of the camera head 5119 and the CCU 5153 depicted in FIG. 17.

Referring to FIG. 18, the camera head 5119 has, as functions thereof, a lens unit 5121, an image pickup unit 5123, a driving unit 5125, a communication unit 5127 and a camera head controlling unit 5129. Further, the CCU 5153 has, as functions thereof, a communication unit 5173, an image processing unit 5175 and a control unit 5177. The camera head 5119 and the CCU 5153 are connected to be bidirectionally communicable to each other by a transmission cable 5179.

First, a functional configuration of the camera head 5119 is described. The lens unit 5121 is an optical system provided at a connecting location of the camera head 5119 to the lens barrel 5117. Observation light taken in from a distal end of the lens barrel 5117 is introduced into the camera head 5119 and enters the lens unit 5121. The lens unit 5121 includes a combination of a plurality of lenses including a zoom lens and a focusing lens. The lens unit 5121 has optical properties adjusted such that the observation light is condensed on a light receiving face of the image pickup element of the image pickup unit 5123. Further, the zoom lens and the focusing lens include such that the positions thereof on their optical axis are movable for adjustment of the magnification and the focal point of a picked up image.

The image pickup unit 5123 includes an image pickup element and disposed at a succeeding stage to the lens unit 5121. Observation light having passed through the lens unit 5121 is condensed on the light receiving face of the image pickup element, and an image signal corresponding to the observation image is generated by photoelectric conversion. The image signal generated by the image pickup unit 5123 is provided to the communication unit 5127.

As the image pickup element which is included by the image pickup unit 5123, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5181 can comprehend a state of the surgical region in enhanced details and can proceed with the surgery more smoothly.

Further, the image pickup element which is included by the image pickup unit 5123 is configured such that it has a pair of image pickup elements for acquiring image signals for the right eye and the left eye compatible with 3D display. Where 3D display is applied, the surgeon 5181 can comprehend the depth of a living body tissue in the surgical region with a higher degree of accuracy. It is to be noted that, if the image pickup unit 5123 is configured as that of the multi-plate type, then a plurality of systems of lens units 5121 are provided corresponding to the individual image pickup elements of the image pickup unit 5123.

The image pickup unit 5123 may not necessarily be provided on the camera head 5119. For example, the image pickup unit 5123 may be provided just behind the objective lens in the inside of the lens barrel 5117.

The driving unit 5125 includes an actuator and moves the zoom lens and the focusing lens of the lens unit 5121 by a predetermined distance along the optical axis under the control of the camera head controlling unit 5129. Consequently, the magnification and the focal point of a picked up image by the image pickup unit 5123 can be adjusted suitably.

The communication unit 5127 includes a communication apparatus for transmitting and receiving various kinds of information to and from the CCU 5153. The communication unit 5127 transmits an image signal acquired from the image pickup unit 5123 as RAW data to the CCU 5153 through the transmission cable 5179. Thereupon, in order to display a picked up image of a surgical region in low latency, preferably the image signal is transmitted by optical communication. This is because, since, upon surgery, the surgeon 5181 performs surgery while observing the state of an affected area through a picked up image, in order to achieve surgery with a higher degree of safety and certainty, it is demanded for a moving image of the surgical region to be displayed on the real time basis as far as possible. Where optical communication is applied, a photoelectric conversion module for converting an electric signal into an optical signal is provided in the communication unit 5127. After the image signal is converted into an optical signal by the photoelectric conversion module, it is transmitted to the CCU 5153 through the transmission cable 5179.

Further, the communication unit 5127 receives a control signal for controlling driving of the camera head 5119 from the CCU 5153. The control signal includes information relating to image pickup conditions such as, for example, information that a frame rate of a picked up image is designated, information that an exposure value upon image picking up is designated and/or information that a magnification and a focal point of a picked up image are designated. The communication unit 5127 provides the received control signal to the camera head controlling unit 5129. It is to be noted that also the control signal from the CCU 5153 may be transmitted by optical communication. In this case, a photoelectric conversion module for converting an optical signal into an electric signal is provided in the communication unit 5127. After the control signal is converted into an electric signal by the photoelectric conversion module, it is provided to the camera head controlling unit 5129.

It is to be noted that the image pickup conditions such as the frame rate, exposure value, magnification or focal point are set automatically by the control unit 5177 of the CCU 5153 on the basis of an acquired image signal. In other words, an auto exposure (AE) function, an auto focus (AF) function and an auto white balance (AWB) function are incorporated in the endoscope 5115.

The camera head controlling unit 5129 controls driving of the camera head 5119 on the basis of a control signal from the CCU 5153 received through the communication unit 5127. For example, the camera head controlling unit 5129 controls driving of the image pickup element of the image pickup unit 5123 on the basis of information that a frame rate of a picked up image is designated and/or information that an exposure value upon image picking up is designated. Further, for example, the camera head controlling unit 5129 controls the driving unit 5125 to suitably move the zoom lens and the focus lens of the lens unit 5121 on the basis of information that a magnification and a focal point of a picked up image are designated. The camera head controlling unit 5129 may include a function for storing information for identifying of the lens barrel 5117 and/or the camera head 5119.

It is to be noted that, by disposing the components such as the lens unit 5121 and the image pickup unit 5123 in a sealed structure having high airtightness and high waterproof, the camera head 5119 can be provided with resistance to an autoclave sterilization process.

Now, a functional configuration of the CCU 5153 is described. The communication unit 5173 includes a communication apparatus for transmitting and receiving various kinds of information to and from the camera head 5119. The communication unit 5173 receives an image signal transmitted thereto from the camera head 5119 through the transmission cable 5179. Thereupon, the image signal may be transmitted preferably by optical communication as described above. In this case, for the compatibility with optical communication, the communication unit 5173 includes a photoelectric conversion module for converting an optical signal into an electric signal. The communication unit 5173 provides the image signal after conversion into an electric signal to the image processing unit 5175.

Further, the communication unit 5173 transmits, to the camera head 5119, a control signal for controlling driving of the camera head 5119. Also the control signal may be transmitted by optical communication.

The image processing unit 5175 performs various image processes for an image signal in the form of RAW data transmitted thereto from the camera head 5119. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5175 performs a detection process for an image signal for performing AE, AF and AWB.

The image processing unit 5175 includes a processor such as a CPU or a GPU, and when the processor operates in accordance with a predetermined program, the image processes and the detection process described above can be performed. It is to be noted that, where the image processing unit 5175 includes a plurality of GPUs, the image processing unit 5175 suitably divides information relating to an image signal such that image processes are performed in parallel by the plurality of GPUs.

The control unit 5177 performs various kinds of control relating to image picking up of a surgical region by the endoscope 5115 and display of the picked up image. For example, the control unit 5177 generates a control signal for controlling driving of the camera head 5119. Thereupon, if image pickup conditions are inputted by the user, then the control unit 5177 generates a control signal on the basis of the input by the user. Alternatively, where the endoscope 5115 has an AE function, an AF function and an AWB function incorporated therein, the control unit 5177 suitably calculates an optimum exposure value, focal distance and white balance in response to a result of a detection process by the image processing unit 5175 and generates a control signal.

Further, the control unit 5177 controls the display apparatus 5155 to display an image of a surgical region on the basis of an image signal for which the image processes have been performed by the image processing unit 5175. Thereupon, the control unit 5177 recognizes various objects in the surgical region image using various image recognition technologies. For example, the control unit 5177 can recognize a surgical tool such as forceps, a particular living body region, bleeding, mist when the energy treatment tool 5135 is used and so forth by detecting the shape, color and so forth of edges of the objects included in the surgical region image. The control unit 5177 causes, when it controls the display apparatus 5155 to display a surgical region image, various kinds of surgery supporting information to be displayed in an overlapping manner with an image of the surgical region using a result of the recognition. Where surgery supporting information is displayed in an overlapping manner and presented to the surgeon 5181, the surgeon 5181 can proceed with the surgery more safety and certainty.

The transmission cable 5179 which connects the camera head 5119 and the CCU 5153 to each other is an electric signal cable ready for communication of an electric signal, an optical fiber ready for optical communication or a composite cable thereof.

Here, while, in the example depicted in the figure, communication is performed by wired communication using the transmission cable 5179, the communication between the camera head 5119 and the CCU 5153 may be performed otherwise by wireless communication. Where the communication between the camera head 5119 and the CCU 5153 is performed by wireless communication, there is no necessity to lay the transmission cable 5179 in the surgery room. Therefore, such a situation that movement of medical staff in the surgery room is disturbed by the transmission cable 5179 can be eliminated.

An example of the surgery room system 5100 to which the technology according to an embodiment of the present disclosure can be applied has been described above. It is to be noted here that, although a case in which the medical system to which the surgery room system 5100 is applied is the endoscopic surgery system 5113 has been described as an example, the configuration of the surgery room system 5100 is not limited to that of the example described above. For example, the surgery room system 5100 may be applied to a soft endoscopic system for inspection or a microscopic surgery system in place of the endoscopic surgery system 5113.

In the endoscope surgery system described above as an example in which a medical light source apparatus is connected to an endoscope, the medical light source apparatus (light source apparatus 5157 in FIG. 17) is mounted on the cart. By mounting the miniaturized medical light source apparatus according to an embodiment of the present technology, it is possible to reduce the size of the entire cart on which various apparatuses including the medical light source apparatus are mounted. Further, by achieving the miniaturization of the medical light source apparatus, the degree of freedom of the installation range of the medical light source apparatus is increased, e.g., the medical light source apparatus can be mounted on a cart, which eliminates the mess of the surgery field and makes the surgical environment better.

Microscopic Surgery System

Hereinafter, a microscopic surgery system to which the technology according to an embodiment of the present disclosure can be applied will be described with reference to FIG. 19 and FIG. 20.

Figure 19:
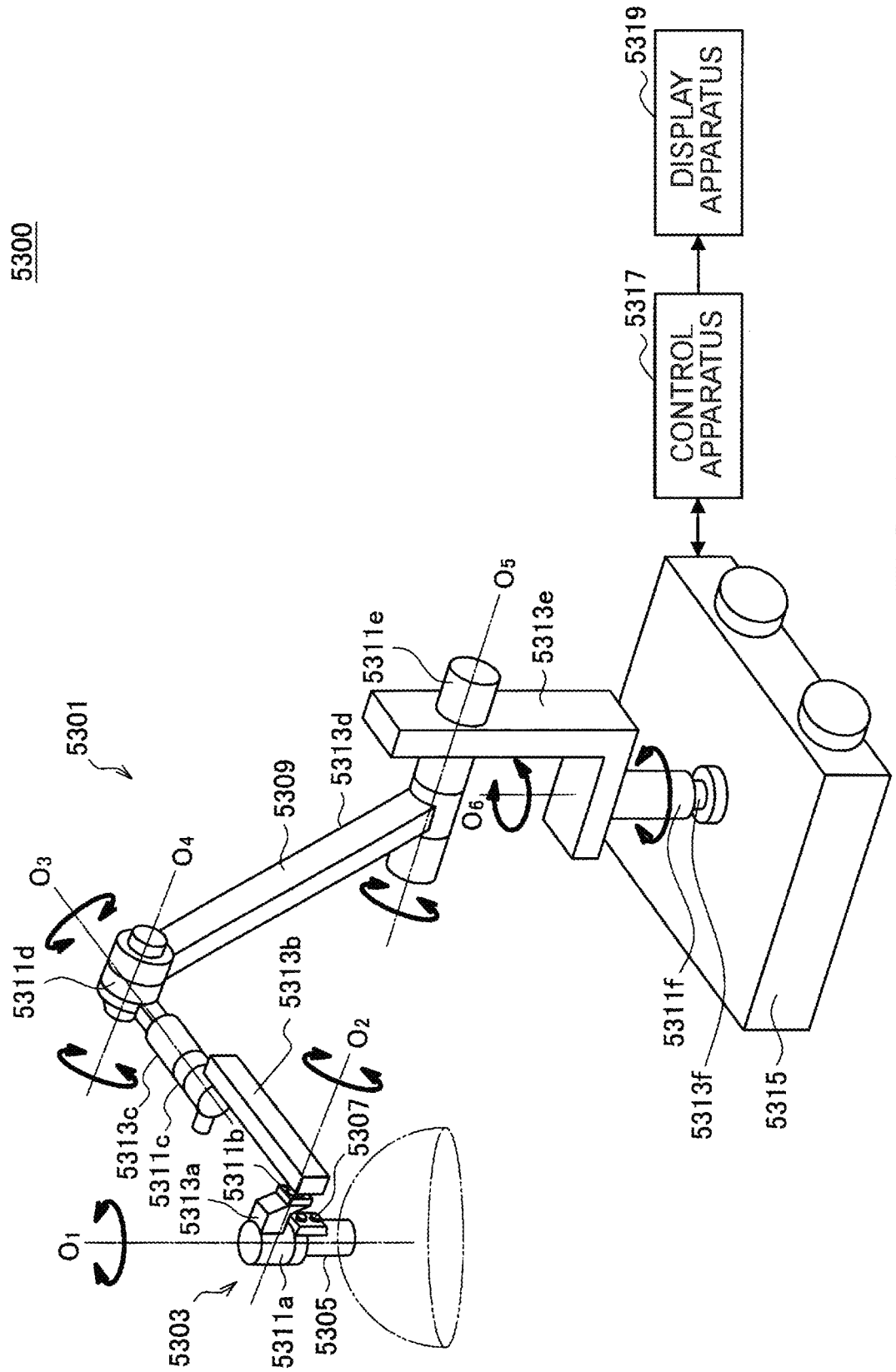
FIG. 19 is a view depicting an example of a schematic configuration of a microscopic surgery system.
Figure 20:
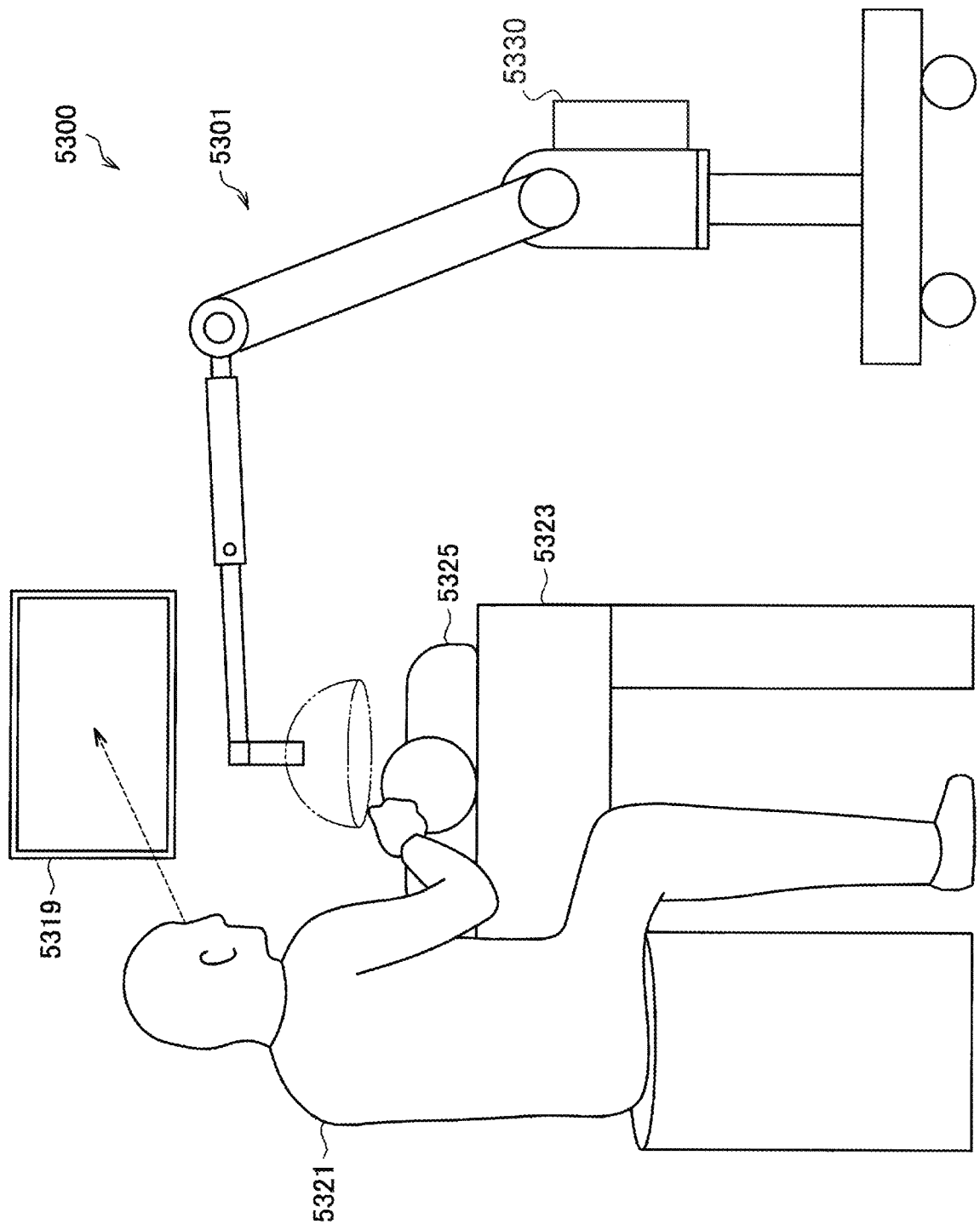
FIG. 20 is a view illustrating a state of surgery in which the microscopic surgery system depicted in FIG. 19 is used.

A light source apparatus denoted by a reference symbol 5350 in FIG. 20 corresponds to the medical light source apparatus according to an embodiment of the present disclosure. As shown in FIG. 20, the light source apparatus 5350 is installed on the side surface of a fifth link 5313e of a microscope apparatus 5301 to be described later. Note that in FIG. 19, illustration of the light source apparatus is omitted.

The output light from the light source apparatus 5350 passes through a light guide cable including an optical fiber and the like provided inside an arm unit 5309 to be described later, and is applied to an observation target via a cover glass from the opening surface of the lower end of a cylindrical portion 5305 of a microscope unit 5303 to be described later.

The microscope system includes the microscope unit 5303 as a microscope, the light source apparatus 5350 to be connected to the microscope unit 5303, and the light guide cable. The microscope unit 5303 guides the output light from the light source apparatus 5350 and applies it to a part to be observed.

FIG. 19 is a view depicting an example of a schematic configuration of a microscopic surgery system 5300 to which the technology according to an embodiment of the present disclosure can be applied. Referring to FIG. 19, the microscopic surgery system 5300 includes a microscope apparatus 5301, a control apparatus 5317 and a display apparatus 5319. It is to be noted that, in the description of the microscopic surgery system 5300, the term "user" signifies an arbitrary one of medical staff members such as a surgery or an assistant who uses the microscopic surgery system 5300.

The microscope apparatus 5301 has a microscope unit 5303 for enlarging an observation target (surgical region of a patient) for observation, an arm unit 5309 which supports the microscope unit 5303 at a distal end thereof, and a base unit 5315 which supports a proximal end of the arm unit 5309.

The microscope unit 5303 includes a cylindrical portion 5305 of a substantially cylindrical shape, an image pickup unit (not depicted) provided in the inside of the cylindrical portion 5305, and an operation unit 5307 provided in a partial region of an outer circumference of the cylindrical portion 5305. The microscope unit 5303 is a microscope unit of the electronic image pickup type (microscope unit of the video type) which picks up an image electronically by the image pickup unit.

A cover glass member for protecting the internal image pickup unit is provided at an opening face of a lower end of the cylindrical portion 5305. Light from an observation target (hereinafter referred to also as observation light) passes through the cover glass member and enters the image pickup unit in the inside of the cylindrical portion 5305. It is to be noted that a light source includes, for example, a light emitting diode (LED) or the like may be provided in the inside of the cylindrical portion 5305, and upon image picking up, light may be irradiated upon an observation target from the light source through the cover glass member.

The image pickup unit includes an optical system which condenses observation light, and an image pickup element which receives the observation light condensed by the optical system. The optical system includes a combination of a plurality of lenses including a zoom lens and a focusing lens. The optical system has optical properties adjusted such that the observation light is condensed to be formed image on a light receiving face of the image pickup element. The image pickup element receives and photoelectrically converts the observation light to generate a signal corresponding to the observation light, namely, an image signal corresponding to an observation image. As the image pickup element, for example, an image pickup element which has a Bayer array and is capable of picking up an image in color is used. The image pickup element may be any of various known image pickup elements such as a complementary metal oxide semiconductor (CMOS) image sensor or a charge coupled device (CCD) image sensor. The image signal generated by the image pickup element is transmitted as RAW data to the control apparatus 5317. Here, the transmission of the image signal may be performed suitably by optical communication. This is because, since, at a surgery site, the surgeon performs surgery while observing the state of an affected area through a picked up image, in order to achieve surgery with a higher degree of safety and certainty, it is demanded for a moving image of the surgical region to be displayed on the real time basis as far as possible. Where optical communication is used to transmit the image signal, the picked up image can be displayed with low latency.

It is to be noted that the image pickup unit may have a driving mechanism for moving the zoom lens and the focusing lens of the optical system thereof along the optical axis. Where the zoom lens and the focusing lens are moved suitably by the driving mechanism, the magnification of the picked up image and the focal distance upon image picking up can be adjusted. Further, the image pickup unit may incorporate therein various functions which may be provided generally in a microscope unit of the electronic image pickup such as an auto exposure (AE) function or an auto focus (AF) function.

Further the image pickup unit may be configured as an image pickup unit of the single-plate type which includes a single image pickup element or may be configured as an image pickup unit of the multi-plate type which includes a plurality of image pickup elements. Where the image pickup unit is configured as that of the multi-plate type, for example, image signals corresponding to red, green, and blue colors may be generated by the image pickup elements and may be synthesized to obtain a color image. Alternatively, the image pickup unit may be configured such that it has a pair of image pickup elements for acquiring image signals for the right eye and the left eye compatible with a stereoscopic vision (three dimensional (3D) display). Where 3D display is applied, the surgeon can comprehend the depth of a living body tissue in the surgical region with a higher degree of accuracy. It is to be noted that, if the image pickup unit is configured as that of stereoscopic type, then a plurality of optical systems are provided corresponding to the individual image pickup elements.

The operation unit 5307 includes, for example, a cross lever, a switch or the like and accepts an operation input of the user. For example, the user can input an instruction to change the magnification of the observation image and the focal distance to the observation target through the operation unit 5307. The magnification and the focal distance can be adjusted by the driving mechanism of the image pickup unit suitably moving the zoom lens and the focusing lens in accordance with the instruction. Further, for example, the user can input an instruction to switch the operation mode of the arm unit 5309 (an all-free mode and a fixed mode hereinafter described) through the operation unit 5307. It is to be noted that when the user intends to move the microscope unit 5303, it is supposed that the user moves the microscope unit 5303 in a state in which the user grasps the microscope unit 5303 holding the cylindrical portion 5305. Accordingly, the operation unit 5307 is preferably provided at a position at which it can be operated readily by the fingers of the user with the cylindrical portion 5305 held such that the operation unit 5307 can be operated even while the user is moving the cylindrical portion 5305.

The arm unit 5309 is configured such that a plurality of links (first link 5313*a* to sixth link 53130 are connected for rotation relative to each other by a plurality of joint portions (first joint portion 5311*a* to sixth joint portion 5311*f*).

The first joint portion 5311*a* has a substantially columnar shape and supports, at a distal end (lower end) thereof, an upper end of the cylindrical portion 5305 of the microscope unit 5303 for rotation around an axis of rotation (first axis $O_1$) parallel to the center axis of the cylindrical portion 5305. Here, the first joint portion 5311*a* may be configured such that the first axis $O_1$ thereof is in alignment with the optical axis of the image pickup unit of the microscope unit 5303. By the configuration, if the microscope unit 5303 is rotated around the first axis $O_1$, then the field of view can be changed so as to rotate the picked up image.

The first link 5313*a* fixedly supports, at a distal end thereof, the first joint portion 5311*a*. Specifically, the first link 5313*a* is a bar-like member having a substantially L shape and is connected to the first joint portion 5311*a* such that one side at the distal end side thereof extends in a direction orthogonal to the first axis $O_1$ and an end portion of the one side abuts with an upper end portion of an outer periphery of the first joint portion 5311*a*. The second joint portion 5311*b* is connected to an end portion of the other side on the proximal end side of the substantially L shape of the first link 5313*a*.

The second joint portion 5311*b* has a substantially columnar shape and supports, at a distal end thereof, a proximal end of the first link 5313*a* for rotation around an axis of rotation (second axis $O_2$) orthogonal to the first axis $O_1$. The second link 5313*b* is fixedly connected at a distal end thereof to a proximal end of the second joint portion 5311*b*.

The second link 5313*b* is a bar-like member having a substantially L shape, and one side of a distal end side of the second link 5313*b* extends in a direction orthogonal to the second axis $O_2$ and an end portion of the one side is fixedly connected to a proximal end of the second joint portion 5311*b*. The third joint portion 5311*c* is connected to the other side at the proximal end side of the substantially L shape of the second link 5313*b*.

The third joint portion 5311*c* has a substantially columnar shape and supports, at a distal end thereof, a proximal end of the second link 5313*b* for rotation around an axis of rotation (third axis $O_3$) orthogonal to the first axis $O_1$ and the second axis $O_2$. The third link 5313*c* is fixedly connected at a distal end thereof to a proximal end of the third joint portion 5311*c*. By rotating the components at the distal end side including the microscope unit 5303 around the second axis $O_2$ and the third axis $O_3$, the microscope unit 5303 can be moved such that the position of the microscope unit 5303 is changed within a horizontal plane. In other words, by controlling the rotation around the second axis $O_2$ and the third axis $O_3$, the field of view of the picked up image can be moved within a plane.

The third link 5313*c* is configured such that the distal end side thereof has a substantially columnar shape, and a proximal end of the third joint portion 5311*c* is fixedly connected to the distal end of the columnar shape such that both of them have a substantially same center axis. The proximal end side of the third link 5313*c* has a prismatic shape, and the fourth joint portion 5311*d* is connected to an end portion of the third link 5313*c*.

The fourth joint portion 5311*d* has a substantially columnar shape and supports, at a distal end thereof, a proximal end of the third link 5313*c* for rotation around an axis of rotation (fourth axis $O_4$) orthogonal to the third axis $O_3$. The fourth link 5313d is fixedly connected at a distal end thereof to a proximal end of the fourth joint portion 5311d.

The fourth link 5313d is a bar-like member extending substantially linearly and is fixedly connected to the fourth joint portion 5311d such that it extends orthogonally to the fourth axis $O_4$ and abuts at an end portion of the distal end thereof with a side face of the substantially columnar shape of the fourth joint portion 5311d. The fifth joint portion 5311e is connected to a proximal end of the fourth link 5313d.

The fifth joint portion 5311e has a substantially columnar shape and supports, at a distal end side thereof, a proximal end of the fourth link 5313d for rotation around an axis of rotation (fifth axis $O_5$) parallel to the fourth axis $O_4$. The fifth link 5313e is fixedly connected at a distal end thereof to a proximal end of the fifth joint portion 5311e. The fourth axis $O_4$ and the fifth axis $O_5$ are axes of rotation around which the microscope unit 5303 can be moved in the upward and downward direction. By rotating the components at the distal end side including the microscope unit 5303 around the fourth axis $O_4$ and the fifth axis $O_5$, the height of the microscope unit 5303, namely, the distance between the microscope unit 5303 and an observation target, can be adjusted.

The fifth link 5313e includes a combination of a first member having a substantially L shape one side of which extends in the vertical direction and the other side of which extends in the horizontal direction, and a bar-like second member extending vertically downwardly from the portion of the first member which extends in the horizontal direction. The fifth joint portion 5311e is fixedly connected at a proximal end thereof to a neighboring upper end of a part extending the first member of the fifth link 5313e in the vertical direction. The sixth joint portion 5311f is connected to proximal end (lower end) of the second member of the fifth link 5313e.

The sixth joint portion 5311f has a substantially columnar shape and supports, at a distal end side thereof, a proximal end of the fifth link 5313e for rotation around an axis of rotation (sixth axis $O_6$) parallel to the vertical direction. The sixth link 5313f is fixedly connected at a distal end thereof to a proximal end of the sixth joint portion 5311f.

The sixth link 5313f is a bar-like member extending in the vertical direction and is fixedly connected at a proximal end thereof to an upper face of the base unit 5315.

The first joint portion 5311a to sixth joint portion 5311f have movable ranges suitably set such that the microscope unit 5303 can make a desired movement. Consequently, in the arm unit 5309 having the configuration described above, a movement of totaling six degrees of freedom including three degrees of freedom for translation and three degrees of freedom for rotation can be implemented with regard to a movement of the microscope unit 5303. By configuring the arm unit 5309 such that six degrees of freedom are implemented for movements of the microscope unit 5303 in this manner, the position and the posture of the microscope unit 5303 can be controlled freely within the movable range of the arm unit 5309. Accordingly, it is possible to observe a surgical region from every angle, and surgery can be executed more smoothly.

It is to be noted that the configuration of the arm unit 5309 as depicted is an example at all, and the number and shape (length) of the links including the arm unit 5309 and the number, location, direction of the axis of rotation and so forth of the joint portions may be designed suitably such that desired degrees of freedom can be implemented. For example, in order to freely move the microscope unit 5303, preferably the arm unit 5309 is configured so as to have six degrees of freedom as described above. However the arm unit 5309 may also be configured so as to have much greater degree of freedom (namely, redundant degree of freedom). Where a redundant degree of freedom exists, it is possible to change the posture of the arm unit 5309 in a state in which the position and the posture of the microscope unit 5303 are fixed. Accordingly, control can be implemented which is higher in convenience to the surgeon such as to control the posture of the arm unit 5309 such that, for example, the arm unit 5309 does not interfere with the field of view of the surgeon who watches the display apparatus 5319.

Here, an actuator in which a driving mechanism such as a motor, an encoder which detects an angle of rotation at each joint portion and so forth are incorporated may be provided for each of the first joint portion 5311a to sixth joint portion 5311f. By suitably controlling driving of the actuators provided in the first joint portion 5311a to sixth joint portion 5311f by the control apparatus 5317, the posture of the arm unit 5309, namely, the position and the posture of the microscope unit 5303, can be controlled. Specifically, the control apparatus 5317 can comprehend the posture of the arm unit 5309 at present and the position and the posture of the microscope unit 5303 at present on the basis of information regarding the angle of rotation of the joint portions detected by the encoders. The control apparatus 5317 uses the comprehended information to calculate a control value (for example, an angle of rotation or torque to be generated) for each joint portion with which a movement of the microscope unit 5303 in accordance with an operation input from the user is implemented. Accordingly the control apparatus 5317 drives driving mechanism of the each joint portion in accordance with the control value. It is to be noted that, in this case, the control method of the arm unit 5309 by the control apparatus 5317 is not limited, and various known control methods such as force control or position control may be applied.

For example, when the surgeon performs operation inputting suitably through an inputting apparatus not depicted, driving of the arm unit 5309 may be controlled suitably in response to the operation input by the control apparatus 5317 to control the position and the posture of the microscope unit 5303. By this control, it is possible to support, after the microscope unit 5303 is moved from an arbitrary position to a different arbitrary position, the microscope unit 5303 fixedly at the position after the movement. It is to be noted that, as the inputting apparatus, preferably an inputting apparatus is applied which can be operated by the surgeon even if the surgeon has a surgical tool in its hand such as, for example, a foot switch taking the convenience to the surgeon into consideration. Further, operation inputting may be performed in a contactless fashion on the basis of gesture detection or line-of-sight detection in which a wearable device or a camera which is provided in the surgery room is used. This makes it possible even for a user who belongs to a clean area to operate an apparatus belonging to an unclean area with a high degree of freedom. In addition, the arm unit 5309 may be operated in a master-slave fashion. In this case, the arm unit 5309 may be remotely controlled by the user through an inputting apparatus which is placed at a place remote from the surgery room.

Further, where force control is applied, the control apparatus 5317 may perform power-assisted control to drive the actuators of the first joint portion 5311a to sixth joint portion 5311f such that the arm unit 5309 may receive external force by the user and move smoothly following the external force. This makes it possible to move, when the user holds and directly moves the position of the microscope unit 5303, the microscope unit 5303 with comparatively weak force. Accordingly, it becomes possible for the user to move the microscope unit 5303 more intuitively by a simpler and easier operation, and the convenience to the user can be improved.

Further, driving of the arm unit 5309 may be controlled such that the arm unit 5309 performs a pivot movement. The pivot movement here is a motion for moving the microscope unit 5303 such that the direction of the optical axis of the microscope unit 5303 is kept toward a predetermined point (hereinafter referred to as pivot point) in a space. Since the pivot movement makes it possible to observe the same observation position from various directions, more detailed observation of an affected area becomes possible. It is to be noted that, where the microscope unit 5303 is configured such that the focal distance thereof is fixed, preferably the pivot movement is performed in a state in which the distance between the microscope unit 5303 and the pivot point is fixed. In this case, the distance between the microscope unit 5303 and the pivot point may be adjusted to a fixed focal distance of the microscope unit 5303 in advance. By the configuration just described, the microscope unit 5303 comes to move on a hemispherical plane (schematically depicted in FIG. 19) having a diameter corresponding to the focal distance centered at the pivot point, and even if the observation direction is changed, a clear picked up image can be obtained. On the other hand, where the microscope unit 5303 is configured such that the focal distance thereof is adjustable, the pivot movement may be performed in a state in which the distance between the microscope unit 5303 and the pivot point is variable. In this case, for example, the control apparatus 5317 may calculate the distance between the microscope unit 5303 and the pivot point on the basis of information regarding the angles of rotation of the joint portions detected by the encoders and automatically adjust the focal distance of the microscope unit 5303 on the basis of a result of the calculation. Alternatively, where the microscope unit 5303 includes an AF function, adjustment of the focal distance may be performed automatically by the AF function every time the changing in distance caused by the pivot movement between the microscope unit 5303 and the pivot point.

Further, each of the first joint portion 5311a to sixth joint portion 5311f may be provided with a brake for constraining the rotation of the first joint portion 5311a to sixth joint portion 5311f. Operation of the brake may be controlled by the control apparatus 5317. For example, if it is intended to fix the position and the posture of the microscope unit 5303, then the control apparatus 5317 renders the brakes of the joint portions operative. Consequently, even if the actuators are not driven, the posture of the arm unit 5309, namely, the position and posture of the microscope unit 5303, can be fixed, and therefore, the power consumption can be reduced. When it is intended to move the position and the posture of the microscope unit 5303, the control apparatus 5317 may release the brakes of the joint portions and drive the actuators in accordance with a predetermined control method.

Such operation of the brakes may be performed in response to an operation input by the user through the operation unit 5307 described hereinabove. When the user intends to move the position and the posture of the microscope unit 5303, the user would operate the operation unit 5307 to release the brakes of the joint portions. Consequently, the operation mode of the arm unit 5309 changes to a mode in which rotation of the joint portions can be performed freely (all-free mode). On the other hand, if the user intends to fix the position and the posture of the microscope unit 5303, then the user would operate the operation unit 5307 to render the brakes of the joint portions operative. Consequently, the operation mode of the arm unit 5309 changes to a mode in which rotation of the joint portions is constrained (fixed mode).

The control apparatus 5317 integrally controls operation of the microscopic surgery system 5300 by controlling operation of the microscope apparatus 5301 and the display apparatus 5319. For example, the control apparatus 5317 renders the actuators of the first joint portion 5311a to sixth joint portion 5311f operative in accordance with a predetermined control method to control driving of the arm unit 5309. Further, for example, the control apparatus 5317 controls operation of the brakes of the first joint portion 5311a to sixth joint portion 5311f to change the operation mode of the arm unit 5309. Further, for example, the control apparatus 5317 performs various signal processes for an image signal acquired by the image pickup unit of the microscope unit 5303 of the microscope apparatus 5301 to generate image data for display and controls the display apparatus 5319 to display the generated image data. As the signal processes, various known signal processes such as, for example, a development process (demosaic process), an image quality improving process (a bandwidth enhancement process, a super-resolution process, a noise reduction (NR) process and/or an image stabilization process) and/or an enlargement process (namely, an electronic zooming process) may be performed.

It is to be noted that communication between the control apparatus 5317 and the microscope unit 5303 and communication between the control apparatus 5317 and the first joint portion 5311a to sixth joint portion 5311f may be wired communication or wireless communication. Where wired communication is applied, communication by an electric signal may be performed or optical communication may be performed. In this case, a cable for transmission used for wired communication may be configured as an electric signal cable, an optical fiber or a composite cable of them in response to an applied communication method. On the other hand, where wireless communication is applied, since there is no necessity to lay a transmission cable in the surgery room, such a situation that movement of medical staff in the surgery room is disturbed by a transmission cable can be eliminated.

The control apparatus 5317 may be a processor such as a central processing unit (CPU) or a graphics processing unit (GPU), or a microcomputer or a control board in which a processor and a storage element such as a memory are incorporated. The various functions described hereinabove can be implemented by the processor of the control apparatus 5317 operating in accordance with a predetermined program. It is to be noted that, in the example depicted, the control apparatus 5317 is provided as an apparatus separate from the microscope apparatus 5301. However, the control apparatus 5317 may be installed in the inside of the base unit 5315 of the microscope apparatus 5301 and configured integrally with the microscope apparatus 5301. The control apparatus 5317 may also include a plurality of apparatus. For example, microcomputers, control boards or the like may be disposed in the microscope unit 5303 and the first joint portion 5311a to sixth joint portion 5311f of the arm unit 5309 and connected for communication with each other to implement functions similar to those of the control apparatus 5317.

The display apparatus 5319 is provided in the surgery room and displays an image corresponding to image data generated by the control apparatus 5317 under the control of the control apparatus 5317. In other words, an image of a surgical region picked up by the microscope unit 5303 is displayed on the display apparatus 5319. The display apparatus 5319 may display, in place of or in addition to an image of a surgical region, various kinds of information relating to the surgery such as physical information of a patient or information regarding a surgical procedure of the surgery. In this case, the display of the display apparatus 5319 may be switched suitably in response to an operation by the user. Alternatively, a plurality of such display apparatus 5319 may also be provided such that an image of a surgical region or various kinds of information relating to the surgery may individually be displayed on the plurality of display apparatus 5319. It is to be noted that, as the display apparatus 5319, various known display apparatus such as a liquid crystal display apparatus or an electro luminescence (EL) display apparatus may be applied.

FIG. 20 is a view illustrating a state of surgery in which the microscopic surgery system 5300 depicted in FIG. 19 is used. FIG. 20 schematically illustrates a state in which a surgeon 5321 uses the microscopic surgery system 5300 to perform surgery for a patient 5325 on a patient bed 5323. It is to be noted that, in FIG. 20, for simplified illustration, the control apparatus 5317 from among the components of the microscopic surgery system 5300 is omitted and the microscope apparatus 5301 is depicted in a simplified from.

As depicted in FIG. 20, upon surgery, using the microscopic surgery system 5300, an image of a surgical region picked up by the microscope apparatus 5301 is displayed in an enlarged scale on the display apparatus 5319 installed on a wall face of the surgery room. The display apparatus 5319 is installed at a position opposing to the surgeon 5321, and the surgeon 5321 would perform various treatments for the surgical region such as, for example, resection of the affected area while observing a state of the surgical region from a video displayed on the display apparatus 5319.

An example of the microscopic surgery system 5300 to which the technology according to an embodiment of the present disclosure can be applied has been described. It is to be noted here that, while the microscopic surgery system 5300 is described as an example, the system to which the technology according to an embodiment of the present disclosure can be applied is not limited to this example. For example, the microscope apparatus 5301 may also function as a supporting arm apparatus which supports, at a distal end thereof, a different observation apparatus or some other surgical tool in place of the microscope unit 5303. As the other observation apparatus, for example, an endoscope may be applied. Further, as the different surgical tool, forceps, a pair of tweezers, a pneumoperitoneum tube for pneumoperitoneum or an energy treatment tool for performing incision of a tissue or sealing of a blood vessel by cautery and so forth can be applied. By supporting any of such an observation apparatus and surgical tools as just described by the supporting apparatus, the position of them can be fixed with a high degree of stability in comparison with that in an alternative case in which they are supported by hands of medical staff. Accordingly, the burden on the medical staff can be reduced. The technology according to an embodiment of the present disclosure may be applied to a supporting arm apparatus which supports such a component as described above other than the microscopic unit.

In the microscope apparatus 5301 described above as an example in which a medical light source apparatus is connected to a microscope, as shown in FIG. 20, the medical light source apparatus (light source apparatus 5330 in FIG. 20) is installed on the side surface of the link. By mounting the miniaturized medical light source apparatus according to an embodiment of the present technology, it is possible to reduce the size of the entire microscope apparatus, e.g., the user hardly collides with the microscope apparatus, which makes the surgical environment better.

It should be noted that the present technology can take the following configurations.

(1) A medical observation system for observing a biological object, the system including:
    a medical light source apparatus for illuminating the biological object, the medical light source apparatus including
    a first laser light source configured to emit a first laser light beam,
    a second laser light source configured to emit a second laser light beam having a wavelength band different from a wavelength band of the first laser light beam,
    an optical assembly including a reflecting surface disposed to reflect the first laser light beam, cause the second laser light beam to be transmitted therethrough, and guide the first laser light beam and the second laser light beam in a same direction, and
    a reflection mirror having a reflecting surface that is not parallel with the reflecting surface of the optical assembly and configured to reflect the second laser light beam to cause the second laser light beam to enter the optical assembly; and
    a medical observation device including a detector for detecting a light received from the biological object.

(2) A medical light source apparatus for illuminating a biological object, the medical light source apparatus including:
    a first laser light source configured to emit a first laser light beam;
    a second laser light source configured to emit a second laser light beam having a wavelength band different from a wavelength band of the first laser light beam;
    an optical assembly including a reflecting surface and disposed to reflect the first laser light beam, cause the second laser light beam to be transmitted therethrough, guide the first laser light beam and the second laser light beam in a same direction, and produce output light that illuminates the biological object; and
    a reflection mirror having a reflecting surface that is not parallel with the reflecting surface of the optical assembly and configured to reflect the second laser light beam to cause the second laser light beam to enter the optical assembly.

(3) The medical light source apparatus according to (2), wherein: the first laser light beam and the second laser light beam are emitted in opposite directions.

(4) The medical light source apparatus according to (2), wherein: the reflecting surface of the optical assembly is perpendicular to the reflecting surface of the reflection mirror.

(5) The medical light source apparatus according to (3), wherein: the optical assembly is configured to reflect the first laser light beam to redirect an optical path of the first laser light beam by 90 degrees, and the reflection mirror is further configured to reflect the second laser light beam to redirect an optical path of the second laser light beam by 90 degrees.

(6) The medical light source apparatus according to (2), wherein: a wavelength of the first laser light beam is shorter than a wavelength of the second laser light beam.

(7) The medical light source apparatus according to (2), wherein: the first laser light source, the second laser light source, the optical assembly, and the reflection mirror are configured to form a first group, the medical light source apparatus further including:
    a third laser light source configured to emit a third laser light beam;
    a fourth laser light source configured to emit a fourth laser light beam having a wavelength band different from a wavelength band of the third laser light beam; a second optical assembly including a reflecting surface and disposed to reflect the third laser light beam, cause the fourth laser light beam to be transmitted therethrough, guide the third laser light beam and the fourth laser light beam in a same direction, and produce a second output light that illuminates the biological object;
    a second reflection mirror having a reflecting surface that is not parallel with the reflecting surface of the second optical assembly and configured to reflect the fourth laser light beam to cause the fourth laser light beam to enter the second optical assembly, the third laser light source, the fourth laser light source, the second optical assembly, and the second reflection mirror are configured to form a second group; and a condenser lens that receives the output light from the first group and the second output light from the second group and condenses the received light.

(8) The medical light source apparatus according to (7), further including: a rod integrator that receives a light beam condensed by the condenser lens.

(9) The medical light source apparatus according to (2), wherein:
    the first laser light source is configured to emit the first laser light beam having a red wavelength band, the second laser light source is configured to emit the second laser light beam having a blue wavelength band, a third laser light source is configured to emit a third laser light beam having a green wavelength band, and
    the medical light source apparatus further comprises a condenser lens that receives the output light from the first group and condenses the received light,
    wherein the received light received by the condenser lens includes a red light beam from the first laser light source, a blue light beam from the second laser light source, and a green light beam from the third laser light source that overlap each other at the condenser lens.

(10) The medical light source apparatus according to (9), wherein: an outermost portion of the received light at the condenser lens includes a portion of the red light beam, a portion of the blue light beam and a portion of the green light beam.

(11) The medical light source apparatus according to (9), further including:
    a fifth laser light source configured to emit a fifth laser light beam;
    a sixth laser light source configured to emit a sixth laser light beam having a wavelength band different from a wavelength band of the fifth laser light beam;
    a third optical assembly including a reflecting surface and disposed to reflect the fifth laser light beam, cause the sixth laser light beam to be transmitted therethrough, guide the fifth laser light beam and the sixth laser light beam in a same direction, and produce a third output light that illuminates the biological object;
    a third reflection mirror having a reflecting surface that is not parallel with the reflecting surface of the third optical assembly and configured to reflect the sixth laser light beam to cause the sixth laser light beam to enter the third optical assembly, the fifth laser light source, the sixth laser light source, the third optical assembly, and the third reflection mirror are configured to form a third group; two groups out of the first, second, and third groups include the green laser light source and the red laser light source, and
    a remaining one of the first, second, and third groups includes the blue laser light source and the green laser light source.

(12) The medical light source apparatus according to (7), further including: an infrared laser light source configured to emit an infrared light beam that enters the condenser lens.

(13) The medical light source apparatus according to (7), further including: a violet laser light source configured to emit a violet light beam that enters the condenser lens.

(14) The medical light source apparatus according to (2), further including: an enclosure, the first laser light source and the second laser light source being placed on the same surface of the enclosure.

(15) The medical light source apparatus according to (2), further including: a heat sink configured to receive heat generated from the first laser light source and the second laser light source.

(16) The medical light source apparatus according to (15), wherein: the heat sink includes a Peltier device.

(17) The medical light source apparatus according to (2), wherein: an intensity of the output light is adjusted by controlling output intensity of the first laser light beam and the second laser light beam.

(18) The medical light source apparatus according to (2), wherein: the medical light source apparatus is configured to supply the output light to a microscope or an endoscope.

(19) The medical light source apparatus according to (2), wherein: the optical assembly includes a dichroic mirror, a dichroic filter, or a prism.

(20) The medical observation system according to (1), wherein: the optical assembly includes a dichroic mirror, a dichroic filter, or a prism.

(21) The medical observation system according to (1), wherein: the optical viewing assembly includes a microscope or an endoscope.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1 endoscope system
2 endoscope
3 part to be observed (irradiated body)
5, 5157, 5330 light source apparatus (medical light source apparatus)
51R first R light source (red laser light source, second laser light source)
52R second R light source (red laser light source, second laser light source)
53G first G light source (green laser light source, second laser light source)
54G second G light source (green laser light source, first laser light source)
55G third G light source (green laser light source, first laser light source)
56B B light source (blue laser light source, first laser light source)
57IR IR light source (infrared laser light source)
58V V light source (violet laser light source)

59 condenser lens
61 rod integrator
64, 164, 264 first dichroic mirror (dichroic mirror)
65, 165, 265 first reflection mirror (reflection mirror)
66, 166, 266 second dichroic mirror (dichroic mirror)
67, 167, 267 second reflection mirror (reflection mirror)
68, 168, 268 third dichroic mirror (dichroic mirror)
69, 169, 269 third reflection mirror (reflection mirror)
81, 181 first optical system group (group)
82, 182 second optical system group (group)
83, 183 third optical system group (group)
91 first optical path (optical path)
92 second optical path (optical path)
93 third optical path (optical path)
94 enclosure
151G first G light source (green laser light source, second laser light source)
152G second G light source (green laser light source, second laser light source)
153G third G light source (green laser light source, second laser light source)
154B first B light source (blue laser light source, first laser light source)
155B second B light source (blue laser light source, first laser light source)
156B third B light source (blue laser light source, first laser light source)
157R R light source (red laser light source)
251G first G light source (green laser light source, second laser light source)
252G second G light source (green laser light source, second laser light source)
253G third G light source (green laser light source, second laser light source)
254B first B light source (blue laser light source, first laser light source)
255B second B light source (blue laser light source, first laser light source)
256B third B light source (blue laser light source, first laser light source)
257R first R light source (red laser light source)
258R second R light source (red laser light source)
259R third R light source (red laser light source)
5157, 5330 light source apparatus (medical light source apparatus)
5300 microscopic surgery system
5303 microscope unit (microscope)

The invention claimed is:

1. A medical observation system for observing a biological object, the system comprising:
a medical light source apparatus for illuminating the biological object, the medical light source apparatus including
a first laser light source configured to emit a first laser light beam,
a second laser light source configured to emit a second laser light beam having a wavelength band different from a wavelength band of the first laser light beam,
a first optical assembly including a reflecting surface disposed to reflect the first laser light beam, cause the second laser light beam to be transmitted therethrough, and guide the first laser light beam and the second laser light beam in a same direction and produce first output light that illuminates the biological object, and
a first reflection mirror having a reflecting surface that is not parallel with the reflecting surface of the first optical assembly and configured to reflect the second laser light beam to cause the second laser light beam to enter the first optical assembly, wherein the first laser light source, the second laser light source, the first optical assembly, and the first reflection mirror form a first group;
a third laser light source configured to emit a third laser light beam,
a fourth laser light source configured to emit a fourth laser light beam having a wavelength band different from a wavelength band of the third laser light beam,
a second optical assembly including a reflecting surface and disposed to reflect the third laser light beam, cause the fourth laser light beam to be transmitted therethrough, guide the third laser light beam and the fourth laser light beam in a same direction, and produce a second output light that illuminates the biological object;
a second reflection mirror having a reflecting surface that is not parallel with the reflecting surface of the second optical assembly and configured to reflect the fourth laser light beam to cause the fourth laser light beam to enter the second optical assembly, wherein the third laser light source, the fourth laser light source, the second optical assembly, and the second reflection mirror form a second group;
a condenser lens that receives the first output light from the first group and the second output light from the second group and condenses the received light; and
a medical observation device including a detector for detecting a light received from the biological object.

2. The medical light source apparatus according to claim 1, further comprising:
a rod integrator that receives a light beam condensed by the condenser lens.

3. The medical observation system according to claim 1, wherein:
the first optical assembly includes a dichroic mirror, a dichroic filter, or a prism.

4. The medical observation system according to claim 1, wherein:
the first optical assembly includes a microscope or an endoscope.

5. A medical light source apparatus for illuminating a biological object, the medical light source apparatus comprising:
a first laser light source configured to emit a first laser light beam;
a second laser light source configured to emit a second laser light beam having a wavelength band different from a wavelength band of the first laser light beam;
a first optical assembly including a reflecting surface disposed to reflect the first laser light beam, cause the second laser light beam to be transmitted therethrough, and guide the first laser light beam and the second laser light beam in a same direction and produce first output light that illuminates the biological object, and
a first reflection mirror having a reflecting surface that is not parallel with the reflecting surface of the first optical assembly and configured to reflect the second laser light beam to cause the second laser light beam to enter the first optical assembly, wherein the first laser light source, the second laser light source, the first optical assembly, and the first reflection mirror form a first group;
a third laser light source configured to emit a third laser light beam;

a fourth laser light source configured to emit a fourth laser light beam having a wavelength band different from a wavelength band of the third laser light beam;

a second optical assembly including a reflecting surface and disposed to reflect the third laser light beam, cause the fourth laser light beam to be transmitted therethrough, guide the third laser light beam and the fourth laser light beam in a same direction, and produce a second output light that illuminates the biological object;

a second reflection mirror having a reflecting surface that is not parallel with the reflecting surface of the second optical assembly and configured to reflect the fourth laser light beam to cause the fourth laser light beam to enter the second optical assembly, wherein the third laser light source, the fourth laser light source, the second optical assembly, and the second reflection mirror form a second group; and a condenser lens that receives the first output light from the first group and the second output light from the second group and condenses the received light.

6. The medical light source apparatus according to claim 5, wherein:

the first laser light beam and the second laser light beam are emitted in opposite directions.

7. The medical light source apparatus according to claim 6, wherein:

the first optical assembly is configured to reflect the first laser light beam to redirect an optical path of the first laser light beam by 90 degrees, and the first reflection mirror is further configured to reflect the second laser light beam to redirect an optical path of the second laser light beam by 90 degrees.

8. The medical light source apparatus according to claim 5, wherein:

the reflecting surface of the first optical assembly is perpendicular to the reflecting surface of the first reflection mirror.

9. The medical light source apparatus according to claim 5, wherein:

a wavelength of the first laser light beam is shorter than a wavelength of the second laser light beam.

10. The medical light source apparatus according to claim 5, wherein:

the first laser light source is configured to emit the first laser light beam having a red wavelength band, the second laser light source is configured to emit the second laser light beam having a blue wavelength band, a third laser light source is configured to emit a third laser light beam having a green wavelength band, and the medical light source apparatus further comprises a condenser lens that receives the output light from the first group and condenses the received light, wherein the received light received by the condenser lens includes a red light beam from the first laser light source, a blue light beam from the second laser light source, and a green light beam from the third laser light source that overlap each other at the condenser lens.

11. The medical light source apparatus according to claim 10, wherein:

an outermost portion of the received light at the condenser lens includes a portion of the red light beam, a portion of the blue light beam and a portion of the green light beam.

12. The medical light source apparatus according to claim 10, further comprising:

a fifth laser light source configured to emit a fifth laser light beam;

a sixth laser light source configured to emit a sixth laser light beam having a wavelength band different from a wavelength band of the fifth laser light beam;

a third optical assembly including a reflecting surface and disposed to reflect the fifth laser light beam, cause the sixth laser light beam to be transmitted therethrough, guide the fifth laser light beam and the sixth laser light beam in a same direction, and produce a third output light that illuminates the biological object;

a third reflection mirror having a reflecting surface that is not parallel with the reflecting surface of the third optical assembly and configured to reflect the sixth laser light beam to cause the sixth laser light beam to enter the third optical assembly, the fifth laser light source, the sixth laser light source, the third optical assembly, and the third reflection mirror are configured to form a third group; two groups out of the first, second, and third groups include the green laser light source and the red laser light source, and a remaining one of the first, second, and third groups includes the blue laser light source and the green laser light source.

13. The medical light source apparatus according to claim 5, further comprising:

an infrared laser light source configured to emit an infrared light beam that enters the condenser lens.

14. The medical light source apparatus according to claim 5, further comprising:

a violet laser light source configured to emit a violet light beam that enters the condenser lens.

15. The medical light source apparatus according to claim 5, further comprising:

an enclosure, the first laser light source and the second laser light source being placed on the same surface of the enclosure.

16. The medical light source apparatus according to claim 5, further comprising:

a heat sink configured to receive heat generated from the first laser light source and the second laser light source.

17. The medical light source apparatus according to claim 16, wherein:

the heat sink includes a Peltier device.

18. The medical light source apparatus according to claim 5, wherein:

an intensity of the output light is adjusted by controlling output intensity of the first laser light beam and the second laser light beam.

19. The medical light source apparatus according to claim 5, wherein:

the medical light source apparatus is configured to supply the output light to a microscope or an endoscope.

20. The medical light source apparatus according to claim 5, wherein:

the first optical assembly includes a dichroic mirror, a dichroic filter, or a prism.

21. A medical light source apparatus for illuminating a biological object, the medical light source apparatus comprising:

a first laser light source configured to emit a first laser light beam;

a second laser light source configured to emit a second laser light beam having a wavelength band different from a wavelength band of the first laser light beam;

a first optical assembly including a reflecting surface disposed to reflect the first laser light beam, cause the second laser light beam to be transmitted therethrough, and guide the first laser light beam and the second laser light beam in a same direction and produce first output light that illuminates the biological object;

a first reflection mirror having a reflecting surface that is not parallel with the reflecting surface of the first optical assembly and configured to reflect the second laser light beam to cause the second laser light beam to enter the first optical assembly, wherein the first laser light source, the second laser light source, the first optical assembly, and the first reflection mirror form a first group;

a third laser light source configured to emit a third laser light beam;

a fourth laser light source configured to emit a fourth laser light beam having a wavelength band different from a wavelength band of the third laser light beam;

a second optical assembly including a reflecting surface and disposed to reflect the third laser light beam, cause the third laser light beam to be transmitted therethrough, guide the third laser light beam and the fourth laser light beam in a same direction, and produce a second output light that illuminates the biological object;

a second reflection mirror having a reflecting surface that is not parallel with the reflecting surface of the second optical assembly and configured to reflect the fourth laser light beam to cause the fourth laser light beam to enter the second optical assembly, the third laser light source, the fourth laser light source, the second optical assembly, and the second reflection mirror form a second group; and a condenser lens that condenses received light, wherein the received light received by the condenser lens includes a red light beam from the first laser light source, a blue light beam from the second laser light source, and a green light beam from the third laser light source that overlap each other at the condenser lens.

* * * * *